US009090583B2

(12) United States Patent
Ding et al.

(10) Patent No.: US 9,090,583 B2
(45) Date of Patent: Jul. 28, 2015

(54) BENZOPYRONE ESTROGEN RECEPTOR REGULATOR

(75) Inventors: Hongxia Ding, Beijing (CN); Kun Meng, Beijing (CN); Jin Li, Beijing (CN)

(73) Assignee: BEIJING SHENOGEN PHARMA GROUP LTD., Beijing (CN)

( * ) Notice: Subject to any disclaimer, the term of this patent is extended or adjusted under 35 U.S.C. 154(b) by 0 days.

(21) Appl. No.: 13/977,149

(22) PCT Filed: Dec. 21, 2011

(86) PCT No.: PCT/CN2011/084321
§ 371 (c)(1),
(2), (4) Date: Jul. 29, 2013

(87) PCT Pub. No.: WO2012/089051
PCT Pub. Date: Jul. 5, 2012

(65) Prior Publication Data
US 2013/0303544 A1  Nov. 14, 2013

(30) Foreign Application Priority Data

Dec. 31, 2010  (CN) .......................... 2010 1 0617285
Nov. 24, 2011  (CN) .......................... 2011 1 0378158

(51) Int. Cl.
| | |
|---|---|
| *C07D 311/28* | (2006.01) |
| *C07D 417/04* | (2006.01) |
| *C07D 405/04* | (2006.01) |
| *C07D 407/04* | (2006.01) |
| *C07D 311/30* | (2006.01) |
| *C07D 311/54* | (2006.01) |
| *C07D 311/60* | (2006.01) |
| *C07D 311/76* | (2006.01) |
| *C07D 409/04* | (2006.01) |
| *C07D 413/04* | (2006.01) |

(52) U.S. Cl.
CPC ............ *C07D 311/28* (2013.01); *C07D 311/30* (2013.01); *C07D 311/54* (2013.01); *C07D 311/60* (2013.01); *C07D 311/76* (2013.01); *C07D 405/04* (2013.01); *C07D 407/04* (2013.01); *C07D 409/04* (2013.01); *C07D 413/04* (2013.01); *C07D 417/04* (2013.01)

(58) Field of Classification Search
CPC .. C07D 311/30; C07D 311/54; C07D 311/60; C07D 311/76; C07D 311/28; C07D 407/04; C07D 409/04; C07D 413/04; C07D 405/04
USPC ................... 549/403, 365, 300, 362; 548/204
See application file for complete search history.

(56) References Cited

FOREIGN PATENT DOCUMENTS

JP  09301915 A  11/1997

OTHER PUBLICATIONS

Tabopda, Turibio K., et al. "Triprenylated flavonoids from *Dorstenia psilurus* and their α-glucosidase inhibition properties." Journal of Natural Products 71 (12) (2008): 2068-2072.*
Jain, A. C., Constitution and synthesis of naturally occurring isopentenylated kaempferol derivatives, noranhydroicaritin and isoanhydroicaritin and related flavonolsincluding Di-O-methylicaritin. Australian Journal of Chemistry 28.3 (1975): 607-619.*
Meanwell, N.A., Synopsis of Some Recent Tactical Application of Bioisosteres in Drug Design, J. Med. Chem. 2011, 54, 2529-2591.*
Jain, A. C.,Synthesis of sericetin and related compounds, Current Science ,1973, 42(9), 314-15.*
Cerqueira, F., Inhibition of lymphocyte proliferation by prenylated flavones: Artelastin as a potent inhibitor, Life Sciences, 2003, 73, 2321-2334.*
J. Sambrook; "Molecular Cloning $3^{rd}$ Edition 3 Volumes" Cold Spring Harbor Laboratory Press, 2001; ISBN-10 0-87969-577-3; 13 978-0-87969-577-4.
A. Bahr, et al; *Homo sapiens* Mrna; Cdna DKFZp686N23123 (from clone DKFZp686N23123) The German cDNA Consortium Direct Submission, Sep. 22, 2004; 4 pages; http://www.ncbi.nlm.nih.gov/nuccore/BX640939.
Stephen M. Berge, et al; "Pharmaceutical Salts" Review Article Journal of Pharmaceutical Sciences, Jan. 1977; vol. 66, No. 1, pp. 1-19.
T. Higuchi et al; "Pro-drugs as Novel Drug Delivery Systems", A Symposium sponsored by the Division of Medicinal Chemistry at the $168^{th}$ Meeting of the American Chemical Society, Atlantic City, N.J., Sep. 10, 1974; 249 pages.
Gilles Flouriot, et al; "Identification of a new isoform of the human estrogen receptor-alpha (hER-α) that is encoded by distinct transcripts and that is able to repress hER-α activation function 1", The EMBO Journal, vol. 19, No.17, pp. 4688-4700; Sep. 1, 2000.
T.W. Greene, et al; Protective Groups in Organic Synthesis ($2^{nd}$ edition), 11 pages, Published 1991; Publisher John Wiley & Sons; ISBN: 0471623016.
Marc Lacroix et al; "Relevance of breast cancer cell lines as models for breast tumours: an update", Breast Cancer Research and Treatment, vol. 83, pp. 249-289; Feb. 2004.
Lei Li, et al; "Plasma membrane localization and function of the estrogen receptor α variant (ER46) in human endothelial cells", PNAS, Apr. 15, 2003, vol. 100, No. 8, pp. 4807-4812.
Bonaventure T. Ngadjui, et al; "Dorsilurins C, D and E, three prenylated flavonoids from the roots of *Dorstenia psilurus*", Phytochemistry, vol. 52, pp. 731-735, Oct. 1999.
Turibio K. Tobopda, et al; "Triprenylated Flavonoids from *Dorstenia psilurus* and Their α-Glucosidase Inhibition Properties", J. Nat Prod. vol. 71, Issue 12, pp. 2068-2072, Dec. 2008.
Zhaoyi Wang, et al; "A variant of estrogen receptor-α, hER-α36: Transduction of estrogen- and antiestrogen-dependent membrane-initiated mitogenic signaling", PNAS, Jun. 13, 2006, vol. 103, No. 24, pp. 9063-9068.

(Continued)

*Primary Examiner* — Noble Jarrell
*Assistant Examiner* — John Mauro
(74) *Attorney, Agent, or Firm* — LADAS & PARRY LLP

(57) ABSTRACT

The present invention provides a kind of benzopyrone compounds having a structure of formula (I) and the pharmaceutically acceptable salts or prodrugs thereof, and the pharmaceutical compositions containing such compounds, which can be used to regulate the novel estrogen receptor ER-a36, and prevent and/or treat the related diseases mediated by the ER-a36 receptor, such as cancers, etc.

4 Claims, 6 Drawing Sheets
(5 of 6 Drawing Sheet(s) Filed in Color)

(56) References Cited

OTHER PUBLICATIONS

Zhao Yi Wang, et al; "Identification, cloning and expression of human estrogen receptor-α36, a novel vaiant of human estrogen receptor-α66", Biochemical and Biophysical Research Communications, vol. 336, pp. 1023-1027; Available online Sep. 7, 2005.

International Search Report; mailed Mar. 29, 2012; PCT/CN2011/084321.

Kitaoka, Masahiro et al., "Prenyflavenoids: A New Class of Non-Steroidal Phytoestrogen (Part 1). Isolation of 8-Isopentenylnaringenin and Initial Study on its Structure-Activity Relationship", Planta Medica vol. 64, Feb. 1, 1998, pp. 511-515.

Pedro, Madalena et al., "Effects of natural Prenylated flavones in the phenotypical EE (+) MCF-7 and ER(−) MDA-MB-231 human breast cancer cells", Toxicology Letters vol. 164, Available Online Dec. 20, 2005, pp. 24-36.

Wang, Zhi-Qiang et al., "Prenylflavonoids as Nonsteroidal Phytoestrogens and Related Structure-Activity Relationships", ChemMedChem, Published online Feb. 24, 2006, pp. 482-488.

Ye, H.Y. et al., "Estrogenic effects of two derivatives of icariin on human breast cancer MCF-7 cells", Phytomedicine vol. 12, Oct. 27, 2004, pp. 735-741.

Extended European Search Report Appln. No. EP 11 85 3031; Dated Apr. 11, 2014.

Bonaventure T. Ngadjui, et al; "Dorsilurins C, D an E, three prenylated flavonoids from the roots of *Dorstenia psilurus*", Phytochemistry, vol. 52, Issue 4, pp. 731-735, Oct. 1999.

Turibio K. Tabopda, et al; "Triprenylated Flavonoids from *Dorstenia psilurus* and Their α-Glucosidase Inhibition Properties", Journal of Natural Products, Dec. 2008: vol. 71(12); pp. 2068-2072.

\* cited by examiner

BENZOPYRONE ESTROGEN RECEPTOR REGULATOR

TECHNICAL FIELD

The present invention relates to benzopyrone compounds, the salts, or the prodrugs thereof, pharmaceutical compositions comprising the compounds, and use of the compounds in preventing and/or treating the estrogen receptor related diseases.

BACKGROUND

Estrogens are a group of hormones that are involved in many critical physiological functions in the human body. Estrogens function to facilitate the development of the female sexual organs, preparing the breast and uterus for pregnancy and breast feeding after childbirth. Estrogens also play important roles in maintaining proper cardiovascular function and bone density. It is well-known that Estrogens can stimulate cell proliferation and hence may increase a risk of developing cancers for females, especially breast cancer and uterus cancer.

Estrogens regulate cell functions by binding to estrogen receptors in target cells. Two types of estrogen receptors (ERs), i.e., ER-α and ER-β, were found in human cells. ER-α and ER-β have similar protein structures, each of which possesses three independent but interacting functional domains: the N-terminal domain (A/B domain), the central DNA-binding domain (C domain), and the C-terminal ligand-binding domain (D/E/F domain). The N-terminal domain has a ligand-independent activation function (AF-1), which can interact with coactivators and transcriptionally activate the target genes in the absence of ligands. The DNA binding-domain plays important roles in the dimerization of receptors and binding to specific DNA sequence. The C-terminal ligand-binding domain may mediate ligand binding and has a ligand-dependent transcriptional activation function (AF-2), which may activate gene transcription in the presence of ligands.

The full-length ER-α was identified as a 66 kDa protein and referred to as ER-α66. ER-α66 contains all three function domains. A splice variant of ER-α66 was later discovered and named ER-α46. ER-α46 has a molecular weight of about 46 kDa and lacks the N-terminal AF-1 domain of ER-α66. Recently, a novel 36 kDa ER-α variant, ER-α36, was identified, which lacks the N-terminal AF-1 domain and the C-terminal AF-2 domain of ER-α66 (Wang et al., Biochem. Biophys. Res. Commun. 336, 1023-1027 (2005)).

ER-α66 is believed to mediate estrogen-stimulated cell proliferation via transcriptional activation of the target genes. Binding of estrogen to ER-α66 activates the transcriptional activation domain of ER-α66 to stimulate the expression of downstream target genes and eventually leads to cell proliferation. ER-α46 was proved to mediate membrane-initiated and estrogen-stimulated rapid NO synthesis (Li et al., Proc. Natl. Acad. Sci. USA 100:4807-4812 (2003)). It was also shown that ER-α46 lacking the AF-1 domain, inhibits the AF-1 activity of ER-α66 (Flouriot, G., EMBO, 19, 4688-4700, (2000)). Since ER-α36 lacks both the AF-1 and AF-2 transcriptional activation domains, it may act as a dominant-negative inhibitor to inhibit both AF-1 and AF-2 functions of ER-α and ER-β. In addition, ER-α36 is localized primarily on the cell membrane and mediates the membrane-initiated mitogenic estrogen signaling that stimulates cell proliferation. (Wang et al., Biochem. Biophys. Res. Commun. 336, 1023-1027 (2005)); Wang et al., Proc. Natl. Acad. Sci. U.S.A. 103: 9063-9068 (2006)).

Extensive studies have shown that estrogen signaling is mediated via the classic nucleus transcriptional activation pathways as well as the non-classic membrane-initiated signaling pathways. It seems that ER-α66 and ER-α46 function primarily in the nucleus while ER-α36 functions mainly outside of the nucleus.

It was also shown that ER-α36 lacks Helix 8-12 of the ligand-binding domain contained in the original ER-α66, which totally changes the ligand binding specificity of ER-α36. Thus, ER-α36 may bind to ligands different from those to which ER-α66 and ER-β bind.

As estrogen receptor related diseases continue to affect many individuals, there remains an urgent need to develop novel compounds and pharmaceutical compositions thereof useful for preventing and/or treating such diseases.

SUMMARY

The present invention provides a class of benzopyrone compounds shown as formula (I), the salts or the prodrugs thereof, and the pharmaceutical compositions comprising the compounds useful for regulating a new estrogen receptor ER-α36,

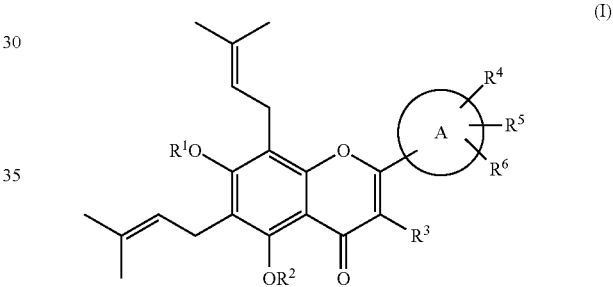

(I)

Wherein:
$R^1$ and $R^2$ are independently selected from the group consisting of hydrogen, ($C_1$-$C_6$)alkyl, ($C_2$-$C_6$)alkenyl, ($C_2$-$C_6$)alkynyl, formyl, ($C_1$-$C_6$)alkylcarbonyl, ($C_1$-$C_6$)alkoxycarbonyl, ($C_1$-$C_6$)alkyl substituted with one or more halogen atoms, $R^3$ is selected from the group consisting of hydrogen, hydroxy, ($C_1$-$C_6$)alkyl, ($C_1$-$C_6$)alkoxy, halogen, amino, ($C_1$-$C_6$)alkoxy substituted with one or more halogen atoms;

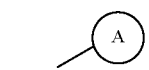

is selected from the group consisting of ($C_6$-$C_{10}$)aryl, 5-10 membered heteroaryl, ($C_3$-$C_8$)cycloalkyl, 3-8 membered heterocycloalkyl;

$R^4$, $R^5$ and $R^6$ are independently selected from the group consisting of hydrogen, halogen, hydroxy, hydroxy($C_1$-$C_6$)alkyl, amino, formyl, formamido, cyan, nitro, HO—(C=O)—, —$SO_3H$, ($C_1$-$C_6$)alkyl, ($C_1$-$C_6$)alkyl substituted with one or more halogen atoms, ($C_2$-$C_6$)alkenyl, ($C_2$-$C_6$)alkynyl, ($C_1$-$C_6$)alkoxy, ($C_1$-$C_6$)alkoxy substituted with one or more halogen atoms, ($C_2$-$C_6$)alkenoxy, ($C_1$-$C_6$)alkylcarbonyl, ($C_1$-$C_6$)alkoxycarbonyl, amino($C_1$-$C_6$)alkyl, N—($C_1$-$C_6$)alkylaminocarbonyl, N,N—[($C_1$-$C_6$)alkyl]$_2$aminocarbonyl, N—($C_6$-$C_{10}$)arylaminocarbonyl, N,N—[($C_6$-$C_{10}$)aryl]$_2$ aminocarbonyl, N—($C_1$-$C_6$)alkyl-N—($C_1$-$C_6$)alkylaminocarbonyl, N—($C_1$-$C_6$)alkyl-N—($C_6$-$C_{10}$)arylaminocarbonyl, N,N—[($C_1$-$C_6$)alkyl]$_2$amino, N—($C_1$-$C_6$)alkylamino, N—($C_6$-$C_{10}$)arylamino, N,N—[($C_6$-$C_{10}$)aryl]$_2$amino, N—($C_1$-$C_6$)alkyl-N—($C_1$-$C_6$)alkylamino, N—($C_1$-$C_6$) alkyl-N—($C_6$-$C_{10}$)arylamino, N,N—[($C_1$-$C_6$)alkylaryl]$_2$ amino, ($C_6$-$C_{10}$)aryl (comprising substituted aryl), ($C_6$-$C_{10}$) aryloxy, 5-10 membered heteroaryl (comprising substituted heteroaryl), 5-10 membered heteroaryloxy, aminosulfonyl, N—($C_1$-$C_6$)alkylaminosulfonyl, N,N—[($C_1$-$C_6$)alkyl]$_2$aminosulfonyl, morpholine sulfonyl, piperidine sulfonyl, piperazine sulfonyl, N-methylpiperazinesulfonyl, N-benzylpiperazinesulfonyl, pyrrolidinylsulfonyl, methylsulfonyl, trifluoromethylsulfonyl, trifluoromethylsulfinyl, p-tosyl, thiol, ($C_1$-$C_6$)alkylthio, ($C_1$-$C_6$)alkylthio substituted with one or more halogen atoms; or $R^4$ and $R^5$ are taken together to form —O($CH_2$)$_n$O—, n is 1-3;

When

is phenyl and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethoxy, CH=CH—C($CH_3$)$_2$— and isopentenyl.

BRIEF DESCRIPTION OF THE FIGURES

The file of this patent contains at least one drawing executed in color. Copies of this patent with color drawing(s) will be provided by the Office upon request and payment of the necessary fee.

DETAILED DESCRIPTION OF THE INVENTION

Compounds and Derivatives Thereof

Figure 1:
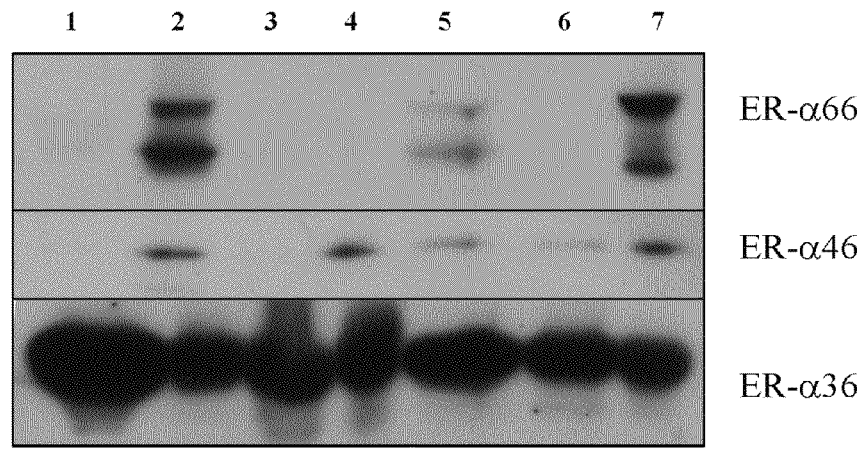
FIG. 1 shows Western blot results depicting the expression of ER-α66, ER-α46 and ER-α36 in human breast cancer samples. Lane 1: normal breast tissue; Lane 2: infiltrating ductal carcinoma; Lane 3: infiltrating ductal carcinoma; Lane 4: invasive ductal carcinoma; Lane 5: infiltrating lobular carcinoma; Lane 6: infiltrating lobular carcinoma; Lane 7: non-invasive ductal carcinoma.

In some embodiments of the present invention, benzopyrone compounds, the pharmaceutically acceptable salts, prodrugs thereof and the pharmaceutical compositions comprising the compounds are provided. They may be used to regulate the function of novel estrogen receptor ER-α36, prevent and/or treat the diseases mediated by ER-α36 receptor, such as cancer, etc.

In some embodiments, the present invention provides a compound of formula (I)

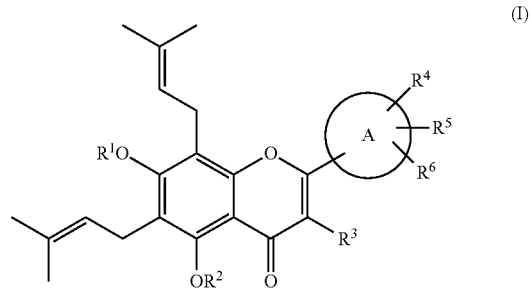

a pharmaceutical acceptable salt, prodrug, or pharmaceutical composition, wherein:

$R^1$ and $R^2$ are independently selected from the group consisting of hydrogen, $(C_1-C_6)$alkyl, $(C_2-C_6)$alkenyl, $(C_2-C_6)$alkynyl, formyl, $(C_1-C_6)$alkylcarbonyl, $(C_1-C_6)$alkoxycarbonyl, $(C_1-C_6)$alkyl substituted with one or more halogen atoms;

$R^3$ is selected from the group consisting of hydrogen, hydroxy, $(C_1-C_6)$alkyl, $(C_1-C_6)$alkoxy, halogen, amino, $(C_1-C_6)$alkoxy substituted with one or more halogen atoms,

is selected from the group consisting of $(C_{6-10})$aryl, 5-10 membered heteroaryl, $(C_3-C_8)$cycloalkyl, 3-8 membered heterocycloalkyl;

$R^4$, $R^5$ and $R^6$ are independently selected from the group consisting of hydrogen, halogen, hydroxy, hydroxy$(C_1-C_6)$alkyl, amino, formyl, formamido, cyan, nitro, HO—(C=O)—, —SO$_3$H, $(C_1-C_6)$alkyl, $(C_1-C_6)$alkyl substituted with one or more halogen atoms, $(C_2-C_6)$alkenyl, $(C_2-C_6)$alkynyl, $(C_1-C_6)$alkoxy, $(C_1-C_6)$alkoxy substituted with one or more halogen atoms, $(C_2-C_6)$alkenoxy, $(C_1-C_6)$alkylcarbonyl, $(C_1-C_6)$alkoxycarbonyl, amino$(C_1-C_6)$alkyl, N—$(C_1-C_6)$alkylaminocarbonyl, N,N—[$(C_1-C_6)$alkyl]$_2$aminocarbonyl, N—$(C_6-C_{10})$arylaminocarbonyl, N,N—[$(C_6-C_{10})$aryl]$_2$ aminocarbonyl, N—$(C_1-C_6)$alkyl-N—$(C_1-C_6)$alkylaminocarbonyl, N—$(C_1-C_6)$alkyl-N—$(C_6-C_{10})$arylaminocarbonyl, N,N—[$(C_1-C_6)$alkyl]$_2$amino, N—$(C_1-C_6)$alkylamino, N—$(C_6-C_{10})$arylamino, N,N—[$(C_6-C_{10})$aryl]$_2$amino, N—$(C_1-C_6)$alkyl-N—$(C_1-C_6)$alkylamino, N—$(C_1-C_6)$alkyl-N—$(C_6-C_{10})$arylamino, N,N—[$C_1-C_6$)alkylaryl]$_2$ amino, $(C_6-C_{10})$aryl (comprising substituted aryl), $(C_6-C_{10})$aryloxy, 5-6 membered heteroaryl (comprising substituted heteroaryl), 5-10 membered heteroaryloxy, aminosulfonyl, N—$(C_1-C_6)$alkylaminosulfonyl, N,N—[$(C_1-C_6)$alkyl]$_2$aminosulfonyl, morpholine sulfonyl, piperidine sulfonyl, piperazine sulfonyl, N-methylpiperazinesulfonyl, N-benzylpiperazinesulfonyl, pyrrolidinylsulfonyl, methylsulfonyl, trifluoromethylsulfonyl, trifluoromethylsulfinyl, p-tosyl, thiol, $(C_1-C_6)$alkylthio, $(C_1-C_6)$alkylthio substituted with one or more halogen atoms; or $R^4$ and $R^5$ are taken together to form —O(CH$_2$)$_n$O—, n is 1-3;

When

is phenyl and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethoxy, CH=CH—C(CH$_3$)$_2$— and isopentenyl.

In one embodiment, the present invention provides a compound of formula (II):

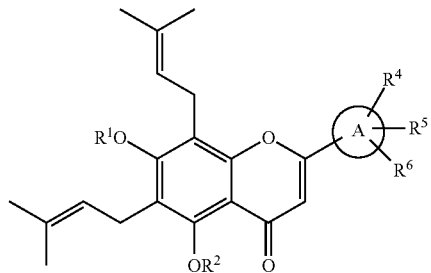

wherein:

$R^1$ and $R^2$ are selected from the group consisting of hydrogen, methyl, ethyl, formyl, acetyl;

is selected from the group consisting of phenyl, naphthyl, 5-6 membered heteroaryl, $(C_3-C_6)$cycloalkyl, 4-7 membered heterocycloalkyl;

$R^4$ and $R^5$ are independently selected from the group consisting of hydrogen, halogen, hydroxy, hydroxy$(C_1-C_6)$alkyl, amino, formyl, formamido, cyan, nitro, HO—(C=O)—, —SO$_3$H, $(C_1-C_6)$alkyl, trifluoromethyl, trifluoromethoxy, $(C_1-C_6)$alkoxy, $(C_1-C_6)$alkoxy substituted with one or more halogen atoms, $(C_1-C_6)$alkylcarbonyl, $(C_1-C_6)$alkoxycarbonyl, amino$(C_1-C_6)$alkyl, N—[$(C_1-C_3)$alkyl]aminocarbonyl, N,N—[$C_1-C_3$)alkyl]$_2$aminocarbonyl, N—[$(C_1-C_3)$alkyl]amino, N,N—[$(C_1-C_3)$alkyl]$_2$amino, aminosulfonyl, methylsulfonyl, trifluoromethylsulfonyl, trifluoromethylsulfinyl, thiol, $(C_1-C_3)$alkylthio, trifluoromethylthio, N—$(C_1-C_3)$alkylaminosulfonyl, N,N—[$C_1-C_3$)alkyl]$_2$aminosulfonyl, morpholine sulfonyl, piperidine sulfonyl, piperazine sulfonyl, N-methyl piperazinesulfonyl, N-benzylpiperazinesulfonyl, pyrrolidinylsulfonyl, tetrazolyl, triazolyl, 2-thiazolyl, 2-imidazolyl, 2-furyl, 5-imidazolyl, 5-methylimidazolyl; or $R^4$ and $R^5$ are taken together to form —O(CH$_2$)$_n$O—, n is 1-3;

$R^6$ is selected from the group consisting of hydrogen, halogen, hydroxy and amino;

when

is phenyl, and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethoxy, CH=CH—C(CH$_3$)$_2$— and isopentenyl.

In one embodiment, the present invention provides a compound of formula (III):

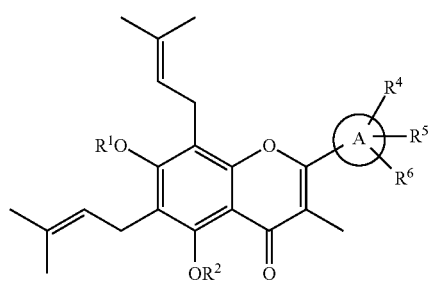

(III)

wherein:

$R^1$ and $R^2$ are independently selected from the group consisting of hydrogen, methyl, ethyl, formyl, acetyl;

is selected from the group consisting of phenyl, naphthyl, 5-6 membered heteroaryl, $(C_3-C_6)$cycloalkyl, 4-7 membered heterocycloalkyl;

$R^4$ and $R^5$ are independently selected from the group consisting of hydrogen, halogen, hydroxy, hydroxy$(C_1-C_6)$alkyl, amino, formamido, cyan, nitro, HO—(C=O)—, —SO$_3$H, $(C_1-C_6)$alkyl, trifluoromethyl, trifluoromethoxy, $(C_1-C_6)$alkoxy, $(C_1-C_6)$alkoxy substituted with one or more halogen atoms, $(C_1-C_6)$alkylcarbonyl, $(C_1-C_6)$alkoxycarbonyl, amino$(C_1-C_6)$alkyl, N—[$(C_1-C_3)$alkyl]aminocarbonyl, N,N—[$(C_1-C_3)$alkyl]$_2$aminocarbonyl, N—[$(C_1-C_3)$alkyl]amino, N,N—[$(C_1-C_3)$alkyl]$_2$amino, aminosulfonyl, methylsulfonyl, trifluoromethylsulfonyl, trifluoromethylsulfinyl, thiol, $(C_1-C_3)$alkylthio, trifluoromethylthio, N—$(C_1-C_3)$alkylaminosulfonyl, N,N—[$(C_1-C_3)$alkyl]$_2$aminosulfonyl, morpholine sulfonyl, piperidine sulfonyl, piperazine sulfonyl, N-methyl piperazinesulfonyl, N-benzylpiperazinesulfonyl, pyrrolidinylsulfonyl, tetrazolyl, triazolyl, 2-thiazolyl, 2-imidazolyl, 2-furyl, 5-imidazolyl, 5-methylimidazolyl; or $R^4$ and $R^5$ are taken together to form —O(CH$_2$)$_n$O—, n is 1-3;

$R^6$ is selected from the group consisting of hydrogen, halogen, hydroxyl and amino;

when

is phenyl, and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethyoxy, CH=CH—C(CH$_3$)$_2$— and isopentenyl.

In one embodiment, the present invention provides a compound of formula (IV):

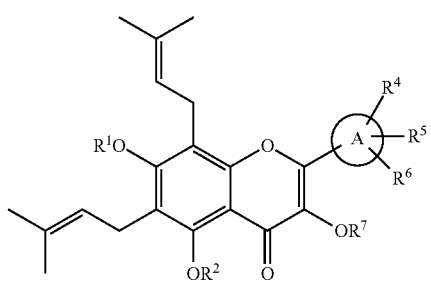

(IV)

wherein:

$R^1$ and $R^2$ are independently selected from the group consisting of hydrogen, methyl, ethyl, formyl, acetyl;

is selected from the group consisting of phenyl, naphthyl, 5-6 membered heteroaryl, $(C_3-C_6)$cycloalkyl, 4-7 membered heterocycloalkyl;

$R^4$ and $R^5$ are independently selected from the group consisting of hydrogen, halogen, hydroxy, hydroxy$(C_1-C_6)$alkyl, amino, formyl, formamido, cyan, nitro, HO—(C=O)—, —SO$_3$H, $(C_1-C_6)$alkyl, trifluoromethyl, trifluoromethoxy, $(C_1-C_6)$alkoxy, $(C_1-C_6)$alkoxy substituted with one or more halogen atoms, $(C_1-C_6)$alkylcarbonyl, $(C_1-C_6)$alkoxycarbonyl, amino$(C_1-C_6)$alkyl, N—[$(C_1-C_3)$alkyl]aminocarbonyl, N,N—[$(C_1-C_3)$alkyl]$_2$aminocarbonyl, N—[$(C_1-C_3)$alkyl]amino, N,N—[$(C_1-C_3)$alkyl]$_2$amino, aminosulfonyl, methyl sulfonyl, trifluoromethylsulfonyl, trifluoromethylsulfinyl, thiol, $(C_1-C_3)$alkylthio, trifluoromethylthio, N—$(C_1-C_3)$alkylaminosulfonyl, N,N—[$(C_1-C_3)$alkyl]$_2$aminosulfonyl, morpholine sulfonyl, piperidine sulfonyl, piperazine sulfonyl, N-methyl piperazinesulfonyl, N-benzylpiperazinesulfonyl, pyrrolidinylsulfonyl, tetrazolyl, triazolyl, 2-thiazolyl, 2-imidazolyl, 2-furyl, 5-imidazolyl, 5-methylimidazolyl; or $R^4$ and $R^5$ are taken together to form —O(CH$_2$)$_n$O—, n is 1-3;

$R^6$ is selected from the group consisting of hydrogen, halogen, hydroxy and amino;

$R^7$ is selected from the group consisting of hydrogen, $(C_1-C_6)$alkyl, $(C_1-C_6)$alkoxy substituted with one or more halogen atoms;

when

is phenyl, and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethyoxy, CH=CH—C(CH$_3$)$_2$— and isopentenyl.

In one embodiment, the present invention provides a compound of formula (V):

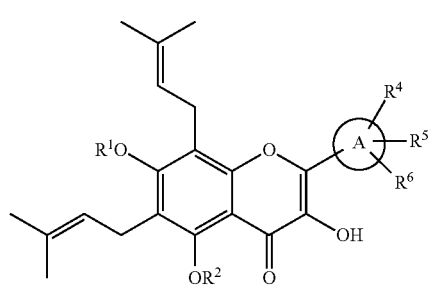

wherein:

$R^1$ and $R^2$ are independently selected from the group consisting of hydrogen, methyl, ethyl, formyl, acetyl;

is selected from the group consisting of phenyl, naphthyl, 5-6 membered heteroaryl, $(C_3-C_6)$cycloalkyl, 4-7 membered heterocycloalkyl;

$R^4$ and $R^5$ are independently selected from the group consisting of hydrogen, halogen, hydroxy, hydroxy$(C_1-C_6)$alkyl, amino, amino$(C_1-C_6)$alkyl, N—[$(C_1-C_3)$alkyl]aminocarbonyl, N,N—[$(C_1-C_3)$alkyl]$_2$aminocarbonyl, N—[$(C_1-C_3)$alkyl]amino, N,N—[$(C_1-C_3)$alkyl]$_2$amino, formyl, formamido, cyan, nitro, HO—(C=O)—, —SO$_3$H, $(C_1-C_6)$alkyl, trifluoromethyl, trifluoromethoxy, $(C_1-C_6)$alkoxy, $(C_1-C_6)$alkylcarbonyl, $(C_1-C_6)$alkoxy substituted with one or more halogen atoms, $(C_1-C_6)$alkoxycarbonyl, aminosulfonyl, methylsulfonyl, trifluoromethylsulfonyl, trifluoromethylsulfinyl, thiol, $(C_1-C_3)$alkylthio, trifluoromethylthio, N—$(C_1-C_3)$alkylaminosulfonyl, N,N—[$C_1-C_3)$alkyl]$_2$aminosulfonyl, morpholine sulfonyl, piperidine sulfonyl, piperazine sulfonyl, N-methyl piperazinesulfonyl, N-benzylpiperazinesulfonyl, pyrrolidinylsulfonyl, tetrazolyl, triazolyl, 2-thiazolyl, 2-imidazolyl, 2-furyl, 5-imidazolyl, 5-methylimidazolyl; or $R^4$ and $R^5$ are taken together to form —O(CH$_2$)$_n$O—, n is 1-3;

$R^6$ is selected from the group consisting of hydrogen, halogen, hydroxy and amino;

when

is phenyl, and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethyoxy, CH=CH—C(CH$_3$)$_2$— and isopentenyl.

In one embodiment, the present invention provides a compound of formula (VI):

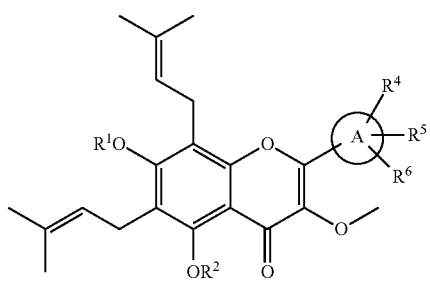

wherein:

$R^1$ and $R^2$ are independently selected from the group consisting of hydrogen, methyl, ethyl, formyl, acetyl;

is selected from the group consisting of phenyl, naphthyl, 5-6 membered heteroaryl, $(C_3-C_6)$cycloalkyl, 4-7 membered heterocycloalkyl;

$R^4$ and $R^5$ are independently selected from the group consisting of hydrogen, halogen, hydroxy, hydroxy$(C_1-C_6)$alkyl, amino, amino$(C_1-C_6)$alkyl, N—[$(C_1-C_3)$alkyl]aminocarbonyl, N,N—[$(C_1-C_3)$alkyl]$_2$aminocarbonyl, N—[$C_1-C_3$)alkyl]amino, N,N—[$(C_1-C_3)$alkyl]$_2$amino, formyl, formamido, cyan, nitro, HO—(C=O)—, —SO$_3$H, $(C_1-C_6)$alkyl, trifluoromethyl, trifluoromethoxy, $(C_1-C_6)$alkoxy, $(C_1-C_6)$alkylcarbonyl, $(C_1-C_6)$alkoxy substituted with one or more halogen atoms, $(C_1-C_6)$alkoxycarbonyl, aminosulfonyl, methylsulfonyl, trifluoromethylsulfonyl, trifluoromethylsulfinyl, thiol, $(C_1-C_3)$alkylthio, trifluoromethylthio, N—$(C_1-C_3)$alkylaminosulfonyl, N,N—[$C_1-C_3)$alkyl]$_2$aminosulfonyl, morpholine sulfonyl, piperidine sulfonyl, piperazine sulfonyl, N-methyl piperazinesulfonyl, N-benzylpiperazinesulfonyl, pyrrolidinylsulfonyl, tetrazolyl, triazolyl, 2-thiazolyl, 2-imidazolyl, 2-furyl, 5-imidazolyl, 5-methylimidazolyl; or $R^4$ and $R^5$ are taken together to form —O(CH$_2$)$_n$O—, n is 1-3;

$R^6$ is selected from the group consisting of hydrogen, halogen, hydroxy and amino;

when

is phenyl, and $R^6$ is hydrogen, if one of $R^4$ and $R^5$ is selected from the group consisting of hydrogen, hydroxy and methoxy, the other is not selected from the group consisting of hydrogen, hydroxy, methyl, methoxy, ethyoxy, CH=CH—C(CH$_3$)$_2$— and isopentenyl.

The especially preferred compounds of formula (I) include but are not limited to the following compounds:

2-(3-fluoro-4-methoxyphenyl)-5,7-dihydroxy-3-methoxy-6,8-di(3-methyl-2-buten-1-yl)-4H-benzopyran-4-one;

2-(3,5-difluorophenyl)-5,7-dihydroxy-3-methoxy-6,8-di(3-methyl-2-buten-1-yl)-4H-benzopyran-4-one;

2-(3-fluorophenyl)-5,7-dihydroxy-3-methoxy-6,8-di(3-methyl-2-buten-1-yl)-4H-benzopyran-4-one;
2-(3,4-difluorophenyl)-5,7-dihydroxy-3-methoxy-6,8-di(3-methyl-2-buten-1-yl)-4H-benzopyran-4-one;
2-(3-fluoro-4-chlorophenyl)-5,7-dihydroxy-3-methoxy-6,8-di(3-methyl-2-buten-1-yl)-4H-benzopyran-4-one;
2-(3-fluoro-4-trifluoromethylphenyl)-5,7-dihydroxy-3-methoxy-6,8-di(3-methyl-2-buten-1-yl)-4H-benzopyran-4-one;
2-(4-fluorophenyl)-5,7-dihydroxy-3-methoxy-6,8-di(3-methyl-2-buten-1-yl)-4H-benzopyran-4-one;
2-(3-chloro-4-fluorophenyl)-5,7-dihydroxy-3-methoxy-6,8-di(3-methyl-2-buten-1-yl)-4H-benzopyran-4-one;
2-(4-fluoro-3-methoxyphenyl)-5,7-dihydroxy-3-methoxy-6,8-di(3-methyl-2-buten-1-yl)-4H-benzopyran-4-one;
2-(4-chlorophenyl)-5,7-dihydroxy-3-methoxy-6,8-di(3-methyl-2-buten-1-yl)-4H-benzopyran-4-one;
2-(4-chloro-3-methylphenyl)-5,7-dihydroxy-3-methoxy-6,8-di(3-methyl-2-buten-1-yl)-4H-benzopyran-4-one;
2-(3,4-dichlorophenyl)-5,7-dihydroxy-3-methoxy-6,8-di(3-methyl-2-buten-1-yl)-4H-benzopyran-4-one;
2-(4-chloro-3-trifluoromethylphenyl)-5,7-dihydroxy-3-methoxy-6,8-di(3-methyl-2-buten-1-yl)-4H-benzopyran-4-one;
2-(2-fluoro-4-chlorophenyl)-5,7-dihydroxy-3-methoxy-6,8-di(3-methyl-2-buten-1-yl)-4H-benzopyran-4-one;
2-(4-trifluoromethylphenyl)-5,7-dihydroxy-3-methoxy-6,8-di(3-methyl-2-buten-1-yl)-4H-benzopyran-4-one;
2-(4-methylphenyl)-5,7-dihydroxy-3-methoxy-6,8-di(3-methyl-2-buten-1-yl)-4H-benzopyran-4-one;
2-(4-isopropylphenyl)-5,7-dihydroxy-3-methoxy-6,8-di(3-methyl-2-buten-1-yl)-4H-benzopyran-4-one;
2-(quinoxalin-6-yl)-5,7-dihydroxy-3-methoxy-6,8-di(3-methyl-2-buten-1-yl)-4H-benzopyran-4-one;
2-(naphthalen-2-yl)-5,7-dihydroxy-3-methoxy-6,8-di(3-methyl-2-buten-1-yl)-4H-benzopyran-4-one;
2-(2,3-dihydrogenbenzo[b][1,4]dioxan-6-yl)-5,7-dihydroxy-3-methoxy-6,8-di(3-methyl-2-buten-1-yl)-4H-benzopyran-4-one;
2-(benzo[d][1,3]dioxo-5-yl)-5,7-dihydroxy-3-methoxy-6,8-di(3-methyl-2-buten-1-yl)-4H-benzopyran-4-one;
2-(3-chloro-4-methoxyphenyl)-5,7-dihydroxy-3-methoxy-6,8-di(3-methyl-2-buten-1-yl)-4H-benzopyran-4-one;
2-(3-fluoro-4-ethoxyphenyl)-5,7-dihydroxy-3-methoxy-6,8-di(3-methyl-2-buten-1-yl)-4H-benzopyran-4-one;
2-(4-ethoxyphenyl)-5,7-dihydroxy-3-methoxy-6,8-di(3-methyl-2-buten-1-yl)-4H-benzopyran-4-one;
2-(thiazol-5-yl)-5,7-dihydroxy-3-methoxy-6,8-di(3-methyl-2-buten-1-yl)-4H-benzopyran-4-one;
2-(6-methoxypyridin-3-yl)-5,7-dihydroxy-3-methoxy-6,8-di(3-methyl-2-buten-1-yl)-4H-benzopyran-4-one;
2-(2-methoxypyridin-4-yl)-5,7-dihydroxy-3-methoxy-6,8-di(3-methyl-2-buten-1-yl)-4H-benzopyran-4-one;
2-(pyridin-3-yl)-5,7-dihydroxy-3-methoxy-6,8-di(3-methyl-2-buten-1-yl)-4H-benzopyran-4-one;
2-(pyridin-2-yl)-5,7-dihydroxy-3-methoxy-6,8-di(3-methyl-2-buten-1-yl)-4H-benzopyran-4-one;
2-(piperazin-2-yl)-5,7-dihydroxy-3-methoxy-6,8-di(3-methyl-2-buten-1-yl)-4H-benzopyran-4-one;
2-(pyridin-4-yl)-5,7-dihydroxy-3-methoxy-6,8-di(3-methyl-2-buten-1-yl)-4H-benzopyran-4-one;
2-(pyrimidin-5-yl)-5,7-dihydroxy-3-methoxy-6,8-di(3-methyl-2-buten-1-yl)-4H-benzopyran-4-one;
2-(pyrimidin-2-yl)-5,7-dihydroxy-3-methoxy-6,8-di(3-methyl-2-buten-1-yl)-4H-benzopyran-4-one;
2-cyclopropyl-5,7-dihydroxy-3-methoxy-6,8-di(3-methyl-2-buten-1-yl)-4H-benzopyran-4-one;
2-cyclobutyl-5,7-dihydroxy-3-methoxy-6,8-di(3-methyl-2-buten-1-yl)-4H-benzopyran-4-one;
2-cyclopentyl-5,7-dihydroxy-3-methoxy-6,8-di(3-methyl-2-buten-1-yl)-4H-benzopyran-4-one;
2-cyclohexyl-5,7-dihydroxy-3-methoxy-6,8-di(3-methyl-2-buten-1-yl)-4H-benzopyran-4-one;
2-(tetrahydrofuran-3-yl)-5,7-dihydroxy-3-methoxy-6,8-di(3-methyl-2-buten-1-yl)-4H-benzopyran-4-one;
2-(thiophen-2-yl)-5,7-dihydroxy-3-methoxy-6,8-di(3-methyl-2-buten-1-yl)-4H-benzopyran-4-one;
2-(thiophen-3-yl)-5,7-dihydroxy-3-methoxy-6,8-di(3-methyl-2-buten-1-yl)-4H-benzopyran-4-one;
2-(furan-2-yl)-5,7-dihydroxy-3-methoxy-6,8-di(3-methyl-2-buten-1-yl)-4H-benzopyran-4-one;
2-(furan-3-yl)-5,7-dihydroxy-3-methoxy-6,8-di(3-methyl-2-buten-1-yl)-4H-benzopyran-4-one;
2-(thiazol-4-yl)-5,7-dihydroxy-3-methoxy-6,8-di(3-methyl-2-buten-1-yl)-4H-benzopyran-4-one;
2-(thiazol-5-yl)-5,7-dihydroxy-3-methoxy-6,8-di(3-methyl-2-buten-1-yl)-4H-benzopyran-4-one;
2-(oxazol-4-yl)-5,7-dihydroxy-3-methoxy-6,8-di(3-methyl-2-buten-1-yl)-4H-benzopyran-4-one;
2-(1-methyl-1H-pyrazol-5-yl)-5,7-dihydroxy-3-methoxy-6,8-di(3-methyl-2-buten-1-yl)-4H-benzopyran-4-one;
2-(1-methyl-1H-pyrazol-2-yl)-5,7-dihydroxy-3-methoxy-6,8-di(3-methyl-2-buten-1-yl)-4H-benzopyran-4-one;
2-(1-methyl-1H-imidazol-2-yl)-5,7-dihydroxy-3-methoxy-6,8-di(3-methyl-2-buten-1-yl)-4H-benzopyran-4-one;
2-(1-methyl-1H-pyrazol-5-yl)-5,7-dihydroxy-3-methoxy-6,8-di(3-methyl-2-buten-1-yl)-4H-benzopyran-4-one;
2-(1-benzo[b]thiazol-2-yl)-5,7-dihydroxy-3-methoxy-6,8-di(3-methyl-2-buten-1-yl)-4H-benzopyran-4-one;
2-(benzofuran-2-yl)-5,7-dihydroxy-3-methoxy-6,8-di(3-methyl-2-buten-1-yl)-4H-benzopyran-4-one;
2-(2-fluoropyridin-4-yl)-5,7-dihydroxy-3-methoxy-6,8-di(3-methyl-2-buten-1-yl)-4H-benzopyran-4-one;
2-(6-chloropyridin-3-yl)-5,7-dihydroxy-3-methoxy-6,8-di(3-methyl-2-buten-1-yl)-4H-benzopyran-4-one;
2-(5-chloropyridin-2-yl)-5,7-dihydroxy-3-methoxy-6,8-di(3-methyl-2-buten-1-yl)-4H-benzopyran-4-one;
2-(6-fluoropyridin-3-yl)-5,7-dihydroxy-3-methoxy-6,8-di(3-methyl-2-buten-1-yl)-4H-benzopyran-4-one;
2-(2-chloropyridin-4-yl)-5,7-dihydroxy-3-methoxy-6,8-di(3-methyl-2-buten-1-yl)-4H-benzopyran-4-one;
4-[5,7-dihydroxy-3-methoxy-6,8-di(3-methyl-2-butenyl)-4-oxo-4H-benzopyran-2-yl]benzoic acid;
4-[5,7-dihydroxy-3-methoxy-6,8-di(3-methyl-2-butenyl)-4-oxo-4H-benzopyran-2-yl]benzonitrile;
2-(4-trifluoromethoxyphenyl)-5,7-dihydroxy-3-methoxy-6,8-di(3-methyl-2-buten-1-yl)-4H-benzopyran-4-one:
2-(4-dimethylaminophenyl)-5,7-di hydroxy-3-methoxy-6,8-di(3-methyl-2-buten-1-yl)-4H-benzopyran-4-one;
4-[5,7-dihydroxy-3-methoxy-6,8-di(3-methyl-2-butenyl)-4-oxo-4H-benzopyran-2-yl]benzamide;
2-(4-difluoromethoxyphenyl)-5,7-dihydroxy-3-methoxy-6,8-di(3-methyl-2-buten-1-yl)-4H-benzopyran-4-one;
4-[5,7-dihydroxy-3-methoxy-6,8-di(3-methyl-2-butenyl)-4-oxo-4H-benzopyran-2-yl]benzenesulfonic acid;
4-[5,7-dihydroxy-3-methoxy-6,8-di(3-methyl-2-butylene1-yl)-4-oxo-4H-benzopyran-2-yl]benzene sulfonamide;
2-(4-methylsulfonylphenyl)-5,7-dihydroxy-3-methoxy-6,8-di(3-methyl-2-buten-1-yl)-4H-benzopyran-4-one;
2-(4-acetylphenyl)-5,7-dihydroxy-3-methoxy-6,8-di(3-methyl-2-buten-1-yl)-4H-benzopyran-4-one;
2-[4-(2-hydroxypropan-2-yl)phenyl]-5,7-dihydroxy-3-methoxy-6,8-di(3-methyl-2-buten-1-yl)-4H-benzopyran-4-one;

2-[4-(1-hydroxyethyl)phenyl]-5,7-dihydroxy-3-methoxy-6,8-di(3-methyl-2-buten-1-yl)-4H-benzopyran-4-one;
2-(4-methylphenyl)-5,7-dihydroxy-6,8-di(3-methyl-2-buten-1-yl)-4H-benzopyran-4-one;
2-(3,4-dichlorophenyl)-5,7-dihydroxy-6,8-di(3-methyl-2-buten-1-yl)-4H-benzopyran-4-one;
2-(4-fluorophenyl)-5,7-dihydroxy-6,8-di(3-methyl-2-buten-1-yl)-4H-benzopyran-4-one;
2-(3-chloro-4-methoxyphenyl)-5,7-dihydroxy-6,8-di(3-methyl-2-buten-1-yl)-4H-benzopyran-4-one;
2-(4-chlorophenyl)-5,7-dihydroxy-6,8-di(3-methyl-2-buten-1-yl)-4H-benzopyran-4-one;
2-(pyridin-3-yl)-5,7-dihydroxy-6,8-di(3-methyl-2-buten-1-yl)-4H-benzopyran-4-one;
2-(3,4-difluorophenyl)-5,7-dihydroxy-6,8-di(3-methyl-2-buten-1-yl)-4H-benzopyran-4-one;
2-(3,4-difluorophenyl)-3-methyl-5,7-dihydroxy-6,8-di(3-methyl-2-buten-1-yl)-4H-benzopyran-4-one;
2-(3,4-difluorophenyl)-3,5,7-trihydroxy-6,8-di(3-methyl-2-buten-1-yl)-4H-benzopyran-4-one;
2-(3-fluoro-4-chlorophenyl)-5,7-dihydroxy-6,8-di(3-methyl-2-buten-1-yl)-4H-benzopyran-4-one;
2-(3-fluoro-4-chlorophenyl)-3-methyl-5,7-dihydroxy-6,8-di(3-methyl-2-buten-1-yl)-4H-benzopyran-4-one;
2-(3-fluoro-4-chlorophenyl)-3,5,7-trihydroxy-6,8-di(3-methyl-2-buten-1-yl)-4H-benzopyran-4-one;
2-(3,4-difluorophenyl)-5-hydroxy-3,7-dimethoxy-6,8-di(3-methyl-2-buten-1-yl)-4H-benzopyran-4-one;
2-(3,4-difluorophenyl)-7-hydroxy-3,5-dimethoxy-6,8-di(3-methyl-2-buten-1-yl)-4H-benzopyran-4-one;
2-(3,4-difluorophenyl)-3,5,7-trimethoxy-6,8-di(3-methyl-2-buten-1-yl)-4H-benzopyran-4-one;
2-(3-fluoro-4-chlorophenyl)-5-hydroxy-3,7-dimethoxy-6,8-di(3-methyl-2-buten-1-yl)-4H-benzopyran-4-one;
2-(3-fluoro-4-chlorophenyl)-7-hydroxy-3,5-dimethoxy-6,8-di(3-methyl-2-buten-1-yl)-4H-benzopyran-4-one;
2-(3-fluoro-4-chlorophenyl)-3,5,7-trimethoxy-6,8-di(3-methyl-2-buten-1-yl)-4H-benzopyran-4-one;
2-(4-fluorophenyl)-3,5,7-trihydroxy-6,8-di(3-methyl-2-buten-1-yl)-4H-benzopyran-4-one;
2-(4-trifluoromethylphenyl)-3,5,7-trihydroxy-6,8-di(3-methyl-2-buten-1-yl)-4H-benzopyran-4-one;
2-(4-aminophenyl)-5,7-dihydroxy-3-methoxy-6,8-di(3-methyl-2-buten-1-yl)-4H-benzopyran-4-one;
4-[5,7-dihydroxy-3-methoxy-6,8-di(3-methyl-2-buten-1-yl)-4-oxo-4H-benzopyran-2-yl]-N,N-dimethylbenzene sulfonamide;
4-[5,7-dihydroxy-3-methoxy-6,8-di(3-methyl-2-buten-1-yl)-4-oxo-4H-benzopyran-2-yl]-N-methylbenzene sulfonamide;
2-[4-(trifluoromethylsulfonyl)phenyl]-5,7-dihydroxy-3-methoxy-6,8-di(3-methyl-2-buten-1-yl)-4H-benzopyran-4-one;
2-[4-(trifluoromethylsulfinyl)phenyl]-5,7-dihydroxy-3-methoxy-6,8-di(3-methyl-2-buten-1-yl)-4H-benzopyran-4-one;
2-[4-methylthiophenyl]-5,7-dihydroxy-3-methoxy-6,8-di(3-methyl-2-buten-1-yl)-4H-benzopyran-4-one;
2-[4-trifluoromethylthiophenyl]-5,7-dihydroxy-3-methoxy-6,8-di(3-methyl-2-buten-1-yl)-4H-benzopyran-4-one;
4-[5,7-dihydroxy-3-methoxy-6,8-di(3-methyl-2-buten-1-yl)-4-oxo-4H-benzopyran-2-yl]-methyl benzoate;
4-[5,7-dihydroxy-3-methoxy-6,8-di(3-methyl-2-buten-1-yl)-4-oxo-4H-benzopyran-2-yl]-ethylbenzoate;
2-[4-(2H-tetrazol-5-yl)phenyl]-5,7-dihydroxy-3-methoxy-6,8-di(3-methyl-2-buten-1-yl)-4H-benzopyran-4-one;
2-[4-(2-methyl-2H-tetrazol-5-yl)phenyl]-5,7-dihydroxy-3-methoxy-6,8-di(3-methyl-2-buten-1-yl)-4H-benzopyran-4-one;
2-[4-(1H-1,2,4-triazol-1-yl)phenyl]-5,7-dihydroxy-3-methoxy-6,8-di(3-methyl-2-buten-1-yl)-4H-benzopyran-4-one;
2-(3,5-dichlorophenyl)-5,7-dihydroxy-3-methoxy-6,8-di(3-methyl-2-buten-1-yl)-4H-benzopyran-4-one;
2-(4-nitro-3-fluoromethylphenyl)-5,7-dihydroxy-3-methoxy-6,8-di(3-methyl-2-buten-1-yl)-4H-benzopyran-4-one;
2-(3,4,5-trihydroxyphenyl)-5,7-dihydroxy-3-methoxy-6,8-di(3-methyl-2-buten-1-yl)-4H-benzopyran-4-one;
2-(3-methyl-4-hydroxyphenyl)-5,7-dihydroxy-3-methoxy-6,8-di(3-methyl-2-buten-1-yl)-4H-benzopyran-4-one;
2-(3-chloro-4-hydroxyphenyl)-5,7-dihydroxy-3-methoxy-6,8-di(3-methyl-2-buten-1-yl)-4H-benzopyran-4-one;
2-(3-trifluoromethyl-4-hydroxyphenyl)-5,7-dihydroxy-3-methoxy-6,8-di(3-methyl-2-buten-1-yl)-4H-benzopyran-4-one;
2-(3-hydroxy-4-trifluoromethylphenyl)-5,7-dihydroxy-3-methoxy-6,8-di(3-methyl-2-buten-1-yl)-4H-benzopyran-4-one;
2-(3-hydroxy-4-fluorophenyl)-5,7-dihydroxy-3-methoxy-6,8-di(3-methyl-2-buten-1-yl)-4H-benzopyran-4-one;
2-(3-fluoro-4-hydroxyphenyl)-5,7-dihydroxy-3-methoxy-6,8-di(3-methyl-2-buten-1-yl)-4H-benzopyran-4-one;
2-[4-(morpholinesulfonyl)phenyl]-5,7-dihydroxy-3-methoxy-6,8-di(3-methyl-2-buten-1-yl)-4H-benzopyran-4-one;
2-[4-(piperidin-1-yl-sulfonyl)phenyl]-5,7-dihydroxy-3-methoxy-6,8-di(3-methyl-2-buten-1-yl)-4H-benzopyran-4-one;
2-[4-(piperazin-1-yl-sulfonyl)phenyl)]-5,7-dihydroxy-3-methoxy-6,8-di(3-methyl-2-buten-1-yl)-4H-benzopyran-4-one;
2-[4-(4-methylpiperazin-1-yl-sulfonyl)phenyl]-5,7-dihydroxy-3-methoxy-6,8-di(3-methyl-2-buten-1-yl)-4H-benzopyran-4-one;
2-[4-(4-benzylpiperazin-1-ylsulfonyl)phenyl)-5,7-dihydroxy-3-methoxy-6,8-di(3-methyl-2-buten-1-yl)-4H-benzopyran-4-one;
2-[4-(2-hydroxyethyl)phenyl]-5,7-dihydroxy-3-methoxy-6,8-di(3-methyl-2-buten-1-yl)-4H-benzopyran-4-one;
2-[4-(2-aminoethyl)phenyl]-5,7-dihydroxy-3-methoxy-6,8-di(3-methyl-2-buten-1-yl)-4H-benzopyran-4-one;
2-(4-cyanophenyl)-3,5,7-trihydroxy-6,8-di(3-methyl-2-buten-1-yl)-4H-benzopyran-4-one;
2-(4-chlorophenyl)-3,5,7-trihydroxy-6,8-di(3-methyl-2-buten-1-yl)-4H-benzopyran-4-one;
2-(3,4-dichlorophenyl)-3,5,7-trihydroxy-6,8-di(3-methyl-2-buten-1-yl)-4H-benzopyran-4-one;
2-(3,5-dichlorophenyl)-3,5,7-trihydroxy-6,8-di(3-methyl-2-buten-1-yl)-4H-benzopyran-4-one;
4-[(3,5,7-trihydroxy-6,8-di(3-methyl-2-buten-1-yl)-4-oxo-4H-benzopyran-2-yl]benzoic acid;
4-[3,5,7-trihydroxy-6,8-di(3-methyl-2-buten-1-yl)-4-oxo-4H-benzopyran-2-yl]benzenesulfonic acid;
4-[3,5,7-trihydroxy-6,8-di(3-methyl-2-buten-1-yl)-4-oxo-4H-benzopyran-2-yl]benzamide;
4-[3,5,7-trihydroxy-6,8-di(3-methyl-2-buten-1-yl)-4-oxo-4H-benzopyran-2-yl]benzene sulfonamide;
4-[3,5,7-trihydroxy-6,8-di(3-methyl-2-buten-1-yl)-4-oxo-4H-benzopyran-2-yl]-N-methylbenzenesulfonamide;
4-[3,5,7-trihydroxy-6,8-di(3-methyl-2-buten-1-yl)-4-oxo-4H-benzopyran-2-yl]-N,N-dimethylbenzene sulfonamide;

2-(4-aminophenyl)-3,5,7-trihydroxy-6,8-di(3-methyl-2-buten-1-yl)-4H-benzopyran-4-one;
2-(4-dimethylaminophenyl)-3,5,7-trihydroxy-6,8-di(3-methyl-2-buten-1-yl)-4H-benzopyran-4-one;
2-(4-(trifluoromethylsulfonyl)phenyl)-3,5,7-trimethoxy-6,8-di(3-methyl-2-buten-1-yl)-4H-benzopyran-4-one;
2-[4-(2-methyl-2H-tetrazol-5-yl)-phenyl]-3,5,7-trihydroxy-6,8-di(3-methyl-2-buten-1-yl)-4H-benzopyran-4-one;
2-[4-(1H-1,2,4-triazol-1-yl)-phenyl]-3,5,7-trihydroxy-6,8-di(3-methyl-2-buten-1-yl)-4H-benzopyran-4-one;
2-[4-methoxyphenyl]-3-difluoromethoxy-5,7-dihydroxy-6,8-di(3-methyl-2-buten-1-yl)-4H-benzopyran-4-one;
2-[4-methoxyphenyl]-3-trifluoromethoxy-5,7-dihydroxy-6,8-di(3-methyl-2-buten-1-yl)-4H-benzopyran-4-one.

The compounds and the derivates thereof are named in accordance with the naming system of IUPAC (International Union of Pure and Applied Chemistry) or CAS (Chemical Abstract Service, Columbus, Ohio)

The definitions of the terms used in the present invention are described as follows. Unless otherwise indicated, the initial definition of a group or a term is applicable to said group or term throughout the description, regardless of the group alone or as a moiety of other groups.

The term "substituted", as used herein, means that a hydrogen atom in a molecule has been replaced with a different atom or molecule. The atom or molecule replacing the hydrogen atom is called "substituent".

The minimum and maximum content of carbon atom of a CnHn— is denoted with a prefix. For example, the prefix $(C_a-C_b)$alkyl means any alkyl having from "a" to "b" carbon atoms. Thus, for example, $(C_1-C_6)$alkyl means an alkyl having 1-6 carbon atoms.

The term "alkoxy", as used herein, means a linear or branched monovalent saturated aliphatic chain linked to an oxygen atom, including but not limited to methoxy, ethoxy, propoxy, butoxy, iso-butoxy, tert-butoxy and the like.

The term "alkyl", as used herein, means a straight or branched, monovalent, saturated aliphatic chain, comprising but not limited to the group such as methyl, ethyl, propyl, isopropyl, butyl, isobutyl, pentyl, iso-pentyl, hexyl and the like.

The term "alkenyl", as used herein, means a straight- or branched-chain hydrocarbon with one or more double bonds, comprising but not limited to ethenyl, propenyl and the like.

The term "aryl", as used herein, means a cyclic aromatic hydrocarbon, comprising but not limited to phenyl, naphthyl, anthryl, phenanthryl and the like.

The term "cycloalkyl", as used herein, means a saturated monocyclic or polycyclic alkyl which may fused with any aryl, comprising but not limited to cyclopropyl, cyclobutyl, cyclopentyl, cyclohexyl, cycloheptyl, cyclooctyl, indanyl, tetrahydronaphthyl and the like.

The term "halogen" or "halogen atom", as used herein, means fluorine, chlorine, bromine or iodine atom or group.

The term "heteroaryl", as used herein, means a monocyclic or polycyclic aromatic group in which one or more carbon atoms is/are replaced by one or more heteroatoms selected from the group consisting of nitrogen, oxygen or sulfur. If a heteroaryl comprises more than one heteroatom, these heteroatoms may be the same or different. Examples of heteroaryl include but are not limited to benzofuranyl, benzothiophenyl, benzimidazolyl, benzoxazolyl, benzothiazolyl, benzopyranyl, furyl, imidazolyl, indazolyl, indolizinyl, indolyl, isobenzofuryl, isoindolyl Isoquinolyl, isothiazolyl, isoxazolyl, naphthyridinyl, oxadizolyl, oxazinyl, oxazolyl, phthalazinyl, pteridinyl, purinyl, pyranyl, pyrazinyl, pyrazolyl, pyridazinyl, pyrido[3,4]indolyl, pyridinyl, pyrimidinyl, pyrrolyl, quinolizinyl, quinolyl, quinoxalinyl, thiadizolyl, thiatriazolyl, thiazolyl, thiophenyl, triazinyl, triazolyl, tertrazolyl, xanthyl and the like.

The term of "heterocycloalkyl", as used herein, means a saturated monocyclic or polycyclic alkyl, which may be fused with any aromatic group, wherein at least one carbon atom is replaced by heteroatoms selected from the group consisting of nitrogen, oxygen or sulfur. If a heterocycloalkyl comprises more than one heteroatom, these heteroatoms may be the same or different. Examples of heterocycloalkyl comprise but are not limited to azabicycloheptyl, azacyclobutyl, dihydroindolyl, morpholinyl, piperazinyl, piperidinyl, pyrrolidinyl, tetrahydrofuranyl, tetrahydroquinolyl, tetrahydroindazolyl, tetrahydroindolyl, tetrahydroisoquinolyl, tetrahydropyranyl, tetrahydroquinoxalyl, tetrahydrothiapyranyl, thiazolidinyl, thiomorpholinyl, thioxanthenyl, thioxanyl and the like.

A cyclic group can be bonded to another group in more than one way. If no particular bonding arrangement is specified, then all possible arrangements are encompassed. For example, the term "pyridyl", as used herein, comprises 2-, 3-, or 4-pyridyl, and "thienyl" comprises" 2- or 3-thienyl.

The term "-oxo", as used herein, means a carbonyl group formed by the combination of a carbon atom and oxygen atom.

The prodrugs and solvates of the present invention are encompassed. The term "produg", as used herein, refers to a compound that is a drug precursor which, following administrating to a subject, releases active ingredient in vivo via a metabolic or chemical process (e.g., under physiological pH conditions or via enzymatic activity). For discussion about the synthesis and use of the prodrugs, see T. HIGUCHI, V. STELLA, Prodrugs as Novel Delivery Systems, A.C.S. SYMPOSIUM SERIES vol. 14; and Edward B. Roche., Bioreversible Carriers in Drug Design, AMERICAN PHARMACEUTICAL ASSOCIATION AND PERGAMON PRESS, 1987, both of which are incorporated herein by reference. The term "prodrug" may include a metabolic precursor of the compound of the invention. The prodrug may be inactive when administered to a subject, but can be converted in vivo into the compound of formula (I) of the invention, or a salt and/or solvate thereof. The prodrug can be naturally occurring compounds or chemically synthetic compounds.

The compound of formula (I) of the present invention may be in a form of non-solvate, or a solvate in a pharmaceutically acceptable solvent such as water, ethanol and the like. And it is intended that the present invention will include all of the solvates and non-solvates of the compounds. The preferred solvate of the compound of formula (I) is a hydrate.

All of the stereoisomers of the compounds of the present invention, such as possible stereoisomers resulting from an asymmetric carbon atom on the R substituent of the compound of formula (I), including enantiomers and diastereomers, will fall into the scope of the present invention. All of the stereoisomers of the compounds of formula (I) of the present invention and the mixtures thereof, including the racemic mixtures, will be encompassed by the present invention. Further, all of the geometricisomers and stereoisomers will be encompassed by the present invention. For example, if the compound of formula (I) has a double bond, the cis-, trans-forms and the mixture thereof will fall into the scope of the present invention.

Diastereomeric mixtures can be separated into their respective diastereomers on the basis of their physical and chemical differences by methods well-known to those of ordinary skill in the art, such as chromatography and/or fractional crystallization. Enantiomers can be separated by reacting with an appropriate optically active compound to convert an enantiomeric mixture into a diasteriomeric mixture, then separating the diasteriomer and converting the individual diasteriomer into a pure enantiomer (e.g., via hydrolyzing). Also, some of the compounds of Formula (I) may be atropisomer (e.g., substituted biaryls) and are also encompassed by the invention.

The phase "pharmaceutically acceptable" indicates that the carrier(s), vehicle(s), diluent(s), auxiliary and/or salts are generally chemically and/or physically compatible with other ingredients constituting the formulation and physiologically compatible with the recipient.

The term "salts" and "pharmaceutically acceptable salts" refer to acid and basic salts of a compound of Formula (I), or a stereoisomer, or a prodrug thereof formed with inorganic and/or organic acids and bases, and also may include zwitterions salts (comprising inner salts) as well as quaternary ammonium salts, such as alkyl ammonium salts. These salts may be prepared in situ during the final isolation and purification of the compounds, or by reacting the compound of Formula (I), or a stereoisomer, or a prodrug thereof, with a suitable amount of organic or inorganic acids or bases (such as an equivalent amount) and isolating the salts thus formed. The salts may form precipitates from a solution and be collected by filtration or may be recovered by solvent evaporation, or by freeze drying after reaction in an aqueous medium.

Acid addition salts may include hydrobromide, hydroiodide, hydrochloride, sulfate, bisulfate, nitrate, acetate (including the salts formed with acetic acid, or trihaloacetic acid, for example, trifluoroacetic acid), oxalate, alginate, ascorbate, aspartate, butyrate, camphorate, camphor sulfonate, cyclopentyl propionate, digluconate, ethylsulfonate, 2-hydroxyethylsulfonate, 2-naphthalenesulfonate, nicotinate, persulfate, 3-phenylpropionate, picrate, pivalate, propionate, salicylate, benzene sulfonate, palmitate, stearate, laurate, borate, benzoate, lactate, phosphate, tosylate, citrate, maleate, fumarate, succinate, tartrate, thiocyanate, naphthylate, mesylate, glucoheptonate, lactobionate, dodecylsulfonate, adipate and the like.

Basic salts (e.g., the salts formed with an acidic moiety on R substituent, such as carboxy or phenolic hydroxy) include ammonium salts, alkaline metal salts (such as sodium, lithium and potassium salts), alkaline earth metal salts (such as calcium and magnesium salts), the salts formed with organic bases (such as organic amine), such as, dibenzyl ethylene diamine, dicyclohexylamine, hydrabamine, N-methyl-D-glucosamine, tert-butylamine, and the salts formed with amino acids such as arginine, lysine and the like. Further, basic salts include quaternary ammonium salts formed with alkaline agents containing nitrogen, including but not limited to ammonium, tetramethylammonium, tetraethylammonium, methylamine, dimethylamine salts, trimethylamine salts, triethylamine salts, ethylamine and the like. For additional examples, see, Berge, et al., J. Pharm. Sci., 66, 1-19 (1977).

It is also possible that the compounds of Formula (I) may exist as tautomeric isomers in equilibrium, and all of such forms are encompassed within the scope of the invention.

In an embodiment of the present invention, isotopically-labeled compounds of Formula (I), which are identical to those shown herein, except that one or more atoms of the compounds are replaced by another atom having an atomic mass or mass number different from that usually found in nature, are encompassed in the present invention. Examples of isotopes that may be incorporated into the compounds of Formula (I) include isotopes of hydrogen, carbon, nitrogen, oxygen, phosphorus, fluorine and chlorine, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl. The compounds of Formula (I), and stereoisomers and prodrugs thereof that contain the aforementioned isotopes and/or other atomic isotopes, and the pharmaceutically acceptable salts of the compounds, stereoisomers, and prodrugs thereof, are intended to be encompassed within the scope of the instant invention.

Certain isotopically-labeled compounds of Formula (I), for example, those compounds which are labelled with radioactive isotopes, such as $^3$H and $^{14}$C, are useful for tissue distribution assays for compounds and for substrates. Tritiated (i.e., $^3$H) and carbon-14 (i.e., $^{14}$C) isotopes are particularly preferred due to ease of preparation and detection. Furthermore, some isotopes such as deuterides (i.e., $^2$H) may afford certain therapeutic advantages due to higher metabolic stability, for example, increased half-life in vivo, or reduced dosage requirements and hence, may be preferred in some circumstances. The isotopically-labeled compounds of Formula (I) can generally be prepared by methods known to those of ordinary skill in the art, such as substituting an isotopically-labeled reagent for a non-isotopically-labeled reagent.

Use

The compound of the present invention is a modulator for new estrogen receptor ER-α36, and can modulate the function of ER-α36 in cells in vivo and in vitro. Therefore, the compound of formula (I) may be used to treat and/or prevent the diseases mediated by ER-α36.

In certain embodiments of the present invention, a method of modulating the function of ER-α36 in cells is provided. The method comprises administrating the compound of formula (I) to a cell expressing ER-α36. The cell may express endogenous ER-α36, or express exogenous ER-α36 by gene engineering, and may or may not express other estrogen receptors (such as, ER-α66, ER-α46, and ER-β). In a certain embodiment, the cell expresses endogenous ER-α36. In a preferred embodiment, the cell is a cancer cell expressing endogenous ER-α36. The cells expressing ER-α36 include, but are not limited to the cells of breast cancer, leukemia, liver cancer, lymphoma, lung cancer, myeloma, prostate cancer, ovary cancer, endometrial cancer, colon cancer and stomach cancer. In a more preferred embodiment, the cells expressing ER-α36 are breast cancer, leukemia, liver cancer, lymphoma, endometrial cancer and ovary cancer cells which express endogenous ER-α36. The breast cancer cells expressing ER-α36 comprise but are not limited to MCF7, MDA-MB-231 and SKBR-3 cells. The leukemia cells expressing ER-α36 comprise but are not limited to K562, MV-4-11, SUM159, HL-60 and Molt-4 cells. The liver cancer cells expressing ER-α36 comprise but are not limited to A2780, BEL7402, BEL7404, HEL-9204, Hep2G, Hep3B and Primary liver cancer stem cell Hep-12 derived from a patient. The lymphoma cells expressing ER-α36 comprise but are not limited to Daudi. The endometrial cancer cells expressing ER-α36 comprise but are not limited to Hec1A cells. The expression of endogenous ER-α36 can be increased or decreased by treating with one or more reagents comprising, for example, serum, E2β (17β-estradiol), tamoxifen and Fulvestrant (ICI-182,780).

In another embodiment, the present invention provides a method of preparing a cell expressing exogenous ER-α36. The cell may be prepared by gene engineering known to those of ordinary skill in the art (see Sambook et al., Molecular Cloning, A Laboratory Manual, 2nd Ed., 1989, Cold Spring Harbor Laboratory). In brief, an exogenous ER-α36 gene is prepared and inserted into an expression vector, which is then transfected into a host cell, and then the host cell is cultivated in a culture medium suitable for expressing exogenous ER- α36. The gene sequence of human ER-α36 is disclosed by Wang et al. in Biochem. Biophys. Res. Commun. 336, 1023-1027 (2005) (GeneBank registration No. BX640939). The cell expressing ER-α36 may or may not express endogenous ER-α36. The level of expressing endogenous or exogenous ER-α36 in a cell may be increased or decreased by treating with one or more reagents comprising, for example, serum, E2β (17β-estradiol), tamoxifen and Fulvestrant (ICI-182,780).

Thereby, the compound of formula (I) of the present invention may be used to prepare a medication for the prevention and/or treatment of an ER-α36-associated cancer. The cancer comprises but is not limited to anal cancer, bile duct cancer, bladder cancer, bone cancer, colorectal cancer (colon cancer, rectal cancer), brain cancer, breast cancer, carcinoid, cervical cancer, endocrine-related cancer, endometrial cancer, eye cancer, gallbladder cancer, head and neck cancer, Kaposi's sarcoma cancer, renal cell carcinoma, renal carcinoma, laryngeal carcinoma, leukemia, liver cancer, lung cancer, lymphoma, melanoma, mesothelioma, myeloma, neuroendocrine cancer, oesophagus cancer, ovary cancer, pancreas cancer, penis cancer, prostate cancer, skin cancer, soft tissue sarcomas cancer, spinal cord cancer, stomach cancer, testes cancer, thyroid cancer, vagina cancer, vulva cancer, or uterus cancer. In a preferred embodiment, the ER-α36-associated cancer includes breast cancer, cervical cancer, colon cancer, endometrial cancer, leukemia, liver cancer, lymphoma, lung cancer, myeloma, ovary cancer, prostate cancer, stomach cancer or uterus cancer. In a more preferred embodiment, the ER-α36-associated cancer includes breast cancer, cervical cancer, endometrial cancer, leukemia, liver cancer, lymphoma, lung cancer, uterus cancer or prostate cancer.

The ER-α36-associated diseases in the present invention also comprise but are not limited to alzheimer's disease, nerve degeneration, nerve aging and damage, birth control, abortion, bone loss, fracture, osteoporosis, malignant bone disease, paget's disease, periodontal disease, cartilage degration, endometriosis, hysteromyoma, hectic fever, increased levels of LDL cholesterol, cardiovascular disease, cognitive dysfunction, degenerative brain disease, restenosis, gynecomastia, vascular smooth muscle cell proliferation, obesity, urinary incontinence, anxiety, depression caused by estrogen deficiency, menopausal depression, postpartum depression, premenstrual syndrome, bipolar disorder, anxiety, dementia, obsessive-compulsive disorder, attention deficit disorder, dyssomnia, irritability, impulsive, immunodeficiency, autoimmunity disease, anger management, multiple sclerosis, Parkinson's disease, inflammation, inflammatory bowel disease, respiratory system disease, sexual dysfunction, hypertension, retinal degeneration and asthma.

The subject may be a mammal, such as a dog, cat, cow, sheep, horse or human, preferably a human. The effective amount of the compounds of Formula (I) will vary depending on the specific disease and is readily determined by one of ordinary skill in the art having benefit from the instant disclosure.

In certain embodiments, one or more compounds of the invention may be used in combination with one another. Alternatively, the compounds of the invention may also be used in combination with any other active agents for the preparation of a medicament or a pharmaceutical composition for modulating cell functions or treating diseases. If a combination of compounds is used, they may be administered to the subject simultaneously, separately or sequentially.

In certain embodiments, the compounds of the invention may be used in combination with one or more other anticancer agents. Suitable anticancer agents which may be combined include, but are not limited to alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, antimetabolites, protein synthesis inhibitors, kinase inhibitors, Antiestrogens, Cisplatin, Carboplatin, Interferon, Asparginase, Leuprolide, Flutamide, Megestrol, Mitomycin, Bleomycin, Doxorubicin, Iirinotecan and Taxol. In one embodiment, the anticancer agents are antiestrogens, such as Tomoxifen and Fulvestrant (ICI-182,750).

In certain embodiments of the present invention, a compound of Formula (I), a stereoisomer, or prodrugs thereof, or a pharmaceutically acceptable salt of the compound, stereoisomer, or prodrug, may be administered in the form of a pharmaceutical composition comprising a pharmaceutically acceptable carrier, vehicle, or diluent. They may be used to prepare a medicament for the prevention and/or treatment the diseases related to ER-α36 in a subject.

In certain embodiments, the composition of the present invention may be used to treat animal diseases. An ordinary veterinarian can administrate the compound of the present invention, or a veterinarily acceptable salt thereof, or a veterinarily acceptable solvent or prodrugs thereof in a form of a suitably acceptable formulation according to the practice. The veterinarian can determine the optimal dosage and administration route.

If a combination of many active compounds is used, they may be administered simultaneously, separately or sequentially.

Methods of Preparing the Compounds

The compounds of formula (I) may be prepared by various synthetic methods. Typical preparation methods are demonstrated as follows. $R^1$, $R^2$, $R^3$, $R^4$, $R^5$, $R^6$, $R^7$ and

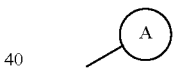

are defined above, unless otherwise indicated.

It is apparent to persons skilled in the art that the exact methods of preparing the compounds may slightly vary depending on the chemical structure. Further, it is necessary to protect unstable or active groups by conventional protecting groups (shown as P) in most of the preparation methods as set forth below. The properties of the protecting groups and the process for introduction or removal of the same are well-known in the art (see, for example, Greene T. W., Protective Groups in Organic Synthesis, John Wiley & Sons, New York, 1991). The following schemes 1 to 6 and the related description are taken as some examples of preparing the compounds of formula (I), and not intended to limit the scope of the prevent invention.

Scheme 1

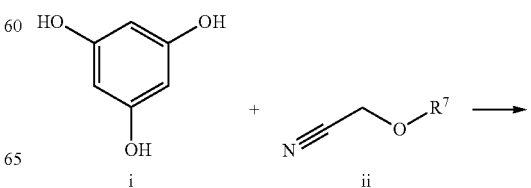

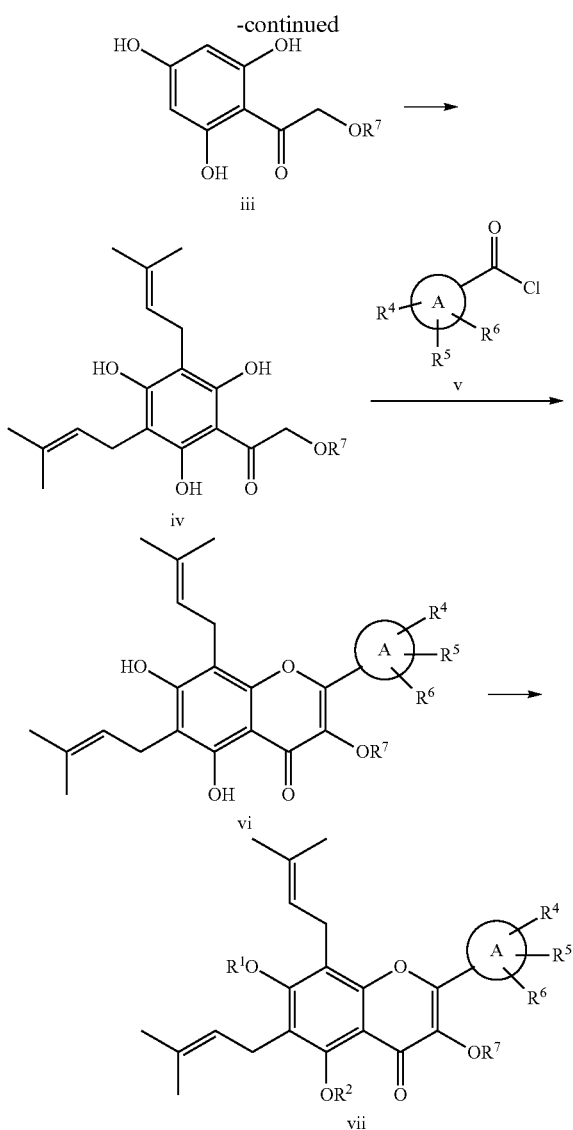

The compounds of formula (I) may be prepared in several steps. Compound iii may be prepared from compounds i and ii through a Houben-Hoesch reaction (a modified Friedel-Crafts acylation) under catalysis of a Lewis acid. The Lewis acid suitable for the reaction comprises anhydrous zinc chloride, anhydrous aluminum trichloride, ferric chloride, titanium tetrachloride, stannic chloride, boron trifluoride-ether complexes and the like. This reaction is carried out usually at a temperature of between about 0 and about 120° C. for 1-20 hours.

Compound iv may be prepared by reacting iso-pentenyl bromide with compound iii under alkaline conditions. The solvent useful for the reaction may comprise, for example methanol, DMF (N,N-dimethyllonnamide), THF (tetrahydrofuran), water, toluene, DME (1,2-dimethoxyethane), as well as mixed solvents, such as methanol-water, DMF-water, tetrahydrofuran-water, and the like. The solvent used in the reaction is preferably water. The alkali suitable for the reaction may comprise, for example potassium hydroxide, potassium carbonate, cesium carbonate, sodium methoxide, sodium hydride, potassium tert-butoxide, DBU (1,8-diazadicyclo-biscyclo(5,4,0)-7-hendecene) n-butyl lithium, LDA (diisopropylamino lithium), LHMDS (lithium hexamethyldisilazide), and the like. The reaction is carried out usually at a temperature of between about 0 and about 100° C. for 1-20 hours.

The compound vi may be prepared via a condensation reaction of compounds iv and v in an inert solvent. The inert solvent suitable for the reaction may comprise, for example DME, 1,2-diethoxyethane, THF, 1,4-dioxane, DMF, N,N-dimethylacetamide, pyridine, N-methyl-2-pyrrolidone. The reaction is carried out under an alkaline condition, and suitable alkali may comprise, for example potassium hydroxide, potassium carbonate, cesium carbonate, sodium hydride, sodium methoxide, potassium tert-butoxide, DBU (1,8-diazadicyclo-biscyclo(5,4,0)-7-hendecene), n-butyl lithium, LDA (diisopropylamino lithium), LHMDS (lithium hexamethyldisilazide), and the like. A chemical equivalent or catalytic amount of a phase transfer-catalyst may be added to the reaction, such as 18-crown-6, TBAB (tetrabutylammonium bromide), TBAF (tetrabutylammonium fluoride), and the like. The reaction is carried out usually at a temperature of about 0-140° C., and preferably at a solvent reflux temperature for 1-20 hours.

When $R^1$ and $R^2$ are substituted or non-substituted alkyl or alkenyl, the compound vii may be prepared via a reaction of compound vi with bromide or iodide in a inert solvent. The inert solvent suitable for the reaction may comprise ether, such as DME, 1,2-diethoxyethane, THF, 1,4-dioxane, DMF, N,N-dimethylacetamine, pyridine, N-methyl-2-pyrrolidone, dichloromethane, trichloromethane, and the like. The solvent for the reaction is preferably dichloromethane. A chemical equivalent or catalytic amount of an additive, such as triethylamine, N,N-diisopropylethylamine, or tetrabutyl ammonium hydroxide, may be added to the reaction. A preferred additive in the reaction is triethylamine. The reaction is carried out usually at a temperature of between about 0 and about 80° C. for 1-20 hours.

When $R^1$ and $R^2$ are substituted or non-substituted carbonyl, the compound vii may be prepared via a reaction of compound vi with anhydride compounds, carboxylic acid compounds or acyl chloride compounds in an inert solvent. The inert solvent suitable for the reaction may comprise ether, such as DME, 1,2-diethoxyethane, THF, DMF, N,N-dimethylacetamine, pyridine, N-methyl-2-pyrrolidone, dichloromethane, trichloromethane, and the like. The solvent for the reaction is preferably dichloromethane. A chemical equivalent or catalytic amount of an additive, such as triethylamine, N,N-diisopropylethylamine, DMAP (4-methylaminopyridine), DCC (N,N'-dicyclohexylcarbodiimide), or HOBT (1-hydroxy-benzo-triazole), may be added to the reaction. A preferred additive in the reaction is triethylamine. The reaction is carried out usually at a temperature of between about 0 and about 80° C. for 1-20 hours.

Scheme 2

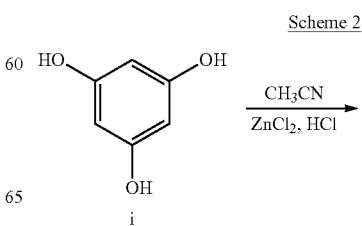

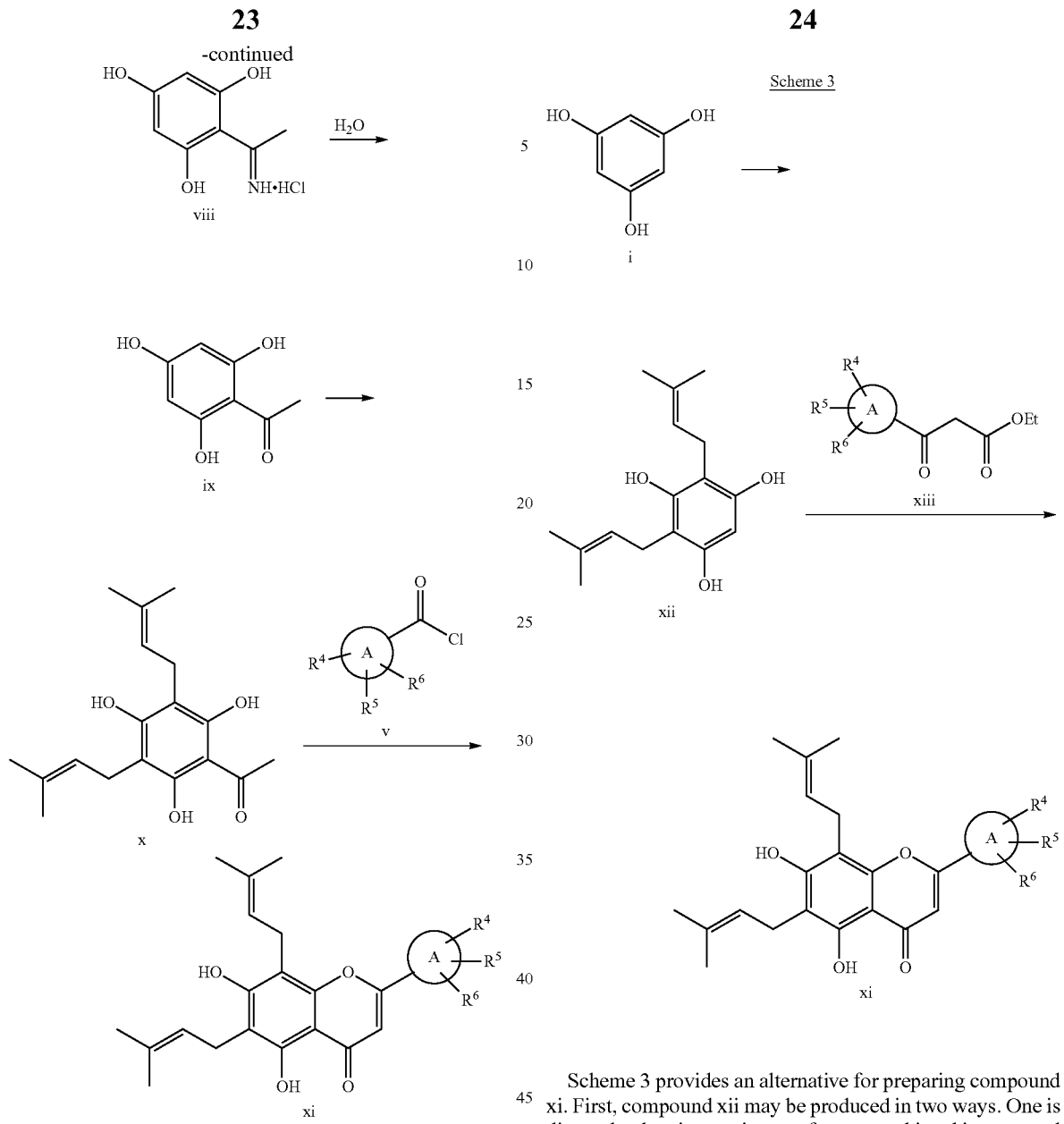

The preparation of a compound of formula (I) wherein $R^3$ is hydrogen is provided in scheme 2. Compound I reacts with methyl cyanide and dry zinc chloride in an inert solvent, with a dry HCl gas introduced into the reaction system. The resulting precipitate is then filtered and collected to yield the compound viii. The inert solvent suitable for the reaction may comprise ether, such as diethyl ether, toluene, DME, 1,2-diethoxyethane, 1,4-dioxane, THF, DMF, N,N-dimethylacetamine, and N-methyl-2-pyrrolidone, and preferably toluene or ether. The reaction is carried out usually at a temperature of between about 0 and about 35° C. for 1-48 hours.

The compound ix may be produced through a hydrolytic reaction of compound viii. The reaction is carried out usually at a temperature of between about 50 and about 100° C. for 1-72 hours, and preferably at a temperature of between about 80 and about 100° C. for 1-24 hours.

The compound x may be prepared referring to the preparation method of compound iv in scheme i. Similarly, compound xi may be prepared referring to the preparation method of compound vi in scheme 1.

Scheme 3 provides an alternative for preparing compound xi. First, compound xii may be produced in two ways. One is directed to heating a mixture of compound i and isopentenyl bromide in an inert solvent at a temperature of 10-100° C. for 2-30 hours, where a Friedel-Crafts acylation reaction occurs. The inert solvent suitable for the reaction may comprise ether, such as DME, 1,2-diethoxyethane, 1,4-dioxane, THF, toluene, and the like. Preferably, the reaction condition is at a temperature of 30-80° C. for 5-20 hours.

Another way for preparing compound xii comprises reacting compound i with 2-methyl-butenol. The inert solvent suitable for the reaction may comprise ether, such as DME, 1,2-diethoxyethane, THF, 1,4-dioxane, toluene, and the like. The preferred solvent is 1,4-dioxane. A chemical equivalent or catalytic amount of boron trifluoride-ether complexes may be added as additive to the reaction. The reaction is carried out usually at a temperature of between about 0 and about 80° C. for 1-24 hours, and preferably at a temperature of between about 40 and about 80° C. for 1-8 hours.

Compound xi may be obtained by heating a mixture of compound xii and compound xiii in a microwave reactor at a temperature of about 150 to about 300° C. for 1-60 minutes.

25

Scheme 4

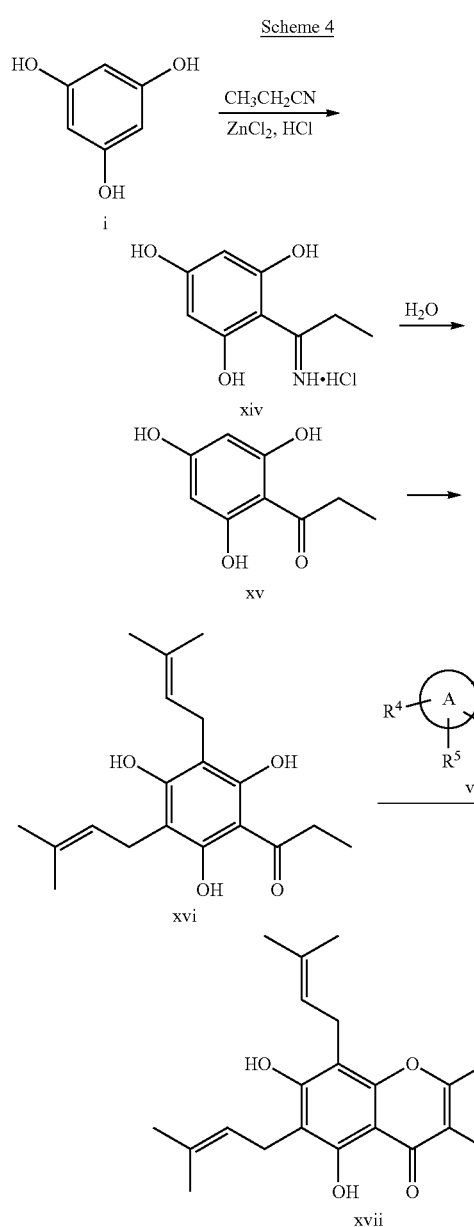

The preparation of a compound of formula (I) wherein $R^3$ is methyl is provided in scheme 4. The preparation of the compound is the same as those of compounds viii and ix in scheme 2. Compound i reacts with propionitrile and dry zinc chloride in an inert solvent, with a dry HCl gas introduced into the reaction system. The resulting precipitate is then filtered and collected to yield the compound xiv, which subsequently hydrolyses directly to obtain compound xv. The inert solvent suitable for the reaction may comprise ether, such as diethyl ether, toluene, DME, 1,2-diethoxyethane, 1,4-dioxane, THF, DMF, N,N-dimethylacetamine, and N-methyl-2-pyrrolidone, and preferably toluene or ether. The reaction is carried out usually at a temperature of between about 0 and about 35° C. for 1-48 hours.

Compound xvi may be prepared by a method similar to the compound iv in scheme 1. Similarly, Compound xvii may be prepared by a method similar to the compound vi in scheme 1.

26

When $R^3$ of the compound in formula (I) is hydroxy, the compound xxii may be prepared according to one of scheme 5 and scheme 6 as follows.

Scheme 5

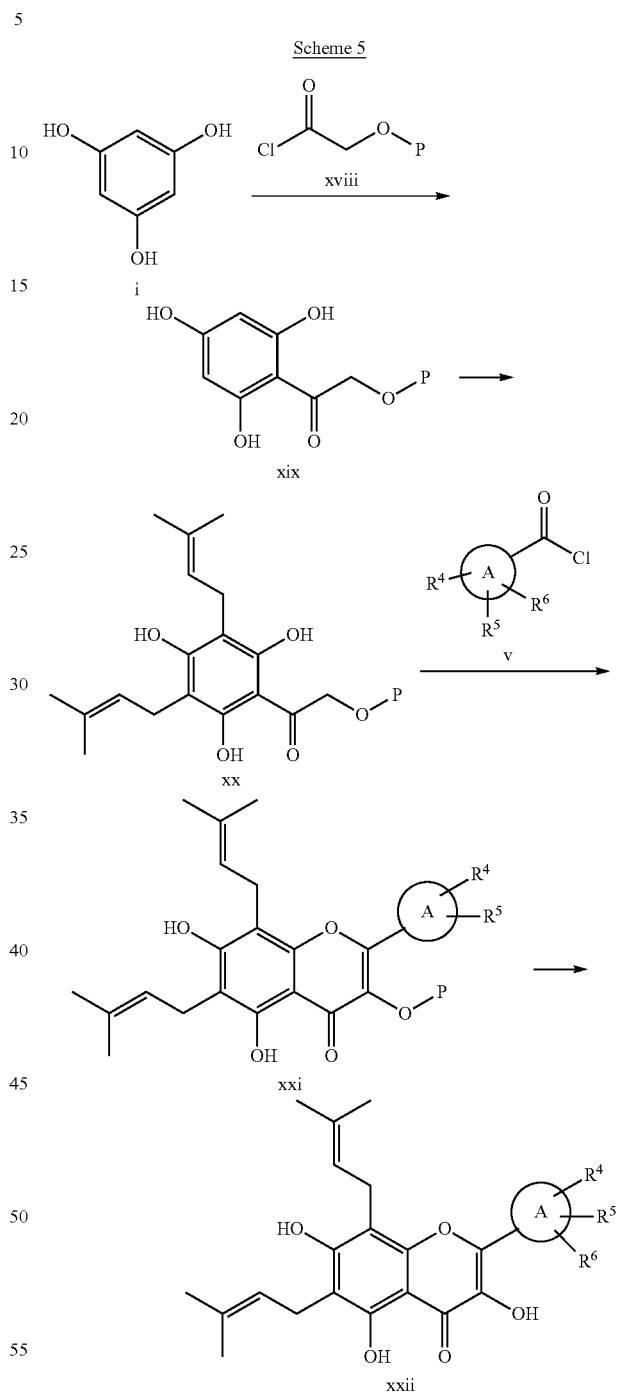

In scheme 5, P is a hydroxy protecting group. Compound xix may be prepared from compound i and an acyl chloride compound xviii through Houben-Hoesch reaction. Lewis acid is usually used as a catalyst of the reaction. Lewis acid suitable for the reaction comprises aluminum trichloride, ferric chloride, stannic chloride, titanium tetrachloride, boron trifluoride-ether complexes, and the like. Normally, the reaction occurs in an inert solvent, at a temperature of about −78 to about 80° C., and for 2-30 hours. The inert solvent suitable for the reaction may comprise ether, such as ethyl ether, DME, 1,2-diethoxyethane, THF, 1,4-dioxane, dichloromethane, trichlormethane, and the like. The preferred reaction temperature is at −20° C.-50° C.

The compound xx may be prepared by a method similar to that in scheme 1 for compound iv. Similarly, the compound xxi may be prepared by a method similar to that for the compound vi.

The compound xxii may be obtained by removing the protecting group of compound xxi. The method for removal may vary depending on a variation of protecting groups (see Greene T. W. et al., Protective Groups in Organic Synthesis, John Wiley & Sons, NewYork, 1991). The preferred protective group comprises benzyl, benzoyl, benzyloxycarbonyl, TBDMS (tert-butyldimethylsilyl), THP (tetrahydropyranyl), methyl, MOM (methoxymethyl), PMB (para-methoxybenzyl), and the like.

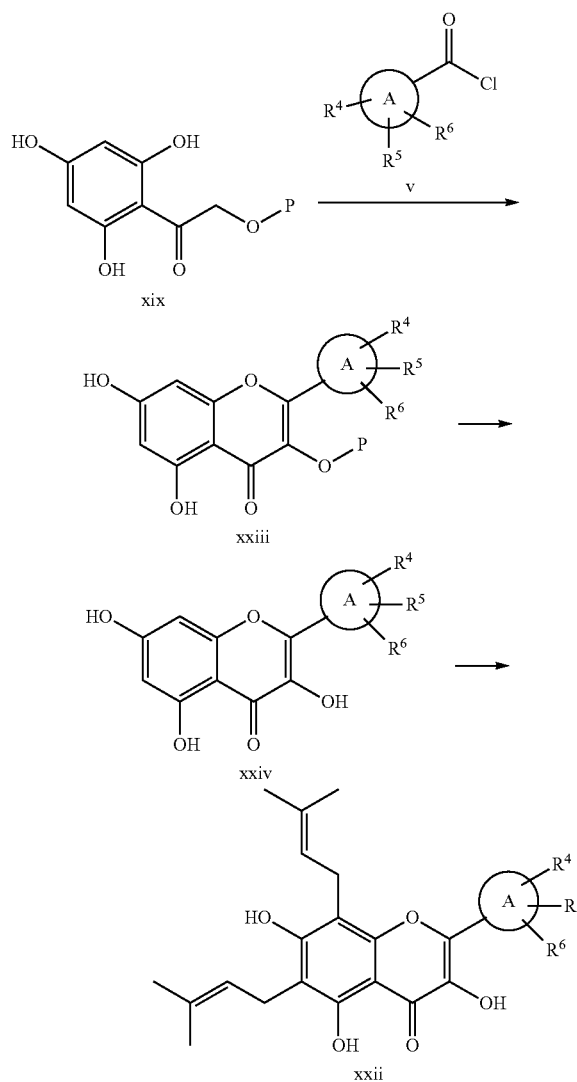

Scheme 6

According to scheme 6, compound xxiii may be prepared by condensation of compound xix and compound v, followed by removal of the protective group. The method of preparing compound xxiii is similar to that of preparing compound vi in scheme 1. The removal of protective group may also refer to the methods disclosed in Greene T. W. et al., Protective Groups in Organic Synthesis, John Wiley & Sons, NewYork, 1991.

The compound xxii may be prepared by reacting isopentenyl bromide with compound xxiv under an alkaline condition. The solvent suitable for the reaction may comprise, for example methanol, DMF, THF, $H_2O$, toluene, DME, and mixed solvents, such as methanol-water, DMF-water, tetrahydrofuran-water, and the like. The solvent used in the reaction is preferably water. The alkali suitable for the reaction may comprise for example potassium hydroxide, potassium carbonate, cesium carbonate, sodium methoxide, sodium hydride, potassium tert-butoxide, DBU, n-butyl lithium, LDA, LHMDS, and the like. The reaction is carried out usually at a temperature of between about 0 and about 100° C. for 1-20 hours.

EXAMPLES

The present invention is illustrated by the following non-limiting examples in which, unless stated otherwise, room temperature or ambient temperature refers to a range of 18-25° C. Evaporation of solvent was carried out using a rotary evaporator under reduced pressure; reactions were monitored by thin layer chromatography (TLC) and reaction times were given for illustration only. Structure and purity for all of isolated compounds were identified by at least one of the following techniques: TLC, mass spectrometry, nuclear magnetic resonance (NMR), high pressure liquid chromatography (HPLC). Yields were given only for the purpose of illustration.

Example 1

2-(3-fluoro-4-methoxyphenyl)-5,7-dihydroxy-3-methoxy-6,8-di(3-methyl-2-buten-1-yl)-4H-benzopyran-4-one (compound 1)

Step 1: preparing 2-methoxy-1-(2,4,6-trihydroxyphenyl)ethanone

Phloroglucinol (35.1 g, 279 mmol) was dissolved in ether (500 mL), to which were added anhydrous zinc chloride (8 g, 59 mmol) and 2-methoxymethyl cyanide (18 g, 253 mmol) in an ice-bath. Dry HCl gas was introduced into the reaction mixture, with vigorous stirring for 5 hrs, and precipitates were formed. The precipitates were filtered and collected, followed by dissolving into water and refluxing for 3 hrs. After cooling, red precipitates were collected and recrystallized in water, to give a white desired compound (45 g, yield 81%). 1H NMR (400 MHz, DMSO-$d_6$): δ=12.14 (s, 2H), 10.41 (s, 1H), 5.79 (s, 2H), 4.56 (s, 2H), 3.32 (s, 3H).

Step 2: preparing 2-methoxy-1-[2,4,6-trihydroxy-3,5-di(3-methyl-2-buten-1-yl)phenyl]ethanone 2-methoxy-1-(2,4,6-trihydroxyphenyl)ethanone (8.3 g, 42 mmol) was dissolved in a 5% potassium hydroxide aqueous solution (84 ml). After the reaction mixture was cooled below 0° C., Isopentenyl bromide (12.48 g, 84 mmol) was slowly added dropwise to within 30 minutes. The reaction mixture was stirred at room temperature (RT) for 2 hours, then poured into an ice water and acidified to pH 2. The reaction mixture was extracted with ethyl acetate. The extract was collected and dried over anhydrous sodium sulfate, followed by removing solvent. The desired compound was obtained by purifying the residue by silica gel column chromatography (dichloromethane as eluent) (5.7 g, yield 41%). 1H NMR (400 MHz, DMSO-$d_6$): δ=11.44 (s, 2H), 9.24 (s, 1H), 5.00 (t, 2H, J=6.8 Hz), 4.63 (s, 2H,), 3.31 (s, 3H), 3.22 (d, 4H, J=6.8 Hz), 1.67 (s, 6H), 1.58 (s, 6H).

Step 3: preparing 2-(3-fluoro-4-methoxyphenyl)-5,7-dihydroxy-3-methoxy-6,8-di(3-methyl-2-buten-1-yl)-4H-benzopyran-4-one Under nitrogen atmosphere, 2-methoxy-1-[2,4,6-trihydroxy-3,5-di(3-methyl-2-buten-1-yl)phenyl]ethanone (300 mg, 0.897 mmol), anhydrous potassium carbonate powder (744 mg, 5.38 mmol), TBAB (tetrabutyl ammonium bromide, 434 mg, 1.346 mmol), and 3-fluoro-4-methoxybenzoyl chloride (388 mg, 2.057 mmol) were dissolved in toluene (84 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 20 mL methanol-$H_2O$ (4:1) mixture, to which was added potassium hydroxide (1 g). The mixture was heated to reflux for 2 hours, then cooled to ambient temperature, acidified to pH 4 with 1N HCl solution, and extracted with dichloromethane three times. The combined organic phase was dried over anhydrous sodium sulfate, with removal of solvent. The crude product was purified by silica gel column chromatography (eluent: ethyl acetate/petroleum ether, 1:50) to give the desired compound (137.8 mg, yield 32.6%). 1H NMR (400 MHz, CDCl$_3$): δ=12.89 (s, 1H), 7.94 (dt, 1H, $J_1$=8.8 Hz, $J_2$=2.0 Hz), 7.90 (dd, 1H, $J_1$=8.8 Hz, $J_2$=2.0 Hz), 7.08 (t, 1H, J=8.8 Hz), 6.36 (s, 1H), 5.27-5.23 (m, 2H), 3.99 (s, 3H,), 3.88 (s, 3H), 3.54 (d, 2H, J=6.8 Hz), 3.47 (d, 2H, J=6.8 Hz), 1.85 (s, 3H), 1.84 (s, 3H), 1.77 (s, 3H), 1.75 (s, 3H); LC-MS (ESI) m/z 469.5 [M+14]+.

Compounds 2 to 80 were obtained according to Example 1 from intermediate 2-methoxy-1-[2,4,6-trihydroxy-3,5-di(3-methyl-2-buten-1-yl)phenyl]ethanone and alkyl acyl chloride, aryl acyl chloride or heteroaryl acyl chloride with different substituted groups. The details are as shown below in Table 1.

TABLE 1

| Compound No. | Compound name | $^1$H-NMR | LC-MS m/z (ESI) |
|---|---|---|---|
| 2 | 2-(3,5-difluorophenyl)-5,7-dihydroxy-3-methoxy-6,8-di(3-methyl-2-buten-1-yl)-4H-benzopyran-4-one | (400 MHz, CDCl$_3$): δ = 12.73 (s, 1H), 7.67 (dd, 2H, J1 = 8.8 Hz, J2 = 2.0 Hz), 6.97-6.93 (m, 1H), 6.42 (brs, 1H), 5.23 (dt, 2H, J1 = 21.6 Hz, J2 = 7.2 Hz), 3.92 (s, 3H,), 3.53 (d, 2H, J = 6.8 Hz), 3.47 (d, 2H, J = 6.8 Hz), 1.86 (s, 3H), 1.84 (s, 3H), 1.78 (s, 3H), 1.76 (s, 3H). | 457.7 [M + H]+. |
| 3 | 2-(3-fluorophenyl)-5,7-dihydroxy-3-methoxy-6,8-di(3-methyl-2-buten-1-yl)-4H-benzopyran-4-one | (400 MHz, CDCl3): δ = 12.81 (s, 1H), 7.90 (d, 1H, J = 8.0 Hz), 7.82-7.79 (m, 1H), 7.51-7.46 (m, 1H), 7.22 (td, 1H, J1 = 8.4 Hz, J2 = 2.4 Hz), 6.39 (brs, 1H), 5.29-5.23 (m, 2H), 3.89 (s, 3H,), 3.54 (d, 2H, J = 6.8 Hz), 3.47 (d, 2H, J = 7.2 Hz), 1.85 (s, 3H), 1.83 (s, 3H), 1.77 (s, 3H), 1.75 (s, 3H). | 439.6 [M + H]+; |
| 4 | 2-(3,4-difluorophenyl)-5,7-dihydroxy-3-methoxy-6,8-di(3-methyl-2-buten-1-yl)-4H-benzopyran-4-one | (400 MHz, CDCl$_3$): δ = 12.78 (s, 1H), 7.98-7.89 (m, 2H), 7.30 (dd, 1H, $J_1$ = 18.0 Hz, $J_2$ = 8.8 Hz), 6.40 (brs, 1H), 5.30-5.20 (m, 2H), 3.89 (s, 3H,), 3.54 (d, 2H, J = 6.8 Hz), 3.49 (d, 2H, J = 8.4 Hz), 1.85 (s, 3H), 1.83 (s, 3H), 1.76 (s, 3H), 1.75 (s, 3H). | 457.9 [M + H]+ |
| 5 | 2-(-fluoro-4-chlorophenyl)-5,7-dihydroxy-3-methoxy-6,8-di(3-methyl-2-buten-1-yl)-4H-benzopyran-4-one | (400 MHz, CDCl$_3$): δ = 12.77 (s, 1H), 7.93-7.86 (m, 2H), 7.53 (dd, 1H, $J_1$ = 8.4 Hz, $J_2$ = 7.6 Hz), 6.42 (brs, 1H), 5.27-5.21 (m, 2H), 3.89 (s, 3H,), 3.54 (d, 2H, J = 6.8 Hz), 3.47 (d, 2H, J = 6.8 Hz), 1.85 (s, 3H), 1.83 (s, 3H), 1.78 (s, 3H), 1.75 (s, 3H). | 473.8 [M + H]+ |
| 6 | 2-(3-fluoro-4-trifluoromethylphenyl)-5,7-dihydroxy-3-methoxy-6,8-di(3-methyl-2-butylene-1-yl)-4H-benzopyran-4-one | (400 MHz, CDCl$_3$): δ = 12.70 (s, 1H), 8.01 (d, 1H, J = 8.0 Hz), 7.95 (d, 1H, J = 12.0 Hz), 7.74 (t, 1H, J = 8.0 Hz), 6.44 (brs, 1H), 5.30-5.16 (m, 2H), 3.93 (s, 3H,), 3.54 (d, 2H, J = 6.8 Hz), 3.48 (d, 2H, J = 6.8 Hz), 1.85 (s, 3H), 1.83 (s, 3H), 1.78 (s, 3H), 1.76 (s, 3H). | 506.9 [M + H]+ |
| 7 | 2-(4-fluorophenyl)-5,7-dihydroxy-3-methoxy-6,8-di(3-methyl-2-buten-1-yl)-4H-benzopyran-4-one | (300 MHz, CDCl$_3$): δ = 8.11 (dd, 2H, J = 8.7, 5.4 Hz), 7.23 (dd, 2H, $J_1$ = 8.7 Hz, $J_2$ = 5.4 Hz), 6.36 (brs, 1H), 5.26-5.23 (m, 2H), 3.86 (s, 3H,), 3.54 (d, 2H, J = 6.8 Hz), 3.48 (d, 2H, J = 7.2 Hz), 1.85 (s, 3H), | 439.2 [M + H]+ |

TABLE 1-continued

| Compound No. | Compound name | $^1$H-NMR | LC-MS m/z (ESI) |
|---|---|---|---|
| | | 1.81 (s, 3H), 1.77 (s, 3H), 1.74 (s, 3H). | |
| 8 | 2-(3-chloro-4-fluorophenyl)-5,7-dihydroxy-3-methoxy-6,8-di(3-methyl-2-butylene-1-yl)-4H-benzopyran-4-one | (400 MHz, CDCl$_3$): δ = 12.79 (s, 1H), 8.14 (dd, 1H, J$_1$ = 6.8 Hz, J$_2$ = 2.0 Hz), 8.04-8.01 (m, 1H), 7.28 (t, 1H, J = 8.8 Hz), 6.40 (brs, 1H), 5.26-5.22 (m, 2H), 3.88 (s, 3H), 3.53 (d, 2H, J = 6.4 Hz), 3.48 (d, 2H, J = 7.2 Hz), 1.85 (s, 3H), 1.83 (s, 3H), 1.78 (s, 3H), 1.76 (s, 3H). | 473.6 [M + H]$^+$ |
| 9 | 2-(4-fluoro-3-methoxyphenyl)-5,7-dihydroxy-3-methoxy-6,8-di(3-methyl-2-butylene-1-yl)-4H-benzopyran-4-one | (400 MHz, CDCl$_3$): δ = 12.84 (s, 1H), 7.80 (dd, 1H, J$_1$ = 8.4 Hz, J$_2$ = 2.0 Hz), 7.71-7.62 (m, 1H), 7.20 (dd, 1H, J$_1$ = 11.8 Hz, J$_2$ = 8.8 Hz), 6.36 (brs, 1H), 5.27-5.25 (m, 2H), 3.95 (s, 3H), 3.87 (s, 3H), 3.54 (d, 2H, J = 6.8 Hz), 3.47 (d, 2H, J = 7.2 Hz), 1.85 (s, 3H), 1.80 (s, 3H), 1.77 (s, 3H), 1.73 (s, 3H). | 469.7 [M + H]$^+$ |
| 10 | 2-(4-chlorophenyl)-5,7-dihydroxy-3-methoxy-6,8-di(3-methyl-2-butylene-1-yl)-4H-benzopyran-4-one | (300 MHz, CDCl$_3$): δ = 12.84 (s, 1H), 8.03 (d, 2H, J = 9.0 Hz), 7.48 (d, 2H, J = 9.0 Hz), 6.38 (brs, 1H), 5.27-5.23 (m, 2H), 3.86 (s, 3H), 3.54 (d, 2H, J = 6.3 Hz), 3.47 (d, 2H, J = 7.2 Hz), 1.85 (s, 3H), 1.81 (s, 3H), 1.77 (s, 3H), 1.74 (s, 3H). | 455.1 [M + H]$^+$ |
| 11 | 2-(4-chloro-3-methylphenyl)-5,7-dihydroxy-3-methoxy-6,8-di(3-methyl-2-buten-1-yl)-4H-benzopyran-4-one | (400 MHz, CDCl$_3$): δ = 12.87 (s, 1H), 7.94 (d, 1H, J = 1.6 Hz), 7.85 (dd, 1H, J$_1$ = 8.4 Hz, J$_2$ = 2.4 Hz), 7.47 (d, 1H, J = 8.8 Hz), 6.37 (brs, 1H), 5.28-5.22 (m, 2H), 3.85 (s, 3H), 3.53 (d, 2H, J = 6.3 Hz), 3.47 (d, 2H, J = 6.8 Hz), 2.47 (s, 3H), 1.85 (s, 3H), 1.81 (s, 3H), 1.77 (s, 3H), 1.74 (s, 3H). | 468.9 [M + H]$^+$ |
| 12 | 2-(3,4-dichlorophenyl)-5,7-dihydroxy-3-methoxy-6,8-di(3-methyl-2-butylene-1-yl)-4H-benzopyran-4-one | (300 MHz, CDCl$_3$): δ = 8.17 (d, 1H, J = 1.8 Hz), 7.96 (dd, 1H, J$_1$ = 8.7 Hz, J$_2$ = 2.1 Hz), 7.58 (d, 1H, J = 8.7 Hz), 6.40 (brs, 1H), 5.28-5.22 (m, 2H), 3.89 (s, 3H), 3.52 (d, 2H, J = 6.6 Hz), 3.47 (d, 2H, J = 7.2 Hz), 1.85 (s, 3H), 1.83 (s, 3H), 1.78 (s, 3H), 1.75 (s, 3H). | 489.1 [M + H]$^+$ |
| 13 | 2-(4-chloro-3-trifluoromethylphenyl)-5,7-dihydroxy-3-methoxy-6,8-di(3-methyl-2-butylene-1-yl)-4H-benzopyran-4-one | (400 MHz, CDCl$_3$): δ = 12.74 (s, 1H), 8.44 (d, 1H, J = 2.0 Hz), 8.21 (dd, 1H, J$_1$ = 8.4 Hz, J$_2$ = 2.0 Hz), 7.65 (d, 1H, J = 8.4 Hz), 6.43 (brs, 1H), 5.28-5.20 (m, 2H), 3.91 (s, 3H), 3.52 (d, 2H, J = 6.6 Hz), 3.47 (d, 2H, J = 7.2 Hz), 1.87 (s, 3H), 1.85 (s, 3H), 1.78 (s, 3H), 1.73 (s, 3H). | 522.8 [M + H]$^+$ |
| 14 | 2-(2-fluoro-4-chlorophenyl)-5,7-dihydroxy-3-methoxy-6,8-di(3-methyl-2-butylene-1-yl)-4H-benzopyran-4-one | (400 MHz, CDCl$_3$): δ = 12.77 (s, 1H), 7.59 (t, 1H, J = 8.0 Hz), 7.29-7.24 (m, 2H), 6.38 (brs, 1H), 5.28-5.20 (m, 2H), 3.86 (s, 3H), 3.48 (d, 2H, J = 8.4 Hz), 3.44 (d, 2H, J = 8.4 Hz), 1.84 (s, 3H), 1.76 (s, 3H), 1.71 (s, 6H). | 472.9 [M + H]$^+$ |
| 15 | 2-(4-trifluoromethylphenyl)-5,7-dihydroxy-3-methoxy-6,8-di(3-methyl-2-butylene-1-yl)-4H-benzopyran-4-one | (400 MHz, CDCl$_3$): δ = 8.20 (d, 2H, J = 8.4 Hz), 7.77 (d, 2H, J = 8.4 Hz), 6.41 (brs, 1H), 5.28-5.20 (m, 2H), 3.89 (s, 3H), 3.54 (d, 2H, J = 7.2 Hz), 3.47 (d, 2H, J = 8.4 Hz), 1.85 (s, 3H), 1.82 (s, 3H), 1.78 (s, 3H), 1.75 (s, 3H). | 488.9 [M + H]$^+$ |
| 16 | 2-(4-methylphenyl)-5,7-dihydroxy-3-methoxy-6,8-di(3-methyl-2-butylene-1-yl)-4H-benzopyran-4-one | (300 MHz, CDCl$_3$): δ = 7.98 (d, 2H, J = 8.1 Hz), 7.31 (d, 2H, J = 8.1 Hz), 6.32 (brs, 1H), 5.28-5.20 (m, 2H), 3.84 (s, 3H), 3.54 (d, 2H, J = 6.6 Hz), 3.47 (d, 2H, J = 6.9 Hz), 2.44 (s, 3H), 1.85 (s, 3H), 1.82 (s, 3H), 1.77 (s, 3H), 1.75 (s, 3H). | 435.2 [M + H]$^+$ |
| 17 | 2-(4-isopropylphenyl)-5,7-dihydroxy-3-methoxy-6,8-di(3-methyl-2-butylene-1-yl)-4H- | (400 MHz, CDCl$_3$): δ = 12.94 (s, 1H), 8.03 (d, 2H, J = 7.6 Hz), 7.37 (d, 2H, J = 7.2 Hz), 6.34 (brs, 1H), | 462.9 [M + H]$^+$ |

TABLE 1-continued

| Compound No. | Compound name | $^1$H-NMR | LC-MS m/z (ESI) |
|---|---|---|---|
| | benzopyran-4-one | 5.28-5.20 (m, 2H), 3.87 (s, 3H), 3.56 (d, 2H, J = 6.8 Hz), 3.46 (d, 2H, J = 6.9 Hz), 3.02-2.96 (m, 1H), 1.85 (s, 3H), 1.83 (s, 3H), 1.77 (s, 3H), 1.75 (s, 3H), 1.30 (d, 6H, J = 6.8 Hz). | |
| 18 | 2-(quinoxalin-6-yl)-5,7-dihydroxy-3-methoxy-6,8-di(3-methyl-2-butylene-1-yl)-4H-benzopyran-4-one | (400 MHz, CDCl$_3$): δ = 12.76 (s, 1H), 8.90 (d, 2H, J = 6.0 Hz), 8.81 (d, 1H, J = 2.0 Hz), 8.44 (dd, 1H, J$_1$ = 8.8 Hz, J$_2$ 2.0 Hz), 8.19 (d, 1H, J = 8.8 Hz), 6.60 (brs, 1H), 5.26-5.23 (m, 2H), 3.94 (s, 3H), 3.58 (d, 2H, J = 6.8 Hz), 3.44 (d, 2H, J = 6.9 Hz), 1.81 (s, 6H), 1.73 (s, 6H). | 472.8 [M + H]$^+$ |
| 19 | 2-(naphthalen-2-yl)-5,7-dihydroxy-3-methoxy-6,8-di(3-methyl-2-butylene-1-yl)-4H-benzopyran-4-one | (400 MHz, CDCl$_3$): δ = 12.94 (s, 1H), 8.63 (s, 1H), 8.13 (dd, 1H, J$_1$ = 8.8 Hz, J$_2$ = 1.6 Hz), 7.96 (d, 2H, J = 8.4 Hz), 7.90 (d, 1H, J = 7.6 Hz), 7.60-7.57 (m, 2H), 6.39 (brs, 1H), 5.30-5.28 (m, 2H), 3.91 (s, 3H), 3.60 (d, 2H, J = 6.8 Hz), 3.48 (d, 2H, J = 6.9 Hz), 1.86 (s, 3H), 1.85 (s, 3H), 1.78 (s, 3H), 1.76 (s, 3H). | 470.7 [M + H]$^+$ |
| 20 | 2-(2,3-dihydrobenzo[b][1,4]dioxan-6-yl)-5,7-dihydroxy-3-methoxy-6,8-di(3-methyl-2-buten-1-yl)-4H-benzopyran-4-one; | (400 MHz, CDCl$_3$): δ = 12.94 (s, 1H), 7.65 (dd, 1H, J$_1$ = 10.8 Hz, J$_2$ = 2.0 Hz), 6.97 (d, 2H, J = 8.8 Hz), 6.39 (brs, 1H), 5.30-5.24 (m, 2H), 4.33 (dd, 4H, J = 8.8, 5.2 Hz), 3.86 (s, 3H), 3.54 (d, 2H, J = 6.8 Hz), 3.45 (d, 2H, J = 6.9 Hz), 1.84 (s, 3H), 1.83 (s, 3H), 1.76 (s, 3H), 1.75 (s, 3H). | 479.4 [M + H]$^+$ |
| 21 | 2-(benzo[d][1,3]dioxo-5-yl)-5,7-dihydroxy-3-methoxy-6,8-di(3-methyl-2-buten-1-yl)-4H-benzopyran-4-one; | (400 MHz, CDCl$_3$): δ = 12.92 (s, 1H), 7.70 (dd, 1H, J$_1$ = 8.8 Hz, J$_2$ = 2.0 Hz), 7.59 (d, 1H, J = 1.6 Hz), 6.94 (d, 1H, J = 8.4 Hz), 6.33 (brs, 1H), 6.07 (s, 2H), 5.30-5.24 (m, 2H), 3.86 (s, 3H), 3.54 (d, 2H, J = 6.8 Hz), 3.46 (d, 2H, J = 6.8 Hz), 1.84 (s, 3H), 1.83 (s, 3H), 1.77 (s, 3H), 1.75 (s, 3H). | 464.8 [M + H]$^+$ |
| 22 | 2-(3-chloro-4-methoxyphenyl)-5,7-dihydroxy-3-methoxy-6,8-di(3-methyl-2-buten-1-yl)-4H-benzopyran-4-one; | (300 MHz, CDCl$_3$): δ = 8.11 (s, 3H), 8.06 (d, 1H, J = 9.0 Hz), 7.04 (d, 1H, J = 8.7 Hz), 6.35 (brs, 1H), 5.30-5.24 (m, 2H), 3.99 (s, 3H), 3.87 (s, 3H), 3.53 (d, 2H, J = 6.6 Hz), 3.46 (d, 2H, J = 6.9 Hz), 1.84 (s, 6H), 1.77 (s, 3H), 1.75 (s, 3H). | 485.1 [M + H]$^+$ |
| 23 | 2-(3-fluoro-4-ethoxylphenyl)-5,7-dihydroxy-3-methoxy-6,8-di(3-methyl-2-buten-1-yl)-4H-benzopyran-4-one; | (400 MHz, CDCl$_3$): δ = 12.89 (s, 1H), 7.92-7.85 (m, 2H), 7.05 (d, 1H, J = 8.4 Hz), 6.33 (brs, 1H), 5.30-5.24 (m, 2H), 4.21 (q, 2H, J = 7.2 Hz), 3.86 (s, 3H), 3.54 (d, 2H, J = 6.8 Hz), 3.46 (d, 2H, J = 6.8 Hz), 1.84 (s, 3H), 1.83 (s, 3H), 1.77 (s, 3H), 1.75 (s, 3H), 1.51 (t, 3H, J = 7.2 Hz). | 482.8 [M + H]$^+$ |
| 24 | 2-(4-ethoxyphenyl)-5,7-dihydroxy-3-methoxy-6,8-di(3-methyl-2-buten-1-yl)-4H-benzopyran-4-one; | (400 MHz, CDCl$_3$): δ = 12.98 (s, 1H), 8.07 (d, 2H, J = 8.8 Hz), 7.00 (d, 2H, J = 8.8 Hz), 6.31 (brs, 1H), 5.30-5.24 (m, 2H), 4.13 (q, 2H, J = 6.8 Hz), 3.86 (s, 3H), 3.54 (d, 2H, J = 6.8 Hz), 3.46 (d, 2H, J = 6.8 Hz), 1.85 (s, 3H), 1.83 (s, 3H), 1.77 (s, 3H), 1.75 (s, 3H), 1.46 (t, 3H, J = 6.8 Hz). | 465.2 [M + H]$^+$ |
| 25 | 2-(thiazol-5-yl)-5,7-dihydroxy-3-methoxy-6,8-di(3-methyl-2-buten-1-yl)-4H-benzopyran-4-one; | (400 MHz, CDCl$_3$): δ = 12.73 (s, 1H), 9.01 (s, 1H), 8.63 (s, 1H), 6.33 (brs, 1H), 5.30-5.24 (m, 2H), 4.06 (s, 3H), 3.56 (d, 2H, J = 6.8 Hz), 3.46 (d, 2H, J = 6.8 Hz), 1.87 (s, 3H), 1.85 (s, 3H). 1.77 (s, 3H), 1.75 (s, 3H). | 428.7 [M + H]$^+$ |
| 26 | 2-(6-methoxypyridin-3-yl)-5,7-dihydroxy-3-methoxy-6,8-di(3-methyl-2-buten-1-yl)-4H-benzopyran-4-one; | (400 MHz, CDCl$_3$): δ = 12.86 (s, 1H), 8.96 (s, 1H), 8.19 (dd, 1H, J$_1$ = 8.8 Hz, J$_2$ = 2.4 Hz), 6.88 (d, 1H, J = 8.8 Hz), 6.35 (brs, 1H), 5.30-5.24 (m, 2H), 4.03 (s, 3H), 3.90 (s, 3H), 3.54 (d, 2H, J = 7.2 Hz), 3.46 (d, 2H, | 452.5 [M + H]$^+$ |

TABLE 1-continued

| Compound No. | Compound name | $^1$H-NMR | LC-MS m/z (ESI) |
|---|---|---|---|
| 27 | 2-(2-methoxypyridin-4-yl)-5,7-dihydroxy-3-methoxy-6,8-di(3-methyl-2-buten-1-yl)-4H-benzopyran-4-one; | J = 7.2 Hz), 1.84 (s, 3H), 1.82 (s, 3H), 1.77 (s, 3H), 1.74 (s, 3H). (400 MHz, CDCl$_3$): δ = 12.72 (s, 1H), 8.31 (d, 1H, J = 5.6 Hz), 7.54 (dd, 1H, J$_1$ = 5.6 Hz, J$_2$ = 1.6 Hz), 7.41 (s, 1H), 6.43 (brs, 1H), 5.27-5.20 (m, 2H), 4.01 (s, 3H), 3.92 (s, 3H), 3.54 (d, 2H, J = 7.2 Hz), 3.46 (d, 2H, J = 7.2 Hz), 1.84 (s, 3H), 1.82 (s, 3H), 1.77 (s, 3H), 1.74 (s, 3H). | 451.8 [M + H]$^+$ |
| 28 | 2-(pyridin-3-yl)-5,7-dihydroxy-3-methoxy-6,8-di(3-methyl-2-buten-1-yl)-4H-benzopyran-4-one | (400 MHz, CDCl$_3$): δ = 12.78 (s, 1H), 9.03 (d, 1H, J = 1.6 Hz), 8.73 (dd, 1H, J$_1$ = 8.8 Hz, J$_2$ = 1.6 Hz), 8.40-8.37 (m, 1H), 7.49 (dd, 1H, J$_1$ = 8.0 Hz, J$_2$ = 4.8 Hz), 6.43 (brs, 1H), 5.27-5.20 (m, 2H), 3.93 (s, 3H), 3.54 (d, 2H, J = 7.2 Hz), 3.47 (d, 2H, J = 7.2 Hz), 1.85 (s, 3H), 1.82 (s, 3H), 1.77 (s, 3H), 1.74 (s, 3H). | 421.8 [M + H]$^+$ |
| 29 | 2-(pyridin-2-yl)-5,7-dihydroxy-3-methoxy-6,8-di(3-methyl-2-buten-1-yl)-4H-benzopyran-4-one | (400 MHz, CDCl$_3$): δ = 12.81 (s, 1H), 8.83-8.81 (m, 1H), 8.01 (d, 1H, J = 7.6 Hz), 7.84 (td, 1H, J$_1$ = 7.6 Hz, J$_2$ = 2.0 Hz), 7.49 (dd, 1H, J$_1$ = 8.0 Hz, J$_2$ = 4.8 Hz), 6.43 (brs, 1H), 5.29-5.25 (m, 2H), 3.92 (s, 3H), 3.57 (d, 2H, J = 6.8 Hz), 3.46 (d, 2H, J = 6.8 Hz), 1.85 (s, 3H), 1.78 (s, 3H), 1.77 (s, 3H), 1.72 (s, 3H). | 421.8 [M + H]$^+$ |
| 30 | 2-(piperazin-2-yl)-5,7-dihydroxy-3-methoxy-6,8-di(3-methyl-2-buten-1-yl)-4H-benzopyran-4-one | (400 MHz, CDCl$_3$): δ = 12.70 (s, 1H), 9.30 (d, 1H, J = 1.6 Hz), 8.79 (dd, 1H, J$_1$ = 3.0 Hz, J$_2$ = 1.6 Hz), 7.66 (d, 1H, J = 3.0 Hz), 6.46 (brs, 1H), 5.29-5.25 (m, 2H), 3.99 (s, 3H), 3.57 (d, 2H, J = 6.8 Hz), 3.46 (d, 2H, J = 6.8 Hz), 1.85 (s, 3H), 1.80 (s, 3H), 1.77 (s, 3H), 1.73 (s, 3H). | 422.7 [M + H]$^+$ |
| 31 | 2-(pyridin-4-yl)-5,7-dihydroxy-3-methoxy-6,8-di(3-methyl-2-buten-1-yl)-4H-benzopyran-4-one | (400 MHz, CDCl$_3$): δ = 12.70 (s, 1H), 8.80 (dd, 1H, J$_1$ = 4.8 Hz, J$_2$ = 1.6 Hz), 7.96 (dd, 1H, J$_1$ = 4.8 Hz, J$_2$ = 1.6 Hz), 6.45 (brs, 1H), 5.26-5.24 (m, 2H), 3.95 (s, 3H), 3.57 (d, 2H, J = 6.8 Hz), 3.46 (d, 2H, J = 6.8 Hz), 1.85 (s, 3H), 1.83 (s, 3H), 1.77 (s, 3H), 1.75 (s, 3H). | 421.9 [M + H]$^+$ |
| 32 | 2-(pyrimidin-5-yl)-5,7-dihydroxy-3-methoxy-6,8-di(3-methyl-2-buten-1-yl)-4H-benzopyran-4-one | (400 MHz, CDCl$_3$): δ = 12.65 (s, 1H), 9.42 (d, 2H, J = 2.4 Hz), 9.30 (s, 1H), 6.47 (brs, 1H), 5.26-5.19 (m, 2H), 4.00 (s, 3H), 3.53 (d, 2H, J = 6.8 Hz), 3.47 (d, 2H, J = 6.8 Hz), 1.85 (s, 3H), 1.83 (s, 3H), 1.77 (s, 3H), 1.75 (s, 3H). | 422.9 [M + H]$^+$ |
| 33 | 2-(pyrimidin-2-yl)-5,7-dihydroxy-3-methoxy-6,8-di(3-methyl-2-buten-1-yl)-4H-benzopyran-4-one | (400 MHz, CDCl$_3$): δ = 12.76 (s, 1H), 9.95 (d, 2H, J = 5.2 Hz), 7.40 (dd, 1H, J$_1$ = 9.6 Hz, J$_2$ = 4.2 Hz), 6.42 (brs, 1H), 5.27-5.26 (m, 2H), 4.01 (s, 3H), 3.54 (d, 2H, J = 6.8 Hz), 3.47 (d, 2H, J = 6.8 Hz), 1.76 (s, 6H), 1.74 (s, 3H), 1.71 (s, 3H). | 422.9 [M + H]$^+$ |
| 34 | 2-cyclopropyl-5,7-dihydroxy-3-methoxy-6,8-di(3-methyl-2-buten-1-yl)-4H-benzopyran-4-one | (400 MHz, CDCl$_3$): δ = 13.00 (s, 1H), 6.27 (brs, 1H), 5.22 (t, 1H, J = 7.2 Hz), 5.10 (t, 1H, J = 7.2 Hz), 3.92 (s, 3H), 3.43 (d, 2H, J = 6.8 Hz), 3.34 (d, 2H, J = 6.8 Hz), 2.47-2.43 (m, 1H), 1.83 (s, 3H), 1.80 (s, 3H), 1.76 (s, 3H), 1.72 (s, 3H), 1.28-1.11 (m, 4H). | 384.8 [M + H]$^+$ |
| 35 | 2-cyclobutyl-5,7-dihydroxy-3-methoxy-6,8-di(3-methyl-2-buten-1-yl)-4H-benzopyran-4-one | (400 MHz, CDCl$_3$): δ = 12.94 (s, 1H), 6.30 (brs, 1H), 5.26-5.22 (m, 2H), 3.99-3.97 (m, 1H), 3.82 (s, 3H), 3.54 (d, 2H, J = 6.8 Hz), 3.44 (d, 2H, J = 6.8 Hz), 2.49-2.44 (m, 2H), 2.30-2.27 (m, 2H), 2.20-2.05 (m, 1H), 2.03-1.96 (m, 1H), 1.86 (s, 3H), 1.84 (s, 3H), 1.76 (s, 3H), 1.74 (s, 3H). | 398.7 [M + H]$^+$ |

TABLE 1-continued

| Compound No. | Compound name | $^1$H-NMR | LC-MS m/z (ESI) |
|---|---|---|---|
| 36 | 2-cyclopentyl-5,7-dihydroxy-3-methoxy-6,8-di(3-methyl-2-buten-1-yl)-4H-benzopyran-4-one | (400 MHz, CDCl$_3$): δ = 12.94 (s, 1H), 6.26 (brs, 1H), 5.26-5.19 (m, 2H), 3.85 (s, 3H), 3.59-3.53 (m, 1H), 3.45 (d, 4H, J = 6.8 Hz), 2.02-1.98 (m, 2H), 1.98-1.85 (m, 6H), 1.83 (s, 3H), 1.80 (s, 3H), 1.76 (s, 3H), 1.73 (s, 3H). | 412.6 [M + H]$^+$ |
| 37 | 2-cyclohexyl-5,7-dihydroxy-3-methoxy-6,8-di(3-methyl-2-buten-1-yl)-4H-benzopyran-4-one | (400 MHz, CDCl$_3$): δ = 12.94 (s, 1H), 6.26 (brs, 1H), 5.23-5.22 (m, 2H), 3.86 (s, 3H), 3.47 (m, 2H, J = 7.2 Hz), 3.45 (m, 2H, J = 7.2 Hz), 3.14-3.08 (m, 1H), 1.98-1.80 (m, 4H), 1.83 (s, 6H), 1.75 (s, 3H), 1.74 (s, 3H), 1.68-1.57 (m, 2H), 1.46-1.23 (m, 4H). | 426.8 [M + H]$^+$ |
| 38 | 2-(terthydrofuran-3-yl)-5,7-dihydroxy-3-methoxy-6,8-di(3-methyl-2-buten-1-yl)-4H-benzopyran-4-one | (400 MHz, CDCl$_3$): δ = 12.80 (s, 1H), 6.34 (brs, 1H), 5.30-5.22 (m, 2H), 4.15 (t, 1H, J = 8.0 Hz), 4.06-4.01 (m, 1H), 3.98-3.94 (m, 2H), 3.89 (s, 3H), 3.89-3.85 (m, 1H), 3.44 (d, 4H, J = 7.2 Hz), 2.39-2.21 (m, 2H), 1.83 (s, 3H), 1.80 (s, 3H), 1.75 (s, 3H), 1.73 (s, 3H). | 415.6 [M + H]$^+$ |
| 39 | 2-(thiophen-2-yl)-5,7-dihydroxy-3-methoxy-6,8-di(3-methyl-2-buten-1-yl)-4H-benzopyran-4-one | (400 MHz, CDCl$_3$): δ = 12.88 (s, 1H), 7.90 (dd, 1H, J$_1$ = 4.0 Hz, J$_2$ = 1.2 Hz), 7.60 (dd, 1H, J$_1$ = 5.2 Hz, J$_2$ = 1.2 Hz), 7.20 (t, 1H, J = 4.0 Hz), 6.38 (brs, 1H), 5.30-5.24 (m, 2H), 4.00 (s, 3H), 3.57 (d, 2H, J = 6.8 Hz), 3.44 (d, 2H, J = 6.8 Hz), 1.85 (s, 3H), 1.83 (s, 3H), 1.77 (s, 3H), 1.75 (s, 3H). | 426.8 [M + H]$^+$ |
| 40 | 2-(thiophen-3-yl)-5,7-dihydroxy-3-methoxy-6,8-di(3-methyl-2-buten-1-yl)-4H-benzopyran-4-one | (400 MHz, CDCl$_3$): δ = 12.91 (s, 1H), 8.24 (dd, 1H, J$_1$ = 2.8 Hz, J$_2$ = 1.2 Hz), 7.77 (dd, 1H, J$_1$ = 2.8 Hz, J$_2$ = 1.2 Hz), 7.44 (dd, 1H, J$_1$ = 5.2 Hz, J$_2$ = 2.8 Hz), 6.36 (brs, 1H), 5.28-5.25 (m, 2H), 3.97 (s, 3H), 3.55 (d, 2H, J = 6.8 Hz), 3.44 (d, 2H, J = 6.8 Hz), 1.85 (s, 3H), 1.83 (s, 3H), 1.77 (s, 3H), 1.75 (s, 3H). | 426.7 [M + H]$^+$ |
| 41 | 2-(furan-2-yl)-5,7-dihydroxy-3-methoxy-6,8-di(3-methyl-2-buten-1-yl)-4H-benzopyran-4-one | (400 MHz, CDCl$_3$): δ = 12.88 (s, 1H), 7.68 (s, 1H), 7.29 (d, 1H, J = 2.8 Hz), 6.62 (t, 1H, J = 1.6 Hz), 6.37 (brs, 1H), 5.30-5.24 (m, 2H), 3.98 (s, 3H), 3.58 (d, 2H, J = 6.8 Hz), 3.44 (d, 2H, J = 6.8 Hz), 1.87 (s, 3H), 1.84 (s, 3H), 1.76 (s, 3H), 1.74 (s, 3H). | 410.7 [M + H]$^+$ |
| 42 | 2-(furan-3-yl)-5,7-dihydroxy-3-methoxy-6,8-di(3-methyl-2-buten-1-yl)-4H-benzopyran-4-one | (400 MHz, CDCl$_3$): δ = 12.91 (s, 1H), 8.24 (s, 1H), 7.56 (d, 1H, J = 3.2 Hz), 6.95 (d, 1H, J = 2.0 Hz), 6.33 (brs, 1H), 5.28-5.25 (m, 2H), 3.96 (s, 3H), 3.53 (d, 2H, J = 6.8 Hz), 3.44 (d, 2H, J = 6.8 Hz), 1.84 (s, 6H), 1.77 (s, 3H), 1.75 (s, 3H). | 410.7 [M + H]$^+$ |
| 43 | 2-(thiazol-4-yl)-5,7-dihydroxy-3-methoxy-6,8-di(3-methyl-2-buten-1-yl)-4H-benzopyran-4-one | (400 MHz, CDCl$_3$): δ = 12.81 (s, 1H), 8.97 (d, 1H, J = 2.0 Hz), 8.33 (d, 1H, J = 1.6 Hz), 6.42 (brs, 1H), 5.33-5.25 (m, 2H), 3.99 (s, 3H), 3.63 (d, 2H, J = 6.8 Hz), 3.45 (d, 2H, J = 6.8 Hz), 1.84 (s, 6H), 1.76 (s, 3H), 1.74 (s, 3H). | 427.8 [M + H]$^+$ |
| 44 | 2-(oxazol-4-yl)-5,7-dihydroxy-3-methoxy-6,8-di(3-methyl-2-buten-1-yl)-4H-benzopyran-4-one | (400 MHz, CDCl$_3$): δ = 12.78 (s, 1H), 8.46 (s, 1H), 8.06 (s, 1H), 6.44 (brs, 1H), 5.33-5.25 (m, 2H), 4.01 (s, 3H), 3.64 (d, 2H, J = 6.8 Hz), 3.45 (d, 2H, J = 6.8 Hz), 1.86 (s, 3H), 1.84 (s, 3H), 1.75 (s, 3H), 1.74 (s, 3H). | 411.73 [M + H]$^+$ |
| 45 | 2-(1-methyl-1H-pyrazol-5-yl)-5,7-dihydroxy-3-methoxy-6,8-di(3-methyl-2-buten-1-yl)-4H-benzopyran-4-one | (400 MHz, CDCl$_3$): δ = 12.79 (s, 1H), 7.60 (d, 1H, J = 2.0 Hz), 6.81 (d, 1H, J = 2.0 Hz), 6.32 (brs, 1H), 5.33-5.25 (m, 2H), 4.08 (s, 3H), | 424.8 [M + H]$^+$ |

TABLE 1-continued

| Compound No. | Compound name | $^1$H-NMR | LC-MS m/z (ESI) |
|---|---|---|---|
| | | 3.84 (s, 3H), 3.47 (d, 4H, J = 6.8 Hz), 1.84 (s, 3H), 1.77 (s, 3H), 1.76 (s, 3H), 1.72 (s, 3H). | |
| 46 | 2-(1-methyl-1H-pyrazol-4-yl)-5,7-dihydroxy-3-methoxy-6,8-di(3-methyl-2-buten-1-yl)-4H-benzopyran-4-one | (400 MHz, CDCl$_3$): δ = 12.98 (s, 1H), 8.06 (d, 2H, J = 5.2 Hz), 6.32 (brs, 1H), 5.33-5.25 (m, 2H), 4.01 (s, 3H), 3.96 (s, 3H), 3.54 (d, 2H, J = 6.8 Hz), 3.45 (d, 2H, J = 6.8 Hz), 1.85 (s, 3H), 1.84 (s, 3H), 1.76 (s, 3H), 1.74 (s, 3H). | 424.7 [M + H]$^+$ |
| 47 | 2-(1-methyl-1H-imidazol-2-yl)-5,7-dihydroxy-3-methoxy-6,8-di(3-methyl-2-buten-1-yl)-4H-benzopyran-4-one | (400 MHz, CDCl$_3$): δ = 12.73 (s, 1H), 7.27 (d, 1H, J = 8.0 Hz), 7.09 (s, 1H), 6.32 (brs, 1H), 5.26-5.17 (m, 2H), 3.82 (s, 3H), 3.74 (s, 3H), 3.48-3.44 (m, 4H), 1.84 (s, 3H), 1.81 (s, 3H), 1.76 (s, 3H), 1.71 (s, 3H). | 424.8 [M + H]$^+$ |
| 48 | 2-(1-methyl-1H-pyrazol-5-yl)-5,7-dihydroxy-3-methoxy-6,8-di(3-methyl-2-buten-1-yl)-4H-benzopyran-4-one | (400 MHz, CDCl$_3$): δ = 12.88 (s, 1H), 7.79 (s, 1H), 7.76 (s, 1H), 6.45 (brs, 1H), 5.25-5.12 (m, 2H), 3.90 (s, 3H), 3.87 (s, 3H), 3.47-3.45 (m, 4H), 1.84 (s, 3H), 1.77 (s, 6H), 1.72 (s, 3H). | 424.8 [M + H]$^+$ |
| 49 | 2-(benzo[b]thiazol-2-yl)-5,7-dihydroxy-3-methoxy-6,8-di(3-3-methyl-2-buten-1-yl)-4H-benzopyran-4-one | (400 MHz, CDCl$_3$): δ = 12.83 (s, 1H), 8.12 (s, 1H), 7.91-7.88 (m, 2H), 7.44-7.41 (s, 2H), 6.41 (brs, 1H), 5.33-5.27 (m, 2H), 4.09 (s, 3H), 3.63 (d, 2H, J = 7.2 Hz), 3.46 (d, 2H, J = 7.2 Hz), 1.92 (s, 3H), 1.85 (s, 3H), 1.77 (s, 6H). | 476.5 [M + H]$^+$ |
| 50 | 2-(benzofuran-2-yl)-5,7-dihydroxy-3-methoxy-6,8-di(3-methyl-2-buten-1-yl)-4H-benzopyran-4-one | (400 MHz, CDCl$_3$): δ = 12.85 (s, 1H), 7.71 (d, 1H, J = 8.0 Hz), 7.68 (s, 1H), 7.59 (d, 1H, J = 8.0 Hz), 7.43 (td, 1H, J$_1$ = 8.4 Hz, J$_2$ = 1.2 Hz), 7.32 (t, 1H, J = 8.0 Hz), 6.41 (brs, 1H), 5.36-5.26 (m, 2H), 4.08 (s, 3H), 3.64 (d, 2H, J = 7.2 Hz), 3.47 (d, 2H, J = 7.2 Hz), 1.95 (s, 3H), 1.85 (s, 3H), 1.78 (s, 3H), 1.76 (s, 3H). | 460.9 [M + H]$^+$ |
| 51 | 2-(2-fluoropyridin-4-yl)-5,7-dihydroxy-3-methoxy-6,8-di(3-methyl-2-buten-1-yl)-4H-benzopyran-4-one | (400 MHz, CDCl$_3$): δ = 12.62 (s, 1H), 8.38 (d, 1H, J = 5.2 Hz), 7.90-7.87 (m, 1H), 7.62 (s, 1H), 6.48 (brs, 1H), 5.28-5.20 (m, 2H), 3.98 (s, 3H), 3.54 (d, 2H, J = 7.2 Hz), 3.47 (d, 2H, J = 7.2 Hz), 1.85 (s, 3H), 1.84 (s, 3H), 1.78 (s, 3H), 1.76 (s, 3H). | 440.5 [M + H]$^+$ |
| 52 | 2-(6-chloropyridin-3-yl)-5,7-dihydroxy-3-methoxy-6,8-di(3-methyl-2-buten-1-yl)-4H-benzopyran-4-one | (400 MHz, CDCl$_3$): δ = 12.71 (s, 1H), 9.10 (dd, 1H, J$_1$ = 2.4 Hz, J$_2$ = 0.8 Hz), 8.35 (dd, 1H, J$_1$ = 8.4 Hz, J$_2$ = 2.4 Hz), 7.48 (dd, 1H, J$_1$ = 8.4 Hz, J$_2$ = 0.8 Hz), 6.42 (brs, 1H), 5.28-5.20 (m, 2H), 3.93 (s, 3H), 3.52 (d, 2H, J = 7.2 Hz), 3.47 (d, 2H, J = 7.2 Hz), 1.85 (s, 3H), 1.81 (s, 3H), 1.78 (s, 3H), 1.74 (s, 3H). | 456.0 [M + H]$^+$ |
| 53 | 2-(5-chloropyridin-2-yl)-5,7-dihydroxy-3-methoxy-6,8-di(3-3-methyl-2-buten-1-yl)-4H-benzopyran-4-one | (400 MHz, CDCl$_3$): δ = 12.75 (s, 1H), 8.76 (d, 1H, J = 2.0 Hz), 8.02 (d, 1H, 8.8 Hz), 7.82 (dd, 1H, J$_1$ = 8.8 Hz, J$_2$ = 6.0 Hz), 6.41 (brs, 1H), 5.26 (t, 2H, J = 2.0 Hz), 3.92 (s, 3H), 3.56 (d, 2H, J = 7.2 Hz), 3.47 (d, 2H, J = 7.2 Hz), 1.84 (s, 3H), 1.79 (s, 3H), 1.77 (s, 3H), 1.72 (s, 3H). | 456.0 [M + H]$^+$ |
| 54 | 2-(6-fluoropyridin-3-yl)-5,7-dihydroxy-3-methoxy-6,8-di(3-3-methyl-2-buten-1-yl)-4H-benzopyran-4-one | (400 MHz, CDCl$_3$): δ = 12.73 (s, 1H), 8.95 (d, 1H, J = 2.8 Hz), 8.53-8.47 (m, 1H), 7.09 (dd, 1H, J$_1$ = 9.2 Hz, J$_2$ = 3.2 Hz), 6.40 (brs, 1H), 5.28-5.20 (m, 2H), 3.93 (s, 3H), 3.52 (d, 2H, J = 7.2 Hz), 3.47 (d, 2H, J = 7.2 Hz), 1.85 (s, 3H), 1.81 (s, 3H), 1.78 (s, 3H), 1.74 (s, 3H). | 440.5 [M + H]$^+$ |

TABLE 1-continued

| Compound No. | Compound name | $^1$H-NMR | LC-MS m/z (ESI) |
|---|---|---|---|
| 55 | 2-(2-chloropyridin-4-yl)-5,7-dihydroxy-3-methoxy-6,8-di(3-methyl-2-buten-1-yl)-4H-benzopyran-4-one | (400 MHz, CDCl$_3$): δ = 12.62 (s, 1H), 8.55 (d, 1H, J = 5.2 Hz), 7.97 (s, 1H), 7.91 (dd, 1H, J$_1$ = 5.2 Hz, J$_2$ = 2.4 Hz), 6.47 (brs, 1H), 5.26-5.20 (m, 2H), 3.97 (s, 3H), 3.54 (d, 2H, J = 7.2 Hz), 3.47 (d, 2H, J = 7.2 Hz), 1.85 (s, 6H), 1.78 (s, 3H), 1.76 (s, 3H). | 456.0 [M + H]$^+$ |
| 56 | 4-[5,7-dihydroxy-3-methoxy-6,8-di(3-methyl-2-butenyl)-4-oxo-4H-benzopyran-2-yl]benzoic acid | (500 MHz, DMSO-d$_6$): δ = 13.25 (s, 1H), 12.74 (s, 1H), 9.83 (s, 1H), 8.11 (s, 4H), 5.15-5.12 (t, 2H, J = 8.0 Hz), 3.84 (s, 3H), 3.52 (d, 2H, J = 6.0 Hz), 3.32 (s, 2H), 1.74 (s, 3H), 1.70 (s, 3H), 1.64 (s, 6H). | 465.2 [M + H]$^+$ |
| 57 | 4-[5,7-dihydroxy-3-methoxy-6,8-di(3-methyl-2-butenyl)-4-oxo-4H-benzopyran-2-yl]benzonitrile; | (400 MHz, DMSO-d$_6$): δ = 12.67 (s, 1H), 9.86 (s, 1H), 8.15 (d, 2H, J = 8.0 Hz), 8.05 (d, 2H, J = 8.0 Hz), 5.14-5.08 (m, 2H), 3.83 (s, 3H), 3.50 (d, 2H, J = 6.4 Hz), 3.46 (d, 2H, J = 6.4 Hz), 1.73 (s, 3H), 1.68 (s, 3H), 1.62 (s, 6H). | 446.0 [M + H]$^+$ |
| 58 | 2-(4-trifluoromethoxyphenyl)-5,7-dihydroxy-3-methoxy-6,8-di(3-methyl-2-buten-1-yl)-4H-benzopyran-4-one | (400 MHz, DMSO-d$_6$): δ = 12.75 (s, 1H), 9.83 (s, 1H), 8.13 (d, 2H, J = 7.2 Hz), 7.57 (d, 2H, J = 8.0 Hz), 5.12 (m, 2H), 3.82 (s, 3H), 3.50 (d, 2H, J = 6.0 Hz), 3.33 (d, 2H, J = 6.0 Hz), 1.74 (s, 3H), 1.68 (s, 3H), 1.63 (s, 3H), 1.62 (s, 3H). | 505.0 [M + H]$^+$ |
| 59 | 2-(4-dimethylaminophenyl)-5,7-dihydroxy-3-methoxy-6,8-di(3-methyl-2-buten-1-yl)-4H-benzopyran-4-one | (400 MHz, DMSO-d$_6$): δ = 13.04 (s, 1H), 9.61 (s, 1H), 7.96 (d, 2H, J = 8.8 Hz), 6.84 (d, 2H, J = 9.2 Hz), 5.14-5.12 (m, 2H), 3.76 (s, 3H), 3.52 (d, 2H, J = 6.4 Hz), 3.40 (d, 2H, J = 6.4 Hz), 3.03 (s, 6H), 1.76 (s, 3H), 1.74 (s, 3H), 1.64 (s, 3H), 1.63 (s, 3H). | 464.1 [M + H]+ |
| 60 | 4-[5,7-dihydroxy-3-methoxy-6,8-di(3-methyl-2-buten-1-yl)-4-oxo-4H-benzopyran-2-yl]benzamide | (500 MHz, DMSO-d$_6$): δ = 12.76 (s, 1H), 9.83 (s, 1H), 8.15 (s, 1H), 8.06 (m, 4H), 7.56 (s, 1H), 5.15-5.12 (m, 2H), 3.83 (s, 3H), 3.52 (d, 2H, J = 6.0 Hz), 3.33 (d, 2H, J = 6.0 Hz), 1.75 (s, 3H), 1.71 (s, 3H), 1.65 (s, 3H), 1.64 (s, 3H). | 464.0 [M + H]$^+$ |
| 61 | 2-(4-fluoromethoxyphenyl)-5,7-dihydroxy-3-methoxy-6,8-di(3-methyl-2-buten-1-yl)-4H-benzopyran-4-one | (300 MHz, DMSO-d$_6$): δ = 12.81 (s, 1H), 9.81 (s, 1H), 8.08 (d, 2H, J = 9.0 Hz), 7.43 (d, 1H, J = 14.7 Hz), 7.43 (d, 2H, J = 9.0 Hz), 5.14 (m, 2H), 3.83 (s, 3H), 3.54 (d, 2H, J = 6.6 Hz), 3.39 (d, 2H, J = 6.6 Hz), 1.77 (s, 3H), 1.73 (s, 3H), 1.66 (s, 6H). | 487.0 [M + H]$^+$ |
| 62 | 2-[5,7-dihydroxy-3-methoxy-6,8-di(3-methyl-2-buten-1-yl)-4-oxo-4H-benzopyran-2-yl]benzenesulfonic acid | (400 MHz, DMSO-d$_6$): δ = 12.79 (s, 1H), 9.79 (s, 1H), 7.98 (d, 2H, J = 8.4 Hz), 7.74 (d, 2H, J = 8.8 Hz), 5.16-5.08 (m, 2H), 3.78 (s, 3H), 3.51 (d, 2H, J = 6.4 Hz), 3.32 (d, 2H, J = 6.4 Hz), 1.74 (s, 3H), 1.70 (s, 3H), 1.63 (s, 6H). | 500.9 [M + H]$^+$ |
| 63 | 4-[5,7-dihydroxy-3-methoxy-6,8-di(3-methyl-2-buten-1-yl)-4-oxo-4H-benzopyran-2-yl]benzene sulfonamide | (400 MHz, DMSO-d$_6$): δ = 12.72 (s, 1H), 9.85 (s, 1H), 8.16 (d, 2H, J = 9.2 Hz), 7.98 (d, 2H, J = 8.8 Hz), 7.54 (s, 2H), 5.15-5.09 (m, 2H), 3.82 (s, 3H), 3.51 (d, 2H, J = 6.4 Hz), 3.34 (d, 2H, J = 6.4 Hz), 1.74 (s, 3H), 1.70 (s, 3H), 1.63 (s, 6H). | 500.0 [M + H]$^+$ |
| 64 | 2-(4-methanesulfonylphenyl)5,7-dihydroxy-3-methoxy-6,8-di(3-methyl-2-buten-1-yl)-4H-benzopyran-4-one | (300 MHz, DMSO-d$_6$): δ = 12.73 (s, 1H), 9.90 (s, 1H), 8.26 (d, 2H, J = 8.7 Hz), 8.14 (d, 2H, J = 8.7 Hz), 5.16 (m, 2H), 3.88 (s, 3H), 3.55 (d, 2H, J = 6.3 Hz), 3.53-3.30 (m, 5H), 1.77 (s, 3H), 1.73 (s, 3H), 1.66 (s, 6H). | 499.1 [M + H]$^+$ |

TABLE 1-continued

| Compound No. | Compound name | $^1$H-NMR | LC-MS m/z (ESI) |
|---|---|---|---|
| 65 | 2-(4-acetylphenyl)-5,7-dihydroxy-3-methoxy-6,8-di(3-methyl-2-buten-1-yl)-4H-benzopyran-4-one | (300 MHz, DMSO-d$_6$): δ = 12.76 (s, 1H), 9.86 (s, 1H), 8.15 (s, 4H), 5.17 (m 2H), 3.86 (s, 3H), 3.61-3.28 (m, 4H), 2.68 (s, 3H), 1.77 (s, 3H), 1.73 (s, 3H), 1.66 (s, 6H). | 463.2 [M + H]$^+$ |
| 66 | 2-[4-(2-hydroxypropane-2-yl)phenyl)]-5,7-dihydroxy-3-methoxy-6,8-di(3-methyl-2-buten-1-yl)-4H-benzopyran-4-one | (300 MHz, DMSO-d$_6$): δ = 12.86 (s, 1H), 9.78 (s, 1H), 8.00 (d, 2H, J = 8.4 Hz), 7.67 (d, 2H, J = 8.4 Hz), 5.16 (m, 2H), 3.83 (s, 3H), 3.55 (d, 2H, J = 6.0 Hz), 3.35 (d, 2H, J = 6.6 Hz), 1.77 (s, 6H), 1.66 (s, 6H), 1.50 (s, 6H). | 479.0 [M + H]$^+$ |
| 67 | 2-[4-(1-hydroxyethyl)phenyl)]-5,7-dihydroxy-3-methoxy-6,8-di(3-methyl-2-buten-1-yl)-4H-benzopyran-4-one | (300 MHz, DMSO-d$_6$): δ = 12.86 (s, 1H), 9.79 (s, 1H), 8.00 (d, 2H, J = 8.4 Hz), 7.57 (d, 2H, J = 8.4 Hz), 5.17 (m, 2H), 4.85 (q, 1H), 3.93 (s, 3H), 3.55 (d, 2H, J = 6.0 Hz), 3.35 (d, 2H, J = 6.9 Hz), 1.76 (s, 3H), 1.74 (s, 3H), 1.61 (s, 6H), 1.28 (d, 3H, J = 9.3 Hz). | 465 [M + H]$^+$ |
| 68 | 2-(thiazol-5-yl)-5,7-dihydroxy-3-methoxy-6,8-di(3-methyl-2-buten-1-yl)-4H-benzopyran-4-one | (400 MHz, CDCl$_3$): δ = 12.73 (s, 1H), 9.00 (d, 1H, J = 2.0 Hz), 8.62 (d, 1H, J = 1.6 Hz), 5.36-5.24 (m, 2H), 4.06 (s, 3H), 3.56 (d, 2H, J = 6.8 Hz), 3.46 (d, 2H, J = 6.8 Hz), 1.87 (s, 6H), 1.78 (s, 3H), 1.75 (s, 3H). | 427.8 [M + H]$^+$ |
| 69 | 4-[5,7-dihydroxy-3-methoxy-6,8-di(3-methyl-2-buten-1-yl)-4-oxo-4H-benzopyran-2-yl]-N,N-dimethylbenzene sulfonamide | (300 MHz, DMSO-d$_6$): δ = 12.71 (s, 1H), 9.87 (s, 1H), 8.24 (d, 2H, J = 8.4 Hz), 7.94 (d, 2H, J = 8.4 Hz), 5.13 (m, 2H), 3.87 (s, 3H), 3.52 (d, 2H, J = 6.0 Hz), 3.35 (d, 2H, J = 6.9 Hz), 2.67 (s, 6H), 1.74 (s, 3H), 1.67 (s, 3H), 1.63 (s, 3H), 1.62 (s, 3H). | 528.1 [M + H]$^+$ |
| 70 | 4-[5,7-dihydroxy-3-methoxy-6,8-di(3-methyl-2-buten-1-yl)-4-oxo-4H-benzopyran-2-yl]N-methylbenzene sulfonamide | (300 MHz, DMSO-d$_6$): δ = 12.74 (s, 1H), 9.88 (s, 1H), 8.20 (d, 2H, J = 8.4 Hz), 7.94 (d, 2H, J = 8.4 Hz), 7.64 (brs, 1H), 5.14 (m, 2H), 3.87 (s, 3H), 3.52 (d, 2H, J = 6.0 Hz), 3.33 (d, 2H, J = 6.9 Hz), 2.52 (d, 1H, J = 5.1 Hz), 1.76 (s, 3H), 1.70 (s, 3H), 1.65 (s, 6H). | 514.2 [M + H]$^+$ |
| 71 | 2-[4-(trifluoromethylsulfonyl)phenyl]-5,7-dihydroxy-3-methoxy-6,8-di(3-methyl-2-buten-1-yl)-4H-benzopyran-4-one | (300 MHz, DMSO-d$_6$): δ = 12.64 (s, 1H), 9.94 (s, 1H), 8.41-8.32 (m, 4H), 5.14-5.11 (m, 2H), 3.91 (s, 3H), 3.50 (d, 2H, J = 6.0 Hz), 3.33 (d, 2H, J = 6.9 Hz), 1.74 (s, 3H), 1.70-1.68 (m, 9H). | 553.2 [M + H]$^+$ |
| 72 | 2-[4-(1H-1,2,4-triazol-1-yl)phenyl]-5,7-dihydroxy-3-methoxy-6,8-di(3-methyl-2-buten-1-yl)-4H-benzopyran-4-one | (300 MHz, DMSO-d$_6$): δ = 12.78 (s, 1H), 9.84 (s, 1H), 9.47 (s, 1H), 8.32 (s, 1H), 8.18 (d, 2H, J = 8.4 Hz), 8.09 (d, 2H, J = 8.4 Hz), 5.14 (m, 2H), 3.84 (s, 3H), 3.50 (d, 2H, J = 6.0 Hz), 3.34 (d, 2H, J = 6.9 Hz), 1.74 (s, 6H), 1.68 (s, 6H). | 488.2 [M + H]$^+$ |
| 73 | 2-(3,5-dichlorophenyl)-5,7-dihydroxy-3-methoxy-6,8-di(3-methyl-2-buten-1-yl)-4H-benzopyran-4-one | (300 MHz, DMSO-d$_6$): δ = 12.64 (s, 1H), 9.92 (s, 1H), 7.94 (s, 2H), 7.93 (s, 1H), 5.14-5.10 (m, 2H), 3.84 (s, 3H), 3.49 (d, 2H, J = 6.0 Hz), 3.34 (d, 2H, J = 6.9 Hz), 1.74 (s, 3H), 1.73 (s, 3H), 1.64 (s, 3H), 1.63 (s, 3H). | 490.0 [M + H]$^+$ |
| 74 | 2-(4-nitro-3-trifluoromethylphenyl)-5,7-dihydroxy-3-methoxy-6,8-di(3-methyl-2-buten-1-yl)-4H-benzopyran-4-one | (300 MHz, DMSO-d$_6$): δ = 12.63 (s, 1H), 9.97 (s, 1H), 8.50 (s, 1H), 8.50 (d, 2H, J = 7.2 Hz), 8.40 (d, 1H, J = 7.2 Hz), 5.14-5.10 (m, 2H), 3.89 (s, 3H), 3.49 (d, 2H, J = 6.0 Hz), 3.34 (d, 2H, J = 6.9 Hz), 1.74 (s, 3H), 1.68 (s, 3H), 1.67 (s, 3H), 1.66 (s, 3H). | 534.1 [M + H]$^+$ |
| 75 | 2-(3-methyl-4-hydroxyphenyl)-5,7-dihydroxy-3-methoxy-6,8-di(3-methyl-2-buten-1-yl)-4H-benzopyran-4-one | (300 MHz, DMSO-d$_6$): δ = 12.91 (s, 1H), 10.16 (s, 1H), 9.67 (s, 1H), 7.76 (d, 1H, J = 7.8 Hz), 6.93 (d, 1H, J = 7.8 Hz), 5.12-5.10 (m, 2H), 3.74 (s, 3H), 3.49 (d, 2H, | 451.2 [M + H]$^+$ |

TABLE 1-continued

| Compound No. | Compound name | $^1$H-NMR | LC-MS m/z (ESI) |
|---|---|---|---|
| 76 | 2-(3-chloro-4-hydroxyphenyl)-5,7-dihydroxy-3-methoxy-6,8-di(3-methyl-2-buten-1-yl)-4H-benzopyran-4-one | J = 6.0 Hz), 3.29 (d, 2H, J = 6.0 Hz), 1.71 (s, 6H), 1.61 (s, 6H). (300 MHz, CDCl$_3$): δ = 12.86 (s, 1H), 8.11 (d, 1H, J = 1.8 Hz), 7.99 (dd, 1H, J$_1$ = 8.8 Hz, J$_2$ = 1.8 Hz), 7.14 (d, 1H, J = 8.8 Hz), 6.36 (s, 1H), 5.94 (s, 1H), 5.28-5.22 (m, 2H), 3.87 (s, 3H), 3.54 (d, 2H, J = 6.8 Hz), 3.47 (d, 2H, J = 6.8 Hz), 1.84 (s, 3H), 1.83 (s, 3H), 1.76 (s, 3H), 1.74 (s, 3H). | 471.0 [M + H]$^+$ |
| 77 | 2-(3-trifluoromethyl-4-hydroxyphenyl)-5,7-dihydroxy-3-methoxy-6,8-di(3-methyl-2-buten-1-yl)-4H-benzopyran-4-one | (300 MHz, DMSO-d$_6$): δ = 12.82 (s, 1H), 11.45 (s, 1H), 9.76 (s, 1H), 8.17 (s, 1H), 8.14 (d, 1H, J = 7.8 Hz), 7.20 (d, 1H, J = 7.8 Hz), 5.13 (m, 2H), 3.80 (s, 3H), 3.49 (d, 2H, J = 6.0 Hz), 3.33 (d, 2H, J = 6.0 Hz), 1.75 (s, 3H), 1.74 (s, 3H), 1.72 (s, 3H), 1.71 (s, 3H). | 505.1 [M + H]$^+$ |
| 78 | 2-(3-hydroxy-4-fluorophenyl)-5,7-dihydroxy-3-methoxy-6,8-di(3-methyl-2-buten-1-yl)-4H-benzopyran-4-one | (300 MHz, DMSO-d$_6$): δ = 12.82 (s, 1H), 10.32 (s, 1H), 9.78 (s, 1H), 7.72 (dd, 1H, J$_1$ = 7.8 Hz, J$_2$ = 2.1 Hz), 7.48 (d, 1H, J = 2.1 Hz), 7.37 (dd, 1H, J$_1$ = 7.8 Hz, J$_2$ = 2.1 Hz), 5.15 (m, 2H), 3.80 (s, 3H), 3.49 (d, 2H, J = 6.0 Hz), 3.33 (d, 2H, J = 6.0 Hz), 1.75 (s, 3H), 1.74 (s, 3H), 1.71 (s, 6H). | 455.1 [M + H]$^+$ |
| 79 | 2-(3-fluoro-4-hydroxyphenyl)-5,7-dihydroxy-3-methoxy-6,8-di(3-methyl-2-buten-1-yl)-4H-benzopyran-4-one | (300 MHz, CDCl$_3$): δ = 12.84 (s, 1H), 7.92-7.84 (t, 1H, J = 13.2 Hz), 7.14 (d, 1H, J = 7.5 Hz), 6.36 (s, 1H), 5.90 (s, 1H), 5.25 (m, 2H), 3.86 (s, 3H), 3.54 (d, 2H, J = 6.0 Hz), 3.46 (d, 2H, J = 6.0 Hz), 1.83 (s, 6H), 1.76 (s, 6H). | 455.1 [M + H]$^+$ |
| 80 | 2-[4-trifluoromethylthiophenyl]-5,7-dihydroxy-3-methoxy-6,8-di(3-methyl-2-buten-1-yl)-4H-benzopyran-4-one | (400 MHz, CDCl$_3$): δ = 8.20 (d, 2H, J = 8.4 Hz), 7.77 (d, 2H, J = 8.4 Hz), 6.41 (brs, 1H), 5.28-5.20 (m, 2H), 3.54 (d, 2H, J = 7.2 Hz), 3.47 (d, 2H, J = 8.4 Hz), 1.85 (s, 3H), 1.82 (s, 3H), 1.76 (s, 6H). | 521.5 [M + H]$^+$ |

Example 81

2-(3,4-difluorophenyl)-5-hydroxy-3,7-dimethoxy-6,8-di(3-methyl-2-buten-1-yl)-4H-benzopyran-4-one (compound 81A) and 2-(3,4-difluorophenyl)-3,7-dimethoxy-6,8-di(3-methyl-2-buten-1-yl)-4H-benzopyran-4-one (compound 81B)

2-(3,4-difluorophenyl)-5,7-dihydroxy-3-methoxy-6,8-di(3-methyl-2-buten-1-yl)-4H-benzopyran-4-one (100 mg, 0.219 mmol) was dissolved in 30 mL acetone, and then anhydrous sodium carbonate powder (91 mg, 0.657 mmol) and dimethyl sulfate (55.3 mg, 0.438 mmol) were added. After reacting at 50° C. for 2 hours, the solvent was removed, and the residue was dissolved in 20 ml water and extracted with ethyl acetate three times. The combined organic phase was dried over anhydrous sodium sulfate and concentrated. The crude product was purified by the preparative TLC to give the compound 81A (29 mg, yield 28.1%) and compound 81B (28.7 mg, yield 27.8%).

Compound 81A: 1H NMR (400 MHz, CDCl$_3$): δ=12.57 (s, 1H), 7.98-7.91 (m, 2H), 7.30 (t, 1H, J=8.8 Hz), 5.24 (t, 1H, J=6.8 Hz), 5.19 (t, 1H, J=6.8 Hz), 3.89 (s, 3H), 3.79 (s, 3H), 3.54 (d, 2H, J=6.4 Hz), 3.41 (d, 2H, J=6.8 Hz), 1.83 (s, 3H), 1.81 (s, 3H), 1.73 (s, 3H), 1.69 (s, 3H); LC-MS (ESI) m/z 471.8 [M+H]+; compound 81B: 1H NMR (400 MHz, CDCl$_3$): δ=7.99-7.93 (m, 2H), 7.29 (t, 1H, J=8.8 Hz), 5.22=5.20 (m, 2H), 3.90 (s, 3H,), 3.89 (s, 3H,), 3.80 (s, 3H), 3.60 (d, 2H, J=5.2 Hz), 3.44 (d, 2H, J=6.8 Hz), 1.83 (s, 3H), 1.81 (s, 3H), 1.74 (s, 3H), 1.69 (s, 3H); LC-MS (ESI) m/z 485.8 [M+H]+.

Example 82

2-(3-fluoro-4-chlorophenyl)-5-hydroxy-3,7-dimethoxy-6,8-di(3-methyl-2-buten-1-yl)-4H-benzopyran-4-one (compound 82A) and 2-(3-fluoro-4-chlorophenyl)-3,5,7-trimethoxy-6,8-di(3-methyl-2-buten-1-yl)-4H-benzopyran-4-one (compound 82B)

Example 82 was prepared according to a method similar to that for preparation of compounds 81A and 81B. Compound 82A: 1H NMR (400 MHz, CDCl$_3$): δ=12.54 (s, 1H), 7.93-7.89 (m, 2H), 7.53 (t, 1H, J=8.8 Hz), 5.24 (t, 1H, J=6.8 Hz), 5.19 (t, 1H, J=6.8 Hz), 3.89 (s, 3H), 3.79 (s, 3H), 3.54 (d, 2H, J=6.4 Hz), 3.41 (d, 2H, J=6.8 Hz), 1.83 (s, 3H), 1.81 (s, 3H), 1.73 (s, 3H), 1.70 (s, 3H); LC-MS (ESI) m/z 487.9 [M+H]$^+$; compound 82B: 1H NMR (400 MHz, CDCl$_3$): δ=7.94-7.90 (m, 2H), 7.51 (t, 11-1, J=8.0 Hz), 5.23-5.20 (m, 2H), 3.90 (s, 6H), 3.80 (s, 3H), 3.60 (d, 2H, J=6.0 Hz), 3.45 (d, 2H, J=6.0 Hz), 1.84 (s, 3H), 1.81 (s, 3H), 1.75 (s, 3H), 1.68 (s, 3H); LC-MS (ESI) m/z 501.9 [M+H]$^+$.

Example 83

2-(3,4-difluorophenyl)-7-hydroxy-3,5-dimethoxy-6,8-di(3-methyl-2-buten-1-yl)-4H-benzopyran-4-one (compound 83)

Step 1: preparing 2-(3,4-difluorophenyl)-5-hydroxy-3-methoxy-6,8-di(3-methyl but-2-ene-1-yl)-4H-oxo-4H-benzopyran-7-hydroxyacetate 2-(3,4-difluorophenyl)-5,7-dihydroxy-3-methoxy-6,8-di (3-methyl-2-buten-1-yl)-4H-benzopyran-4-one (100 mg, 0.219 mmol) was dissolved in 30 mL pyridine, followed by adding acetic anhydride (26.8 mg, 0.263 mmol) at 0° C. The mixture was stirred at room temperature for 3 hours, then poured into an ice water, and extracted with ethyl acetate 3 times. The extract was dried over anhydrous sodium sulfate and concentrated. The crude product was purified by silica gel column chromatography to give the desired compound (80 mg, yield 73.3%).

Step 2: preparing 2-(3,4-difluorophenyl)-3,5-dimethoxy-6,8-di(3-methylbut-2-ene-1-yl)-4-oxo-4H-benzopyran-7-hydroxyacetate 2-(3,4-difluorophenyl)-5-hydroxy-3-methoxy-6,8-di(3-methylbut-2-ene-1-yl)-4-oxo-4H-benzopyran-7-hydroxyacetate (80 mg, 0.16 mmol) was dissolved in 30 mL acetone, and anhydrous sodium carbonate powder (111 mg, 0.802 mmol) and dimethyl sulfate (101 mg, 0.802 mmol) were added. After reacting at 50° C. for 2 hours, the solvent was removed, and the residue was dissolved in 20 ml water and extracted with ethyl acetate three times. The combined organic phase was dried over anhydrous sodium sulfate and concentrated. The crude product was purified by silica gel column chromatography to give the compound (50 mg, yield 60.8%)

Step 3: preparing 2-(3,4-difluorophenyl)-7-hydroxy-3,5-dimethoxy-6,8-di(3-methyl-2-buten-1-yl)-4H-benzopyran-4-one 2-(3,4-difluorophenyl)-3,5-dimethoxy-6,8-di(3-methyl-but-2-ene-1-yl)-4-oxo-4H-benzopyran-7-hydroxyacetate (50 mg, 0.098 mmol) was dissolved in a 30 mL mixed solvent (THF/MeOH/H$_2$O=2/1/1), and potassium hydroxide (82 mg, 1.463 mmol) was added. The mixture was reacted at 30° C. for 0.5 hr, acidified to pH 5-6 with a dilute hydrochloride and extracted with ethyl acetate 3 times. The combined organic phase was dried over anhydrous sodium sulfate and concentration. The crude product was purified by the preparative TCL to give the desired compound (35.5 mg, yield 77%). $^1$H NMR (400 MHz, CDCl$_3$): δ=7.98-7.87 (m, 2H), 7.29 (t, 1H, J=8.8 Hz), 6.29 (brs, 1H), 5.24-5.21 (m, 2H), 3.89 (s, 3H), 3.88 (s, 3H), 3.60 (d, 2H, J=6.8 Hz), 3.52 (d, 2H, J=7.2 Hz), 1.86 (s, 3H), 1.84 (s, 3H), 1.77 (s, 3H), 1.76 (s, 3H); LC-MS (ESI) m/z 471.0 [M+H]+.

Example 84

2-(3-fluoro-4-chlorophenyl)-7-hydroxy-3,5-dimethoxy-6,8-di(3-methyl-2-buten-1-yl)-4H-benzopyran-4-one (compound 84)

Compound of Example 84 was prepared according to Example 83. $^1$H NMR (400 MHz, DMSO-d$_6$): δ=9.8 (brs, 1H), 7.91-7.78 (m, 3H), 5.09-5.07 (m, 2H), 3.78 (s, 3H), 3.69 (s, 3H), 3.54 (d, 2H, J=6.0 Hz), 3.33 (d, 2H, J=6.0 Hz), 1.72 (s, 3H), 1.69 (s, 3H), 1.61 (s, 6H); LC-MS (ESI) m/z 487.9 [M+H]$^+$.

Example 85

2-(3,4-difluorophenyl)-5,7-dihydroxy-6,8-di(3-methyl-2-buten-1-yl)-4H-benzopyran-4-one (compound 85)

Step 1: preparing 2-(1-iminoethyl)phenyl-1,3,5-triol hydrochloride

Phloroglucin (13 g, 1031 mmol) was dissolved in ether (200 mL), to which were added anhydrous zinc chloride (6.5 g, 48 mmol) and methyl cyanide (15 g, 365 mmol) in an ice-bath. Dry HCl gas was introduced into the reaction mixture, with vigorous stirring for 5 hrs, during which the precipitates were formed. The precipitates were collected and filtered to give the desired compound (16.2 g, yield 77.2%).

Step 2: preparing 1-(2,4,6-trihydroxyphenyl)ethanone 16.2 g of 2-(1-iminoethyl)phenyl-1,3,5-triol hydrochloride was dissolved in water, and heated to reflux for 3 hours. The pink precipitate was collected after cooling and recrystallized in water to give the desired white compound (0.7 g, yield 20%).

Step 3: preparing 1-[2,4,6-trihydroxy-3,5-di(3-methyl-2-buten-1-yl)phenyl]ethanone 1-(2,4,6-trihydroxyphenyl)ethanone (2.0 mg, 11.9 mmol) was dissolved in a 5% potassium hydroxide aqueous solution (20 mL). After the mixture was cooled below 0° C., isopentenyl bromide (3.6 g, 24 mmol) was slowly added dropwise within 30 min. The reaction mixture was stirred at room temperature for 2 hours, then poured into an ice water and acidified to pH 2. The reaction mixture was extracted with ethyl acetate. The extract was collected and dried over anhydrous sodium sulfate. After removal of the solvent, the residue was purified by silica gel column chromatography (dichloromethane as eluent) to give the desired compound (0.7 g, yield 20%).

Step 4: preparing 2-(3,4-difluorophenyl)-5,7-dihydroxy-6,8-di(3-methyl-2-buten-1-yl)-4H-benzopyran-4-one Under nitrogen atmosphere, 1-[2,4,6-trihydroxy-3,5-di(3-methyl-2-buten-1-yl)phenyl]ethanone (300 mg, 0.986 mmol), anhydrous potassium carbonate powder (817 mg, 5.91 mmol), TBAB (tetrabutyl ammonium bromide, 477 mg, 1.47 mmol) and 3,4-difluorobenzoyl chloride (348 mg, 1.97 mmol) were dissolved in toluene (30 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) to give the desired compound (10 mg, yield 2.3%). $^1$H NMR (400 MHz, CDCl$_3$): δ=12.92 (s, 1H), 7.73-7.68 (m, 1H), 7.64-7.61 (m, 1H), 7.35-7.25 (m, 114), 6.59 (s, 1H), 6.42 (s, 1H), 5.27-5.24 (m, 2H), 3.54 (d, 2H, J=6.8 Hz), 3.47 (d, 2H, J=6.8 Hz), 1.85 (s, 6H), 1.78 (s, 3H), 1.76 (s, 3H); LC-MS (ESI) m/z 427.8 [M+H]$^+$.

Example 86

2-(3-fluoro-4-chlorophenyl)-5,7-dihydroxy-6,8-di(3-methyl-2-buten-1-yl)-4H-benzopyran-4-one (compound 86)

Under nitrogen atmosphere, 1-[2,4,6-trihydroxy-3,5-di(3-methyl-2-buten-1-yl)phenyl]ethanone (300 mg, 0.986 mmol), anhydrous potassium carbonate powder (817 mg, 5.91 mmol), TBAB (tetrabutyl ammonium bromide, 477 mg, 1.47 mmol) and 3-fluoro-4-chlorobenzoyl chloride (380 mg, 1.97 mmol) were dissolved in toluene (30 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) to give the desired compound (15 mg, yield 3.5%). $^1$H NMR (400 MHz, CDCl$_3$): δ=12.90 (s, 1H), 7.67-7.55 (m, 3H), 6.62 (s, 1H), 6.43 (s, 1H), 5.27-5.24 (m, 2H), 3.54 (d, 2H, J=6.8 Hz), 3.47 (d, 2H, J=6.8 Hz), 1.85 (s, 3H), 1.81 (s, 3H), 1.78 (s, 3H), 1.76 (s, 3H); LC-MS (ESI) m/z 473.6 [M+H]$^+$.

Example 87

2-(4-methylphenyl)-5,7-dihydroxy-6,8-di(3-methyl-2-buten-1-yl)-4H-benzopyran-4-one (compound 87)

Step 1: preparing 2,4-di(3-methyl-2-buten-1-yl)phenyl-1,3,5-triol

Phloroglucin (6.3 g, 50 mmol) was dissolved in dry 1,4-dioxane (250 mL). Boron trifluoride-ether complex (5.0 mL) was slowly added dropwise with stirring, and then 2-methylbutenol (8.6 g, 100 mmol) was added. The mixture was reacted at 50° C. for 6 hr, and ether (500 mL) was added after cooling. The reaction solution was washed with water 3 times, and the organic phase was dried over anhydrous magnesium sulfate. The crude product was purified by silica gel column chromatography (eluent:ethyl acetate/petroleum ether, 1:10) after the solvent was removed under reduced pressure, to give the desired compound as an oil (3.5 g, yield 27%). $^1$H NMR (300 MHz, CDCl$_3$) δ=5.97 (s, 1H), 5.28-5.20 (m, 2H), 3.36-3.32 (m, 4H), 1.82 (s, 6H), 1.81 (s, 6H); GC-MS 262 [M]$^+$.

Step 2: preparing 5,7-dihydroxy-6,8-di(3-methyl-2-buten-1-yl)-2-p-tolyl-4H-benzopyran-4-one A mixture of 2,4-di(3-methyl-2-buten-1-yl)phenyl-1,3,5-triol (1.30 g, 5 mmol) and ethyl 3-p-tolyl-3-oxo-propionate (1.03 g, 5 mmol) was reacted in a microwave reactor (temperature set at 240° C., 3 min). After cooling, the product was filtered, washed with ethyl acetate and dried to give the desired yellow compound (400 mg, yield 19.8%). $^1$H NMR (300 MHz, CDCl$_3$): δ=7.80 (d, 211, J=7.8 Hz), 7.34 (d, 2H, J=8.1 Hz), 6.65 (s, 1H), 6.37 (s, 1H), 5.33-5.26 (m, 2H), 3.60 (d, 2H, J=6.6 Hz), 3.48 (d, 2H, J=6.9 Hz), 2.46 (s, 3H), 1.87 (s, 6H), 1.79 (s, 3H), 1.77 (s, 3H); LC-MS (ESI) m/z 405.2 [M+H]+, 427.2 [M+Na]$^+$.

Compounds 88-92 were prepared according to Example 87 from intermediate 2,4-di(3-methyl-2-buten-1-yl)phenyl-1,3,5-triol. The details are shown below in Table 2.

TABLE 2

| Compound No. | Compound name | $^1$H-NMR | LC-MS m/z (ESI) |
| --- | --- | --- | --- |
| 88 | 2-(3,4-dichlorophenyl)-5,7-dihydroxy-6,8-di(3-methyl-2-buten-1-yl)-4H-benzopyran-4-one | (300 MHz, CDCl$_3$): δ = 7.97 (s, 1H), 7.70 (d, 1H, J = 8.1 Hz), 7.61 (d, 1H, J = 8.7 Hz), 6.64 (s, 1H), 6.45 (s, 1H), 5.31-5.26 (m, 2H), 3.57 (d, 2H, J = 6.6 Hz), 3.48 (d, 2H, J = 7.2 Hz), 1.88 (s, 6H), 1.80 (s, 3H), 1.78 (s, 3H). | 459.2 [M + H]$^+$; 481.1 [M + Na]$^+$. |
| 89 | 2-(4-fluorophenyl)-5,7-dihydroxy-6,8-di(3-methyl-2-buten-1-yl)-4H-benzopyran-4-one | (300 MHz, CDCl$_3$): δ = 7.90 (dd, 2H, J$_1$ = 8.7 Hz, J$_2$ = 5.1 Hz), 7.23 (dd, 2H, J$_1$ = 9.0 Hz, J$_2$ = 5.4 Hz), 6.62 (s, 1H), 6.40 (s, 1H), 5.33-5.26 (m, 2H), 3.59 (d, 2H, J = 6.6 Hz), 3.48 (d, 2H, J = 6.9 Hz), 1.86 (s, 6H), 1.79 (s, 3H), 1.77 (s, 3H). | 409.2 [M + H]$^+$; 431.1 [M + Na]$^+$. |
| 90 | 2-(3-chloro-4-trimethoxyphenyl)-5,7-dihydroxy-6,8-di(3-methyl-2butylene-1-yl)-4H-benzopyran-4-one | (300 MHz, CDCl$_3$): δ = 13.02 (s, 1H), 7.90 (s, 1H), 7.75 (d, 1H, J = 6.9 Hz), 7.04 (d, 1H, J = 8.4 Hz), 6.56 (s, 1H), 6.39 (s, 1H), 5.33-5.26 (m, 2H), 3.99 (s, 3H), 3.56 (d, 2H, J = 6.6 Hz), 3.46 (d, 2H, J = 7.2 Hz), 1.87 (s, 3H), 1.85 (s, 3H), 1.77 (s, 3H), 1.76 (s, 3H). | 455.1 [M + H]$^+$, 477.0 [M + Na]$^+$ |

TABLE 2-continued

| Compound No. | Compound name | ¹H-NMR | LC-MS m/z (ESI) |
|---|---|---|---|
| 91 | 2-(4-chlorophenyl)-5,7-dihydroxy-6,8-di(3-methyl-2-buten-1-yl)-4H-benzopyran-4-one | (300 MHz, CDCl$_3$): δ = 12.99 (s, 1H), 7.90 (d, 2H, J = 8.7 Hz), 7.50 (d, 2H, J = 8.4 Hz), 6.66 (s, 1H), 6.42 (s, 1H), 5.33-5.26 (m, 2H), 3.59 (d, 2H, J = 6.6 Hz), 3.48 (d, 2H, J = 6.9 Hz), 1.86 (s, 6H), 1.79 (s, 3H), 1.77 (s, 3H). | 425.2 [M + H]⁺. |
| 92 | 2-(pyridin-3-yl)-5,7-dihydroxy-6,8-di(3-methyl-2-buten-1-yl)-4H-benzopyran-4-one | (300 MHz, CDCl$_3$): δ = 12.90 (s, 1H), 9.15 (s, 1H), 8.78 (d, 1H, J = 4.2 Hz), 7.04 (d, 1H, J = 7.8 Hz), 7.51-7.47 (m, 1H), 6.70 (s, 1H), 6.46 (s, 1H), 5.33-5.26 (m, 2H), 3.57 (d, 2H, J = 6.6 Hz), 3.46 (d, 2H, J = 7.2 Hz), 1.85 (s, 6H), 1.78 (s, 3H), 1.75 (s, 3H). | 392.2 [M + H]⁺, 414.1 [M + Na]⁺ |

Example 93

2-(3,4-difluorophenyl)-3-methyl-5,7-dihydroxy-6,8-di(3-methyl-2-buten-1-yl)-4H-benzopyran-4-one (compound 93)

Step 1: preparing 2-(1-iminoethyl)phenyl-1,3,5-triol hydrochloride

Pyrogallol (6.3 g, 50 mmol) was dissolved in ether (100 mL), to which were added anhydrous zinc chloride (3.4 g, 25 mmol) and propionitrile (7.2 g, 130 mmol) in an ice-bath. Dry HCl gas was introduced into the reaction mixture, with vigorous stirring for 5 hrs, during which the precipitates were formed. The precipitates were collected and filtered to give the desired compound (7.8 g, yield 71.9%).

Step 2: preparing 1-(2,4,6-trihydroxyphenyl)propan-1-one 7.5 g of 2-(1-iminopropyl)phenyl-1,3,5-triol hydrochloride was dissolved in water, and heated to reflux for 3 hours. The red precipitate was collected after cooling and recrystallized in water to give the desired white compound (4.7 g, yield 76%).

Step 3: preparing 1-[2,4,6-trihydroxy-3,5-di(3-methyl-2-buten-1-yl)phenyl]propan-1-one 1-(2,4,6-trihydroxyphenyl)propan-1-one (2.0 g, 11.0 mmol) was dissolved in a 5% potassium hydroxide aqueous solution (20 mL). After the mixture was cooled below 0° C., isopentenyl bromide (3.3 g, 22 mmol) was slowly added dropwise within 30 min. The reaction mixture was stirred at room temperature for 2 hours, then poured into an ice water and acidified to pH 2. The reaction mixture was extracted with ethyl acetate. The extract was collected and dried over anhydrous sodium sulfate. After removal of solvent, The residue was purified by silica gel column chromatography (dichloromethane as eluent) to give the desired compound (0.63 g, yield 18%).

Step 4: preparing 2-(3,4-difluorophenyl)-3-methyl-5,7-dihydroxy-6,8-di(3-methyl-2-buten-1-yl)-4H-benzopyran-4-one Under nitrogen atmosphere, 1-[2,4,6-trihydroxy-3,5-di(3-methyl-2-buten-1-yl)phenyl]propan-1-one (300 mg, 0.943 mmol), anhydrous potassium carbonate powder (817 mg, 5.91 mmol), TBAB (tetrabutyl ammonium bromide, 477 mg, 1.47 mmol) and 3,4-difluorobenzoyl chloride (348 mg, 1.97 mmol) were dissolved in toluene (30 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) to give the desired compound (5 mg, yield 1.2%). ¹H NMR (400 MHz, CDCl$_3$): δ=13.18 (s, 1H), 7.50-7.45 (m, 1H), 7.41-7.37 (m, 1H), 7.34-7.28 (m, 1H), 6.35 (s, 1H), 5.29-5.17 (m, 2H), 3.46 (d, 2H, J=7.2 Hz), 3.44 (d, 2H, J=7.2 Hz), 2.14 (s, 3H), 1.84 (s, 3H), 1.77 (s, 3H), 1.72 (s, 6H); LC-MS (ESI) m/z 441.7 [M+H]⁺

Example 94

2-(3-fluoro-4-chlorophenyl)-3-methyl-5,7-dihydroxy-6,8-di(3-methyl-2-buten-1-yl)-4H-benzopyran-4-one (compound 94)

Under nitrogen atmosphere, 1-[2,4,6-trihydroxy-3,5-di(3-methyl-2-buten-1-yl)phenyl]propan-1-one (300 mg, 0.943 mmol), anhydrous potassium carbonate powder (817 mg, 5.91 mmol), TBAB (tetrabutyl ammonium bromide, 477 mg, 1.47 mmol) and 3-fluoro-4-chlorobenzoyl chloride (380 mg, 1.97 mmol) were dissolved in toluene (30 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) and recrystallized in ethanol to give the desired compound (8 mg, yield 1.9%). $^1$H NMR (400 MHz, CDCl$_3$): δ=13.10 (s, 1H), 7.56 (d, 1H, J=7.6 Hz), 7.43 (dd, 1H, J$_1$=9.6 Hz, J$_2$=1.6 Hz), 7.37 (d, 1H, J=1.6 Hz), 6.35 (s, 1H), 5.28-5.17 (m, 2H), 3.47 (d, 2H, J=7.2 Hz), 3.44 (d, 2H, J=7.2 Hz), 2.14 (s, 3H), 1.84 (s, 3H), 1.77 (s, 3H), 1.73 (s, 3H), 1.72 (s, 3H); LC-MS (ESI) m/z 457.9 [M+H]$^+$.

Example 95

2-(3,4-difluorophenyl)-3,5,7-trihydroxy-6,8-di(3-methyl-2-buten-1-yl)-4H-benzopyran-4-one (compound 95)

Step 1: preparing 2-benzyloxy-1-(2,4,6-trihydroxyphenyl)ethanone

Anhydrous aluminum trichloride (27.5 g, 206 mmol) was dissolved into 200 mL dichloromethane and cooled to −10° C. A solution of pyrogallol (20 g, 159 mmol) in ether was slowly added dropwise to the reaction mixture. After stirring 10 min at −10° C., a solution of benzyloxy acetyl chloride (26.4 g, 143 mmol) in dichloromethane (30 ml) was added dropwise. The reaction mixture was heated to 50° C. for 24 hours, and then cooled to room temperature. 1N HCl solution was carefully added to the mixture. The organic phase was separated and extracted with dichloromethane twice. The combined organic phase was washed with saturated brine and dried over anhydrous sodium sulfate. Yellow oil product was obtained after filtering and concentration, and further purified by silica gel column chromatography (eluent:methanol/dichloromethane, 1:200) to give the desired white compound (14 g, yield 32.2%).

Step 2: preparing 2-benzyloxy-1-(2,4,6-trihydroxyphenyl-3,5-di(3-methyl-2-buten-1-yl)phenylethanone 2-benzyloxy-1-(2,4,6-trihydroxyphenyl)ethanone (4.0 g, 14.5 mmol) was dissolved in a 5% potassium hydroxide aqueous solution (100 mL). After the mixture was cooled below 0° C., isopentenyl bromide (4.8 g, 32 mmol) was slowly added dropwise within 30 min. The reaction mixture was stirred at room temperature for 2 hours, then poured into an ice water and acidified to pH 3. The reaction mixture was extracted with ethyl acetate. The extract was collected and dried over anhydrous sodium sulfate. After removal of the solvent, the residue was purified by silica gel column chromatography (eluent: methanol/dichloromethane, 1:200) to give the desired compound (1.4 g, yield 23%).

Step 3: preparing 3-benzyloxy 2-(3,4-difluorophenyl)-5,7-dihydroxy-6,8-di(3-methyl-2-buten-1-yl)-4H-benzopyran-4-one Under nitrogen atmosphere, 2-benzyloxy-1-[2,4,6-trihydroxyphenyl-3,5-di(3-methyl-2-buten-1-yl)phenylethanone (900 mg, 2.19 mmol), anhydrous potassium carbonate powder (1.52 g, 10.96 mmol), TBAB (tetrabutyl ammonium bromide, 1.04 g, 3.22 mmol) and 3,4-difluorobenzoyl chloride (795 mg, 4.5 mmol) were dissolved in toluene (100 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) and recrystallized with ethanol to give the desired compound (130 mg, yield 11.1%).

Step 4: preparing 2-(3,4-difluorophenyl)-3,5,7-trihydroxy-6,8-di(3-methyl-2-buten-1-yl)-4H-benzopyran-4-one 3-benyloxy-2-(3,4-difluorophenyl)-5,7-dihydroxy-6,8-di(3-methyl-2-buten-1-yl)-4H-benzopyran-4-one (30 mg) was dissolved in 10 mL methanol, and 5% Pd/C (10 mg) was added. The reaction mixture was hydrogenated at 0° C. under atmospheric pressure for 5 hr. The mixture was filtered and the filtrate was concentrated. The residue was purified by silica gel column chromatography (eluent:methol/dichloromethane, 1:50) to give the desired compound (6 mg, yield 24%). $^1$H NMR (400 MHz, CDCl$_3$): δ=11.94 (s, 1H), 8.08-7.98 (m, 2H), 7.31 (dd, 1H, J$^1$=18.4 Hz, J2=8.8 Hz), 6.76 (s, 1H), 6.45 (s, 1H), 5.28-5.22 (m, 2H), 3.56 (d, 2H, J=6.8 Hz), 3.47 (d, 2H, J=7.2 Hz), 1.86 (s, 3H), 1.85 (s, 3H), 1.77 (s, 3H), 1.76 (s, 3H); LC-MS (ESI) m/z 442.9 [M+H]$^+$.

Example 96

2-(3-fluoro-4-chlorophenyl)-3,5,7-trihydroxy-6,8-di(3-methyl-2-buten-1-yl)-4H-benzopyran-4-one (compound 96)

Step 1: preparing 3-benzyloxy-2-(3-fluoro-4-chlorophenyl)-5,7-dihydroxy-6,8-di(3-methyl-2-buten-1-yl)-4H-benzopyran-4-one Under nitrogen atmosphere, 2-benzyloxy-1-[2,4,6-trihydroxyphenyl-3,5-di(3-methyl-2-buten-1-yl)]phenylethanone (700 mg, 1.71 mmol), anhydrous potassium carbonate powder (1.18 g, 8.55 mmol), TBAB (tetrabutyl ammonium bromide, 826 mg, 2.56 mmol) and 3-fluoro-4-chlorobenzoyl chloride (660 mg, 2.56 mmol) were dissolved in toluene (100 mL), and refluxed for 6 hours. After cooling, toluene was removed, and then water (20 mL) was added. The aqueous solution was extracted with ethyl acetate. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:50) and recrystallized in ethanol to give the desired compound (150 mg, yield 16%).

Step 2: preparing 2-(3-fluoro-4-chlorophenyl)-3,5,7-trihydroxy-6,8-di(3-methyl-2-buten-1-yl)-4H-benzopyran-4-one 3-benzyloxy-2-(3-fluoro-4-chlorophenyl)-5,7-dihydroxy-6,8-di(3-methyl-2-buten-1-yl)-4H-benzopyran-4-one was dissolved in 10 mL methanol, and 5% Pd/C (10 mg) was added. The reaction mixture was hydrogenated at 0° C. under atmospheric pressure for 5 hr. The mixture was tilted and the filtrate was concentrated. The residue was purified by silica gel column chrotomagraphy (eluent:methol/dichloromethane, 1:50) to give the desired compound (11.3 mg, yield 9.0%). $^1$H NMR (400 MHz, CDCl$_3$): δ=11.82 (s, 1H), 8.02-7.94 (m, 2H), 7.53 (dd, 1H, J1=8.4 Hz, J2=7.6 Hz), 6.80 (s, 1H), 6.46 (s, 1H), 5.27-5.24 (m, 2H), 3.56 (d, 2H, J=6.8 Hz), 3.47 (d, 2H, J=7.2 Hz), 1.86 (s, 3H), 1.81 (s, 3H), 1.78 (s, 3H), 1.76 (s, 3H); LC-MS (ESI) m/z 459.6 [M+H]$^+$.

Example 97

2-(4-fluorophenyl)-3,5,7-trihydroxy-6,8-di(3-methyl-2-buten-1-yl)-4H-benzopyran-4-one (compound 97)

Step 1: preparing 2-(4-fluorophenyl)-5,7-dihydroxy-3-methoxy-4H-benzopyran-4-one Under nitrogen atmosphere, 2-methoxy-1-(2,4,6-trihydroxyphenyl)ethanone (60 mg, 303.03 mmol), anhydrous potassium carbonate powder (250.9 g, 1.82 mmol), TBAB (tetrabutyl ammonium bromide, 145.9 mg, 454.52 mmol) and 4-fluorobenzoyl chloride (95.8 mg, 606 mmol) were dissolved in toluene (1200 mL), and refluxed for 6 hours. After cooling, toluene was removed, and then water (500 mL) was added. The aqueous solution was extracted with dichloromethane. The combined organic phase was washed with water and saturated brine, and dried over anhydrous sodium sulfate. A brown residue was obtained after removal of solvent. The residue was dissolved in a 5% potassium carbonate aqueous solution and heated to reflux for 2 hr. After cooling to ambient temperature, the mixture was acidified to pH 6 with 1N HCl solution, and extracted with dichloromethane three times. The combined organic phase was dried over anhydrous sodium sulfate, and the solvent was removed. The crude product was purified by silica gel column chromatography (eluent:ethyl acetate/petroleum ether, 1:5) and recrystallized in ethanol to give the desired compound (75 g, yield 81.9%).

Step 2: preparing 2-(4-fluorophenyl)-3,5,7-4H-benzopyran-4-one

Under nitrogen atmosphere, 2-(4-fluorophenyl)-5,7-dihydroxy-3-methoxy-4H-benzopyran-4-one (8 g, 26.49 mmol) was dissolved in dichloromethane (150 mL), and cooled below 0° C. Boron tribromide (19.8 g, 79.20 mmol) are slowly added dropwise to the mixture. The resulting mixture was reacted at room temperature for 4 hours, and then quenched with 80 mL ice water. The organic phase was separated, washed with saturated brine, and dried over anhydrous sodium sulfate. After filtering and concentrating, the residue was purified by silica gel column chromatography (eluent: ethyl acetate/petroleum ether, 1:3) to give the desired compound (5.5 g, yield 70.8%).

Step 3: 2-(4-fluorophenyl)-3,5,7-trihydroxy-6,8-di(3-methyl-2-buten-1yl)-4H-benzopyran-4-one Metal sodium (4.26 g, 185 mmol) was added to methol (20 mL) and the resulting mixture was stirred at room temperature for 30 minutes until sodium was completely depleted. Then a solution of 2-(4-fluorophenyl)-3,5,7-trihydroxy-4H-benzopyran-4-one (5.3 g, 18.40 mmol) in methol (20 ml) was slowly added dropwise at 0° C., and the addition was finished in 30 minutes. The reaction mixture was kept stirring at room temperature for 1 hour, and then acidified to pH 7.0 with 1N HCl solution. The solvent was evaporated. The residue was extracted with ethylacetate three times. The combined organic phase was dried over anhydrous sodium sulfate and the solvent was removed. The crude product was purified by silica gel column chromatography (eluent:ethyl acetate/petroleum ether=1:250) and recrystallized with n-hexane, to give the desired yellow compound (510 mg, yield 6.5%). $^1$H NMR (300 MHz, DMSO-d$_6$): δ=12.59 (s, 1H), 9.74 (s, 2H), 8.20 (dd, 211, J$_1$=9.0 Hz, J$_2$=5.7 Hz), 7.43 (t, 2H, J=9.0 Hz), 5.18 (m, 2H), 3.56 (d, 2H, J=6.3 Hz), 3.35 (d, 2H, J=6.3 Hz), 1.76 (s, 6H), 1.56 (s, 6H); LC-MS (ESI) m/z 425 [M+H]$^+$.

Example 98

2-(4-trifluoromethylphenyl)-3,5,7-trihydroxy-6,8-di(3-methyl-2-buten-1-yl)-4H-benzopyran-4-one (compound 98)

Step 1: preparing [3-methoxy-6,8-di(3-methyl-2-buten-1-yl)-4-oxo-2-(4-trifluoromethylphenyl)-4H-benzopyran-5,7-diyl]di(4-methylbenzene sulfonate)

2-(4-trifluoromethylphenyl)-5,7-dihydroxy-3-methoxy-6,8-di(3-methyl-2-buten-1-yl)-4H-benzopyran-4-one (2.44 g, 5 mmol), TsCl (2.38 g, 12.5 mmol) and anhydrous potassium carbonate powder (250.9 g, 1.82 mmol) were dissolved in acetone (120 ml). The mixture was heated to reflux until the starting materials were completely depleted as shown by TCL. The reaction solution was poured into a dilute hydrochloric acid solution and extracted with ethyl acetate. The combined organic phase was dried over anhydrous sodium sulfate, and the solvent was removed, giving the desired white compound which can be used in the next reaction without further purification. LC-MS: m/z 797.0 [M+H]$^+$.

Step 2: [3-hydroxy-6,8-di(3-methyl-2-buten-1-yl)-4-oxo-2-(4-trifluoromethylphenyl)-4H-benzo pyran-5,7-diyl]di(4-methylbenzene sulfonate)

To a solution of aluminum tribromide (6.0 g, 22.5 mmol) in a dry acetonitrile (125 ml) was added [3-methoxy-6,8-di(3-methyl-2-buten-1-yl)-4-oxo-2-(4-trifluoromethylphenyl)-4H-benzopyran-5,7-diyl]di(4-methylbenzene sulfonate) (4.0 g, 5 mmol). The reaction mixture was stirred at RT for 2 hours, pourED into a diluent hydrochloric acid solution and extracted with ethylacetate. The combined organic phase was dried over anhydrous sodium sulfate and the solvent was removed. The residue was purified by silica gel column chromatography (eluent:ethyl acetate/petroleum ether=1:15), to give desired light yellow compound (1.7 g, yield 43.4%). LC-MS: m/z 783.0 [M+H]$^+$.

Step 3: preparing 2-(4-trifluoromethylphenyl)-3,5,7-trihydroxy-6,8-di(3-methyl-2-buten-1-yl)-4H-benzopyran-4-one

[3-hydroxy-6,8-di(3-methyl-2-buten-1-yl)-4-oxo-2-(4-trifluoromethylphenyl)-4H-benzopyran-5,7-diyl]di(4-methylbenzene sulfonate) (783 mg, 1 mmol) was dissolved in methanol (30 ml), and potassium carbonate (4.0 g, 28.9 mmol) was added. The reaction mixture was heated to reflux for 2 hours, then poured into a diluent hydrochloric acid solution and extracted with ethyl acetate. The combined organic phase was dried over anhydrous sodium sulfate and the solvent was removed. The residue was purified by silica gel column chromatography (eluent:ethyl acetate/petroleum ether=1:30), to give desired light yellow compound (241 mg, yield 50.8%). $^1$H NMR (400 MHz, CDCl$_3$): δ=11.76 (s, 1H), 8.26 (d, 2H, J=8.4 Hz), 7.71 (d, 2H, J=8.8 Hz), 6.75 (s, 1H), 6.40 (s, 1H), 5.20-5.18 (m, 2H), 3.53 (d, 2H, $J_1$=7.2 Hz), 3.40 (d, 2H, $J_2$=7.2 Hz), 1.79 (s, 6H), 1.71 (s, 3H), 1.69 (s, 3H); LC-MS (ESI) m/z 475.0 [M+H]$^+$.

Compounds 99 to 113 were prepared according to Examples 95-98 from intermediate 2,4-di(3-methyl-2-buten-1-yl)phenyl-1,3,5-triol as a starting material. The details are shown below in Table 3.

TABLE 3

| Compound No. | Compound name | LC-MS m/z (ESI) |
|---|---|---|
| 99 | 2-(4-cyanophenyl)-3,5,7-trihydroxy-6,8-di(3-methyl-2-buten-1-yl)-4H-benzopyran-4-one | 432.2 [M + H]$^-$. |
| 100 | 2-(4-chlorophenyl)-3,5,7-trihydroxy-6,8-di(3-methyl-2-buten-1-yl)-4H-benzopyran-4-one | 441.1 [M + H]$^+$. |
| 101 | 2-(3,4-dichlorophenyl)-3,5,7-trihydroxy-6,8-di(3-methyl-2-buten-1-yl)-4H-benzopyran-4-one | 475.8 [M + H]$^+$. |
| 102 | 2-(3,5-dichlorophenyl)-3,5,7-trihydroxy-6,8-di(3-methyl-2-buten-1-yl)-4H-benzopyran-4-one | 475.8 [M + H]$^+$. |
| 103 | 4-[3,5,7-trihydroxy-6,8-di(3-methyl-2-buten-1-yl)-4-oxo-4H-benzopyran-2-yl]benzonic acid | 451.6 [M + H]$^+$. |
| 104 | 4-[3,5,7-trihydroxy-6,8-di(3-methyl-2-buten-1-yl)-4-oxo-4H-benzopyran-2-yl]benzenesulfonic acid | 487.5 [M + H]$^+$. |
| 105 | 4-[3,5,7-trihydroxy-6,8-di(3-methyl-2-buten-1-yl)-4-oxo-4H-benzopyran-2-yl] benzamide | 450.3 [M + H]$^+$. |
| 106 | 4-[3,5,7-trihydroxy-6,8-di(3-methyl-2-buten-1-yl)-4-oxo-4H-benzopyran-2-yl]benzene sulfonamide | 486.6 [M + H]$^+$. |
| 107 | 4-[3,5,7-trihydroxy-6,8-di(3-methyl-2-buten-1-yl)-4-oxo-4H-benzopyran-2-yl]-N-methylbenzene sulfonamide | 500.2 [M + H]$^+$ |
| 108 | 4-[3,5,7-trihydroxy-6,8-di(3-methyl-2-buten-1-yl)-4-oxo-4H-benzopyran-2-yl]-N,N-dimethylbenzene sulfonamide | 514.4 [M + H]$^+$ |
| 109 | 2-(4-aminophenyl)-3,5,7-trihydroxy-6,8-di(3-methyl-2-buten-1-yl)-4H-benzopyran-4-one | 422.5 [M + H]$^+$ |
| 110 | 2-(4-dimethylaminophenyl)-3,5,7-trihydroxy-6,8-di(3-methyl-2-buten-1-yl)-4H-benzopyran-4-one | 450.6 [M + H]$^+$. |
| 111 | 2-(4-(trifluoromethylsulfonyl)phenyl)-3,5,7-trimethoxy-6,8-di(3-methyl-2-buten-1-yl)-4H-benzopyran-4-one | 539.8 [M + H]+. |
| 112 | 2-[4-(2-methyl-2H-tetrazol-5-yl)phenyl]-3,5,7-trihydroxy-6,8-di(3-methyl-2-buten-1-yl)-4H-benzopyran-4-one | 475.4 [M + H]+. |
| 113 | 2-[4-(1H-1,2,4-triazol-1-yl)phenyl]-3,5,7-trihydroxy-6,8-di(3-methyl-2-buten-1-yl)-4H-benzopyran-4-one | 474.1 [M + H]+. |

Bioactivity Assay

Activities of the compound of formula (I) of the present invention are demonstrated by the following assays.

Example 114

Expression of ER-α variants in Human Breast Cancer Specimens

A membrane pre-coated with human breast cancer tissues was purchased from ProSci Incorporated (Poway, Calif.). The membrane was probed with an anti-ER-α36 antibody that specifically recognizes ER-α36 and an HRP-conjugated secondary antibody, and visualized by enhanced chemiluminescence (ECL) detection reagents (Amersham Pharmacia Biotech). The same membrane was then eluted and detected with an anti-estrogen receptor-α antibody H222 (Novocastra Laboratories Ltd, UK) that recognizes all three subtypes of ER-α, i.e., ER-α66, ER-α46 and ER-α36. FIG. 1 shows that ER-α66, ER-α46 and ER-α36 are not expressed in normal breast tissue (Lane 1) but expressed in one specimen of infiltrating ductal carcinoma (Lane 2), one specimen of infiltrating lobular carcinoma (Lane 5) and non-invasive ductal carcinoma (Lane 7). In addition, ER-α36 is expressed in both invasive ductal caarcinoma (Lane 4) and another specimen of infiltrating lobular carcinoma (Lane 6). Lanes 2 and 3 are from the infiltrating ductal carcinoma tissues of two different patients, respectively. Lanes 5 and 6 are from the infiltrating lobular carcinoma tissue of two different patients, respectively. The results indicate that ER-α36 is not expressed in normal breast tissue, but expressed in ER-negative breast cancer samples that do not express ER-α66 and ER-α46.

Example 115

Expression of ER-α36 in ER-negative Breast Cancer Cell Line MDA-MB-231

Figure 2:
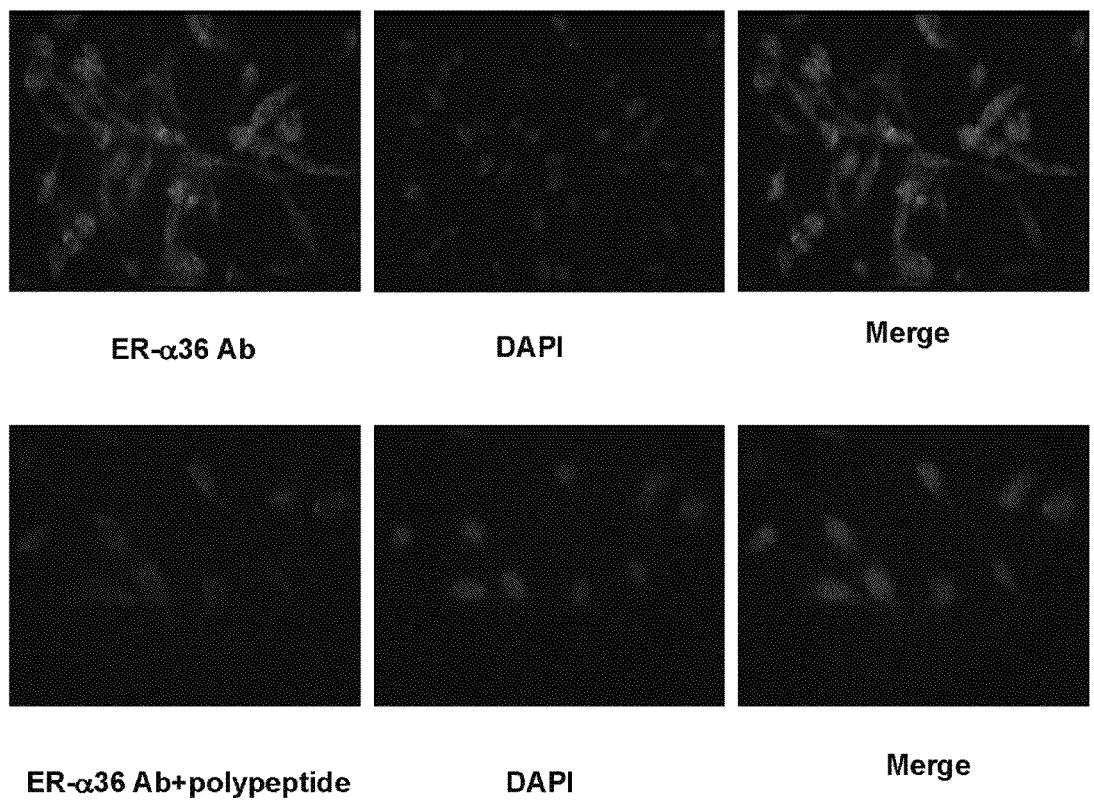
FIG. 2 (upper figure) shows an immunofluorescence staining result of MDA-MB-231 cell which is an ER-negative breast cancer cell line that lacks ER-α66 and ER-α46, stained with an antibody that specifically binds to ER-α36 (the left figure labeled with "ER-α36 Ab": positive staining shown in green). Cell nucleus was also stained with 4,6-diamidine-2-phenylindole (the middle figure labeled with "DAPI": positive staining shown in blue). Merged staining signals were labeled with "Merge" in the right figure. The result was shown as negative when the antibody was preincubated with immunogenic polypeptides bound to the antibody (lower figure).

MDA-MB-231 cell line is known to lack ER-α66 and ER-α46 (see Relevance of breast cancer cell lines as models for breast tumors: an update. Marc Lacroix, Guy Leclercq, Breast Cancer Research and Treatment 83: 249-289 (2004)). MDA-MB-231 cells were obtained from American Type Cell Culture (ATCC). MDA-MB-231 cells were incubated on 8-well BIOCOAT glass slide (BD Science Discovery Labware) containing Dulbecco's Modified Eagles Medium (DMEM) and 10% fetal calf serum, under $CO_2$ atmosphere at 37° C. for 12 hours. Then, the cells were washed twice with sterile Phosphate Buffered Saline (PBS), and fixed with 4% paraformaldehyde solution in PBS (pH 7.4) at room temperature for 30 minutes. Subsequently, the cells were washed with PBS, and permeabilized with 0.5% (v/v) Triton X-100 for 10 minutes. The cells were then rinsed with PBS again, to which was added 3% serum solution in PBS, and blocked at room temperature for 1 hour. The glass slide was incubated with an ER-α36 specific antibody or the same antibody preincubated with an immunogen peptide that binds to the antibody for 30 minutes, at room temperature for 1 hour and washed three times with PBS containing 0.5% Triton X-100 (PBST), then incubated with a fluorescein isothiocyanate (FITC)-conjugated secondary antibody. Finally, the glass slide was rinsed with PBST (3×) and PBS (1×), then coated with an immunofluorescent labeling (Molecular Probes, Eugene, Oreg.) and detected under Nikon E600 Microscope. The images were captured by a MRC-1024 confocal imaging system (Bio-Rad). FIG. 2 (upper panel) shows a positive result presented upon staining of MDA-MB-231 by an anti-ER-α36 antibody. In order to confirm the confidence level of the assay, incubation with the same antibody preincubated with the immunogen peptide did not show any staining (FIG. 2, lower panel), indicating the specificity of the antibody.

Example 116

Figure 3:
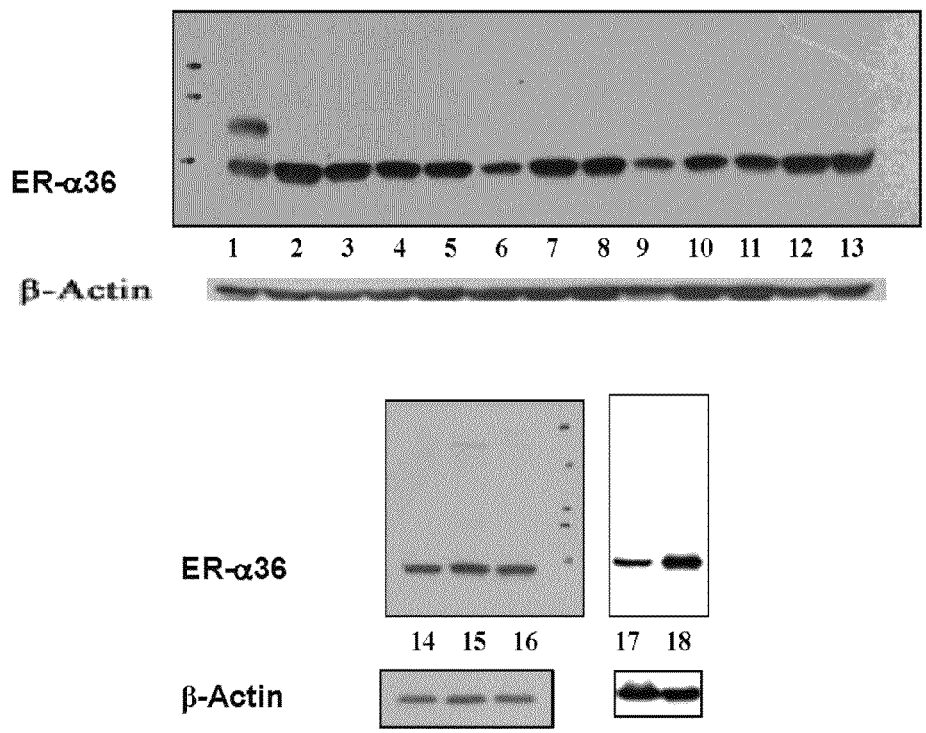
FIG. 3 shows Western blot results depicting the expression of ER-α36 in different tumor cell lines. Lane 1: 293 human renal epithelial cell lines for transient over-expression of ER-α36; Lane 2-4: human breast cancer cell line SK-BR-3 from different labs; Lane 5-7: human breast cancer cell line MCF-7 from different labs; Lane 8-9: human leukemia cell line HL-60 from different labs; Lane 10-11: human leukemia cell line MV-4-11 from different labs; Lane 12-13: human chronic granulocytic leukemia cell line K562 from different labs; Lane 14: human liver cancer cell line A2780; Lane 15: human liver cancer cell line HEL-7402; Lane 15: human liver cancer cell line 7402; Lane 16: human liver cancer cell cancer HEL-9204; Lane 17: liver cancer primary cell line Hep-11 from a patient; Lane 18: liver cancer primary cell line Hep-12 from a patient.

Expression of ER-α36 in Different Tumor Cell Lines as Detected by Western Blot Detection The cells were cultured at 37° C. 5% $CO_2$ (MDA-MB-231, and the culture medium is 10% FBS-DMEM). Once the cells of each well reach 60-90% confluence, the cells were collected and centrifuged at 4° C., 4300 rpm for 5 min. After removing supernatant, a suitable amount of lysate and Lysis buffer containing 1% NP-40 and 0.7 mM EDTA were added, followed by addition of a protease inhibitor, and then lysised for 30 min to 1 hr in an ice-bath. Centrifugation was performed again for 15 min at 14000 rpm, supernatant was removed, and protein was quantified. General procedure of western blot: transmembraning on prefabricated glue or self-formulated gule, electrophoresis, blocking anti-ER α-36 antibody, eluting, blocking secondary antibody, eluting, expressing exposure in a photographic laboratory and showing results. FIG. 3 shows Western blot result of Expression of ER-α in different tumor cells.

Lane 1: 293 human renal epithelial cell lines of transient over-expression of ER-α36; Lane 2-4: human breast cancer SK-BR-3 cell lines from different labs; Lane 5-7: human breast cancer MCF-7 cell lines from different labs; Lane 8-9: human leukemia HL-60 cell lines from different labs; Lane 10-11: human leukemia MV-4-11 cell lines from different labs; Lane 12-13: human chronic myeloid leukemia K562 cells from different labs; Lane 14: human liver cancer A2780 cell; Lane 15: human liver cancer HEL-7402 cell; Lane 16: human liver cancer HEL-9204 cell; Lane 17: primary cell line Hep-11 of liver cancer from a patient; Lane 18: primary liver cancer Hep-12 cell from a patient.

Example 117

Inhibition of the Compounds on In Vitro Growth of Different Breast Cancer Cells

A: In Vitro CellTiter-Glo® Luminescent Cell Viability Assay on ER-Negative Breast Cancer MDA-MB-231 Cells:

MDA-MB-231 cells were maintained at 37° C., under 5% $CO_2$ atmosphere in DMEM containing 10% fetal calf serum. The cells were seeded on 96-well plate at a density of $6\times10^3$ cells per well. MDA-MB-231 cells were treated with a test compound dissolved in DMSO at the concentrations of zero, 0.3 µM, 0.5 µM, 1 µM, 2 µM, 3 µM, 5 µM, 10 µM, 20 µM, 30 µM, 50 µM and 100 µM for 72 hours. Treated cells were examined by CellTiter-Glo® Luminescent Cell Viability Assay Kit (Promega), and luminescence values were recorded with Envision.

B: In Vitro CellTiter-Glo® Luminescent Cell Viability Assay on ER-Positive Breast Cancer MCF-7 Cells:

MCF7 cells are breast cancer cell lines that highly express ER-66, ER-46 and ER-36. (Relevance of breast cancer cell lines as models for breast tumours: an update. Marc Lacroix, Guy Leclercq, Breast Cancer Research and Treatment (2004) 83, 249-289; Wang et al., Proc. Natl. Acad. Sci. U.S.A. 103: 9063-9068 (2006)). MCF7 cells were obtained from ATCC and maintained in Dulbecco's Modified Eagles Medium (DMEM) and 10% fetal calf serum at 37° C., under 5% $CO_2$ atmosphere. The cells were seeded on 96-well plate at a density of $6\times10^3$ cells per well. MCF7 cells were treated with a test compound dissolved in DMSO at the concentrations of zero, 0.3 µM, 0.5 µM, 1 µM, 2 µM, 3 µM, 5 µM, 10 µM, 20 µM, 30 µM, 50 µM and 100 µM for 72 hours. Treated cells were examined by CellTiter-Glo® Luminescent Cell Viability Assay Kit (Promega), and luminescence values were recorded with Envision.

The effects of some of the present compounds in inhibiting the viability of different breast cancer cells are shown below in Table 4.

TABLE 4

| | Inhibition of the viability of breast cancer cells, $IC_{50}$ (µM) | |
|---|---|---|
| Compound No. | MDA-MB-231 cells | MCF7 cells |
| Tamoxifen[a] | 20.90 ± 1.51b) | 22.55 ± 4.15 |
| 1 | 14.20 ± 5.18 | 15.98 ± 158 |
| 2 | 11.32 ± 1.38 | 6.51 ± 1.42 |
| 3 | 12.60 ± 2.40 | 10.43 ± 0.22 |
| 4 | 6.37 ± 0.03 | 4.95 ± 0.65 |
| 5 | 7.03 ± 1.06 | 6.729 ± 1.58 |
| 6 | 7.06 ± 2.13 | 5.14 ± 0.47 |
| 7 | 10.91 ± 2.22 | 12.57 ± 0.68 |
| 8 | 9.96 ± 1.97 | 8.58 ± 0.24 |
| 9 | NA[c] | NA |
| 10 | 8.89 | NA |
| 11 | 13.85 | 15.473 |
| 12 | 16.13 | NA |
| 13 | 22.70 | 35.40 |
| 14 | 23.60 | 13.47 |
| 15 | 9.91 ± 0.11 | 8.28 ± 2.20 |
| 16 | 16.34 | NA |
| 17 | 25.63 | 40.13 |
| 18 | 11.92 ± 0.40 | 12.03 ± 0.09 |
| 19 | 13.71 ± 1.99 | 27.40 |
| 20 | 12.63 | NA |
| 21 | 13.85 ± 2.10 | 47.16 ± 22.53 |
| 22 | ND[d] | ND |
| 23 | 28.83 | 20.14 |
| 24 | NA | NA |
| 25 | 17.28 ± 6.50 | 9.19 ± 2.47 |
| 26 | 12.79 ± 1.78 | 10.97 ± 1.34 |
| 27 | 10.32 ± 0.56 | 6.17 ± 0.05 |
| 28 | 18.09 ± 4.30 | 13.181 |
| 29 | NA | 11.987 |
| 30 | 77.15 | NA |
| 31 | 25.08 | NA |
| 32 | 20.03 | 34.37 |
| 33 | 22.34 | NA |
| 34 | 25.60 | NA |
| 35 | NA | 88.14 |
| 36 | NA | NA |
| 38 | NA | 22.89 |
| 39 | NA | 65.75 |
| 40 | 23.98 | 23.54 |
| 41 | NA | 22.17 |
| 42 | 28.71 | 12.44 |
| 43 | NA | 25.71 |
| 44 | NA | NA |
| 45 | NA | 31.07 |
| 46 | NA | NA |
| 47 | 43.45 | NA |
| 48 | 25.04 | 37.19 |
| 49 | 17.85 | 17.82 |
| 50 | 13.57 | 20.43 |
| 51 | NA | NA |
| 52 | 8.34 ± 1.63 | 7.04 ± 1.43 |
| 53 | 17.03 ± 4.97 | 19.52 ± 1.019 |
| 54 | 10.33 ± 0.38 | 7.06 ± 3.16 |
| 55 | 5.51 ± 0.02 | 4.171 ± 2.45 |
| 56 | 5.956 | 29.236 |
| 57 | 2.849 | 4.845 |
| 58 | 3.632 | NA |
| 59 | NA | 5.115 |
| 60 | 6.355 | 3.025 |
| 61 | 3.280 | 3.517 |
| 62 | ND | ND |
| 63 | 4.870 | 6.064 |
| 64 | 2.448 | 40.646 |
| 65 | NA | 10.152 |
| 66 | 2.857 | 3.913 |
| 67 | 3.270 | 4.658 |
| 68 | 23.843 | 8.889 |
| 69 | 1.873 | NA |
| 70 | 7.643 | NA |
| 75 | 11.551 | 49.016 |
| 76 | 2.995 | 4.085 |
| 77 | 15.384 | NA |
| 78 | 5.364 | 5.460 |
| 79 | 3.642 | 5.329 |
| 81A | NA | NA |

TABLE 4-continued

Inhibition of the viability of breast cancer cells, IC$_{50}$ (μM)

| Compound No. | MDA-MB-231 cells | MCF7 cells |
|---|---|---|
| 81B | NA | NA |
| 82A | NA | NA |
| 82B | 26.34 | NA |
| 83 | 11.30 ± 0.86 | 10.56 ± 3.06 |
| 84 | 13.54 | 6.89 |
| 85 | NA | NA |
| 86 | NA | NA |
| 87 | 16.34 | NA |
| 88 | 16.13 | NA |
| 89 | NA | NA |
| 90 | 10.68 ± 1.38 | 8.98 |
| 91 | 8.89 | NA |
| 92 | 21.50 | NA |
| 93 | 27.52 | 15.63 |
| 94 | 31.30 | 15.64 |
| 95 | 10.41 ± 1.93 | 6.62 ± 1.93 |
| 96 | 10.440 | NA |
| 97 | 21.3681 | ND |
| 98 | 1.623 | ND | a)tamoxifen as positive compound.
b)when the compound is tested more than 3 times, IC$_{50}$ will be shown as the average ± standard deviation.
c)NA means no activity, IC$_{50}$ being above 100 μM.
d)ND means not being detected.

Example 118

CellTiter-Glo® Luminescent Assay to Measure the Inhibitory Activity of the Compounds on In Vitro Growth of Endometrial Cancer HEC-1A Cells HEC-1A cells are endometrial cancer cell lines only expressing ER-36. Human endometrial cancer HEC-1A cells were obtained from ATCC and maintained in DMEM and 10% fetal calf serum at 37° C., under 5% CO$_2$ atmosphere. The cells were seeded on 96-well plate at a density of 6×10$^3$ cells per well. HEC-1A cells were treated with a test compound dissolved in DMSO at the concentrations of zero, 0.3 μM, 0.5 μM, 1 μM, 2 μM, 3 μM, 5 μM, 20 μM, 30 μM, 50 μM and 100 μM for 72 hours. Treated cells were examined by CellTiter-Glo® Luminescent Cell Viability Assay Kit (Promega), and luminescence values were recorded with Envision. The results of some compounds are shown in Table 5.

TABLE 5

| Compound No. | Inhibition of the viability of endometrial cancer cells, IC$_{50}$ (μM) HEC-1A cells |
|---|---|
| Tamoxifen$^{a)}$ | 19.46 |
| 5 | 7.139 |
| 6 | 4.016 |
| 15 | 8.353 |
| 18 | 13.796 | a)Tamoxifen as positive control compound

Example 119

Inhibition of the Compounds on In Vitro Growth of Different Breast Cancer Cells

A: In Vitro CellTiter-Glo® Luminescent Cell Viability Assay on Ovary Cancer HO8910 Cells Ovary cancer HO8910 cells were obtained from Type Culture Collection of the Chinese Academy of Sciences, Shanghai, and maintained in RPMI-1640 and 10% fetal calf serum at 37° C., under 5% CO$_2$ atmosphere. The cells were seeded on 96-well plate at a density of 6×10$^3$ cells per well. HO8910 cells were treated with a test compound dissolved in DMSO at the concentrations of zero, 0.3 μM, 0.5 μM, 1 μM, 2 μM, 3 μM, 5 μM, 10 μM, 20 μM, 30 μM, 50 μM and 100 μM for 72 hours. Treated cells were examined by CellTiter-Glo® Luminescent Cell Viability Assay Kit (Promega), and luminescence values were recorded with Envision.

B: In Vitro CellTiter-Glo® Luminescent Cell Viability Assay on Ovary Cancer CoC1 Cells The ovary cancer CoC1 cells were obtained from Cancer hospital, Chinese Academy of Medical Sciences and maintained in RPMI-1640 and 10% fetal calf serum at 37° C., under 5% CO$_2$ atmosphere. The cells were seeded on 96-well plate at a density of 6×10$^3$ cells per well. CoC1 cells were treated with a test compound dissolved in DMSO at the concentrations of zero, 0.3 μM, 0.5 μM, 1 μM, 2 μM, 3 μM, 5 μM, 10 μM, 30 μM, 50 μM and 100 μM for 72 hours. Treated cells were examined by CellTiter-Glo® Luminescent Cell Viability Assay Kit (Promega), and luminescence values were recorded with Envision.

C: In Vitro CellTiter-Glo® Luminescent Cell Viability Assay on Ovary Cancer SK-OV3 Cells The ovary cancer SK-OV3 cells were obtained from Cancer hospital, Chinese Academy of Medical Sciences and maintained in RPMI-1640 and 10% fetal calf serum at 37° C., under 5% CO$_2$ atmosphere. The cells were seeded on 96-well plate at a density of 6×10$^3$ cells per well. SK-OV3 cells were treated with a test compound dissolved in DMSO at the concentrations of zero, 0.3 μM, 0.5 μM, 1 μM, 2 μM, 3 μM, 5 μM, 10 μM, 20 μM, 30 μM, 50 μM and 100 μM for 72 hours. Treated cells were examined by CellTiter-Glo® Luminescent Cell Viability Assay Kit (Promega), and luminescence values were recorded with Envision.

The effects of some of the present compounds in inhibiting the viability of different breast cancer cells are shown below in Table 6.

TABLE 6

| | Inhibition of the viability of ovary cancer cells, IC$_{50}$ (μM) | | |
|---|---|---|---|
| Compound No. | SK-OV3 cells | COC1 cells | HO-8910 cells |
| tamoxifen$^{a)}$ | 19.25 ± 2.94b) | 14.62 ± 4.40 | 26.65 ± 0.04 |
| 2 | 7.22 | 5.185 | 15.74 |
| 4 | 6.423 | NDc) | 13.973 |
| 5 | ND | 6.914 | ND |
| 7 | NAd) | NA | 21.552 |
| 8 | 24.317 | 11.829 | 22.348 |
| 25 | 12.561 | 14.284 | NA |
| 26 | 40.091 | 17.811 | 24.274 |
| 27 | 7.226 | 9.232 | 17.578 |
| 84 | 15.744 | 23.389 | 23.404 |
| 90 | NA | NA | NA | a)tamoxifen as positive control compound
b)when the compound is tested more than 3 times, IC$_{50}$ will be shown as the average ± standard deviation.
c)ND means not being detected.
d)NA means no activity, IC$_{50}$ being above 100 μM

Example 120

Inhibition of the Compounds on In Vitro Growth of Different Leukemia Cells

A: In Vitro CellTiter-Glo® Luminescent Cell Viability Assay on Leukemia K562 Cells The leukemia K562 cells were obtained from ATCC and maintained in IMDM and 10% fetal calf serum at 37° C., under 5% $CO_2$ atmosphere. The cells were seeded on 96-well plate at a density of $6\times10^3$ cells per well. K562 cells were treated with a test compound dissolved in DMSO at the concentrations of zero, 0.3 µM, 0.5 µM, 1 µM, 2 µM, 3 µM, 5 µM, 10 µM, 20 µM, 30 µM, 50 µM and 100 µM for 72 hours. Treated cells were examined by CellTiter-Glo® Luminescent Cell Viability Assay Kit (Promega), and luminescence values were recorded with Envision.

B: In Vitro CellTiter-Glo® Luminescent Cell Viability Assay on Leukemia HL-60 Cells The leukemia HL-60 cells were obtained from ATCC and maintained in IMDM and 10% fetal calf serum at 37° C., under 5% $CO_2$ atmosphere. The cells were seeded on 96-well plate at a density of $6\times10^3$ cells per well. HL-60 cells were treated with a test compound dissolved in DMSO at the concentrations of zero, 0.3 µM, 0.5 µM, 1 µM, 2 µM, 3 µM, 5 µM, 10 µM, 20 µM, 30 µM, 50 µM and 100 µM for 72 hours. Treated cells were examined by CellTiter-Glo® Luminescent Cell Viability Assay Kit (Promega), and luminescence values were recorded with Envision.

C: In Vitro CellTiter-Glo® Luminescent Cell Viability Assay on Leukemia Molt-4 Cells The leukemia Molt-4 cells were obtained from ATCC and maintained in RPMI-1640 and 10% fetal calf serum at 37° C., under 5% $CO_2$ atmosphere. The cells were seeded on 96-well plate at a density of $6\times10^3$ cells per well. RPMI-1640 cells were treated with a test compound dissolved in DMSO at the concentrations of zero, 0.3 µM, 0.5 µM, 1 µM, 2 µM, 3 µM, 5 µM, 10 µM, 20 µM, 30 µM, 50 µM and 100 µM for 72 hours. Treated cells were examined by CellTiter-Glo® Luminescent Cell Viability Assay Kit (Promega), and luminescence values were recorded with Envision.

The effects of some of the present compounds in inhibiting the viability of different breast cancer cells are shown below in Table 7.

TABLE 7

| Compound No. | Inhibition of the viability of leukemia cells, $IC_{50}$ (µM) | | |
|---|---|---|---|
| | K562 cells | HL-60 cells | Molt-4 cells |
| Tamoxifen[a] | 18.22 ± 5.65[b] | 8.19 ± 3.89 | 11.661 |
| 2 | NA[c] | NA | NA |
| 4 | 8.652 | 10.126 | 10.282 |
| 5 | 12.022 | 8.959 | 9.126 |
| 6 | NA | NA | NA |
| 8 | 12.77 | 17.873 | 15.284 |
| 15 | 12.38 | 15.741 | 13.24 |
| 18 | NA | NA | 14.195 |
| 25 | NA | NA | NA |
| 83 | NA | NA | NA |

[a]tamoxifen as positive compound.
[b]when the compound is tested more than 3 times, $IC_{50}$ will be shown as the average ± standard deviation.
[c]NA means no activity, $IC_{50}$ being above 100 µM.

Example 121

Inhibition of the Compounds on In Vitro Growth of Liver Cancer Cells

The liver cancer Hep3B2.1-7 cells were obtained from ATCC. Cells were incubated in 1640 culture medium with 5% fetal calf serum and 100 U/ml double-antibody in a cell incubator at 37° C., 5% $CO_2$ atmosphere and passaged via conventional methods. The sample was dissolved in DMSO, formulated into 50 mg/ml stocking solution, and stored at 4° C. The test solutions at 50, 25, 12.5 and 6.25 µg/ml were formulated with culture medium immediately before use.

The adherent cells were digested with cell digestive solution, and then the exfoliated cells were collected and counted. The cell suspension was formulated with 1640 culture medium containing 5% fetal calf serum ($5.0\times10^4$/ml). The cell suspension was seeded on 96-well plate with 100 µl/well, and maintained in a cell incubator at 37° C., 5% $CO_2$ atmosphere for 24 hours. After that, the compounds at various concentrations were added, where solvent was taken as negative control and Taxol as positive control. 10 µl MTT (5 mg/ml) was added after 72 hours. The supernatant was removed after cultivation for 3 hours more, 150 µl DMSO was added and the formazan was dissolved on shaking. OD values were measured at 570 nm after homogeneous mixing, and inhibition rate and $IC_{50}$ values were calculated based on the mean of OD values from 3 wells.

The effects of some of the present compounds in inhibiting the growth of liver cancer cells are shown below in Table 8.

TABLE 8

| Compound No. | Inhibition on liver cancer cells, $IC_{50}$ (µg/mL) Hep3B2.1-7cells |
|---|---|
| Taxol[a] | 42.79 |
| 4 | 1.38 |
| 5 | 1.45 |
| 7 | 1.09 |
| 8 | 1.46 |
| 10 | 9.43 |
| 15 | 0.00138 |
| 57 | 21.03 |
| 60 | 9.95 |
| 61 | 0.04 |
| 63 | 13.99 |
| 66 | 0.24 |
| 69 | 3.89 |
| 70 | 0.39 |
| 75 | 0.83 |
| 76 | 5.79 |
| 77 | 3.08 |
| 78 | 8.95 |
| 79 | 8.23 |
| 98 | 0.0144 |

[a]Taxol as positive control compound.

Example 122

Regulation of Compounds to ER-α36 Protein Expression in Cancer Cells

Figure 4:
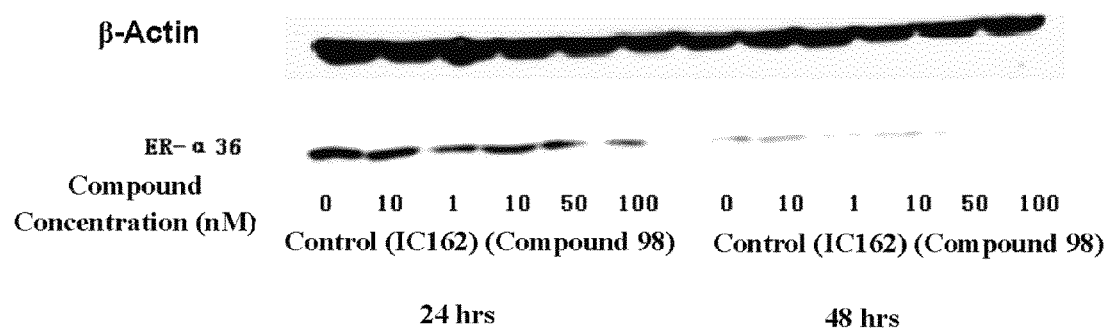
FIG. 4 shows the variations of ER-α36 protein expression in 24-hour and 48-hour after different concentrations of compound 98 were administrated to endometrial carcinoma HEC-1A cell, indicating the effect of the compound in regulating ER-α36.

Taking endometrial cancer HEC-1A cells as an example, serum-depleted HEC-1A cells were treated with compounds at concentrations of 1, 10, 50 and 100 nM for 24 hours and 48 hours. The treated cells were washed with PBS and lysed with lysis buffer (a mixture of 1*PBS (pH7.4), 1% NP-40, 0.7 mMEDTA, and protease inhibitor from Roche). The lysates were boiled for 5 minutes in a SDS gel loading buffer (25 mM Tris-Cl pH 6.8; 10% SDS; 2% glycerol; 20% β-mercaptoethanol; 0.01% bromophenol blue) and separated on a 10% SDS-PAGE gel. After electrophoresis, the proteins were transferred onto PVDF membrane (Millipore Transfer Membrane). The membrane was probed with Rabbit anti-ER36 antibody which is specific to 20 amino acid polypeptides at C-terminus of ER-α36. Then the membrane was incubated with an HRP-conjugated secondary antibody and visualized with ECL detection reagents. FIG. 4 shows that the regulation of compound 98 at 4 concentrations (1, 10, 50 and 100 nm) and at two points of time (24 hours and 48 hours) to the expression of ER-36 in cells. It can be seen that the expression of ER-36 in cells was dramatically reduced above the concentration of 50 nM.

In Vivo Evaluation

Example 123

Inhibition of Compounds on Growth of Human Breast Cancer BCAP-37 Cells Xenograft Tumor in Nude Mice Nude mice with breast cancer xenografts were treated with the test compounds to test their effects on inhibiting tumor growth. Tumor tissues were taken from nude mice bearing BCAP-37 cells and cut into small pieces. Several pieces of the tumor tissues were implanted into the armpit under the right front limb of female nude mice. After implantation, the mice were injected with E2β solution at a dose of 7 μg per mouse once every day for 6 days to stimulate growth of tumor in the receiving mice. Beginning at day 7, the mice were administered intragastrically with the test compounds at a dose of 35 mg/kg. Tamoxifen was taken as a positive control. Corn oil was taken as a negative control. The test compounds were prepared as a corn oil solution (20 mg/mL). The mice were given the test compounds and Tamoxifen at a dose of 35 mg/kg or corn oil for 15-21 days. Then the mice were sacrificed and dissected, the tumor tissues were taken out and weighed. The tumor growth inhibition rate was calculated according to the following equation:

tumor growth inhibition percentage=(average weight of the tumor in the negative control group–average weight of the tumor treated with test compound)/average weight of the tumor in the negative control group.

Figure 5A:
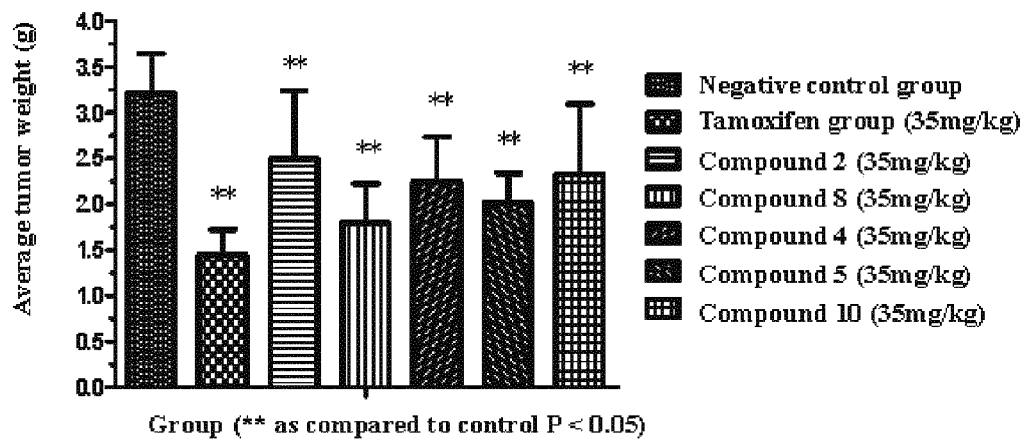
FIG. 5 shows the average tumor weight (bar chart a) and inhibiting rate of tumor (bar chart b) of nude mice bearing human breast cancer BCAP-37 cells after continuously administrating positive control of tamoxifen (0.7 mg/mouse/day), compounds 2, 8, 4, 5 and 10 (0.7 mg/mouse/day), and negative control of corn oil (0.2 mL/mouse/day) for 20 days.
Figure 5B:
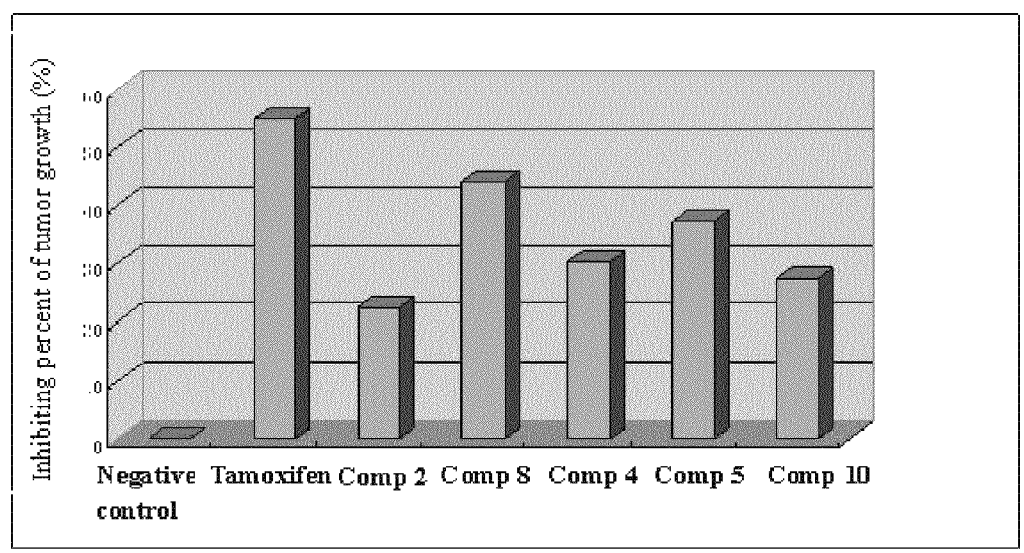
Figure 6A:
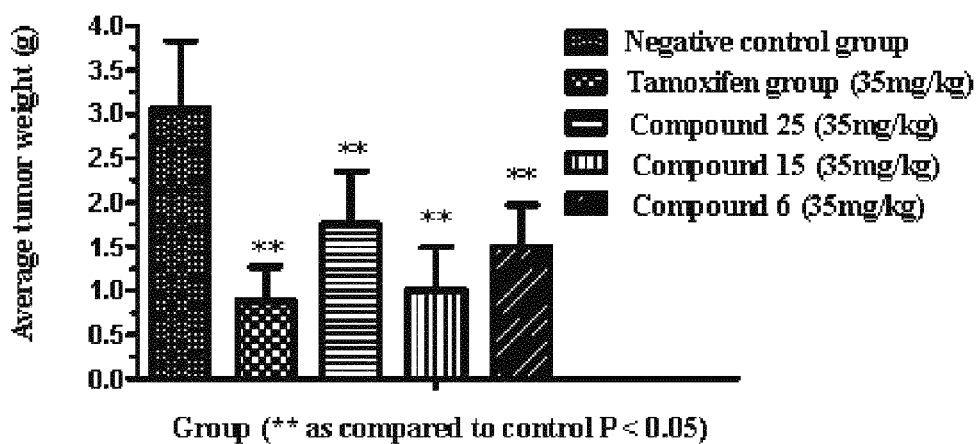
FIG. 6 shows the average tumor weight (bar chart a) and inhibiting rate of tumor (bar chart b) of nude mice bearing human breast cancer BCAP-37 cells after continuously administrating positive control of tamoxifen (0.7 mg/mouse/day), compounds 25, 15, and 6 (0.7 mg/mouse/day), and negative control of corn oil (0.2 mL/mouse/day) for 20 days.
Figure 6B:
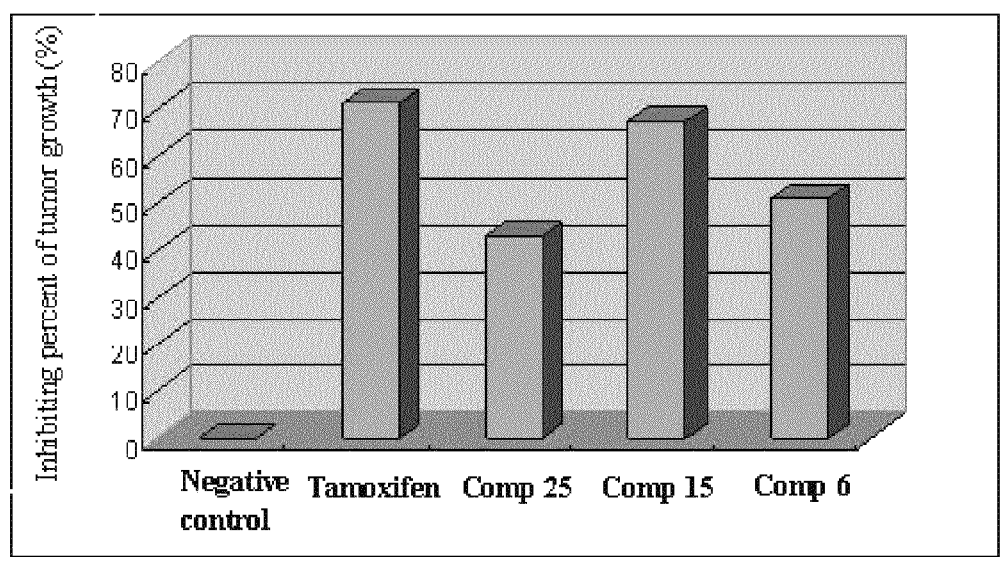
Figure 7A:
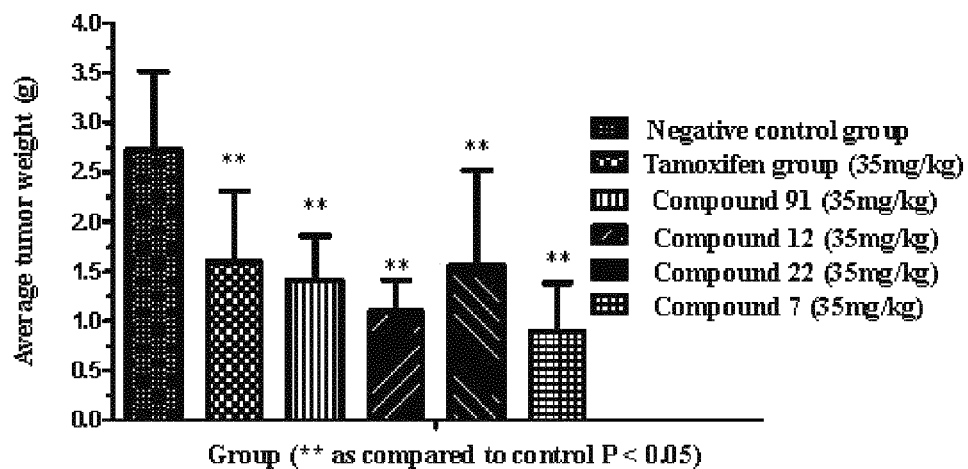
FIG. 7 shows the average tumor weight (bar chart a) and inhibiting rate of tumor (bar chart b) of nude mice bearing human breast cancer BCAP-37 cells after continuously administrating positive control of tamoxifen (0.7 mg/mouse/day), compounds 91, 12, 22, and 7 (0.7 mg/mouse/day), and negative control of corn oil (0.2 ml/mouse/day) for 20 days.
Figure 7B:
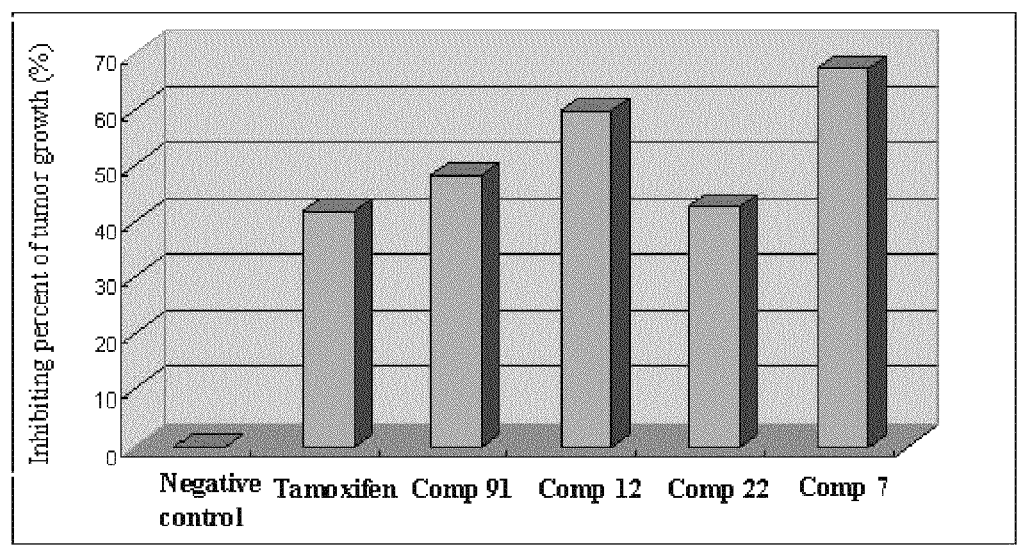

The results were drawn in the faint of bar graph and shown in FIGS. 5, 6 and 7.

Example 124

Figure 8:
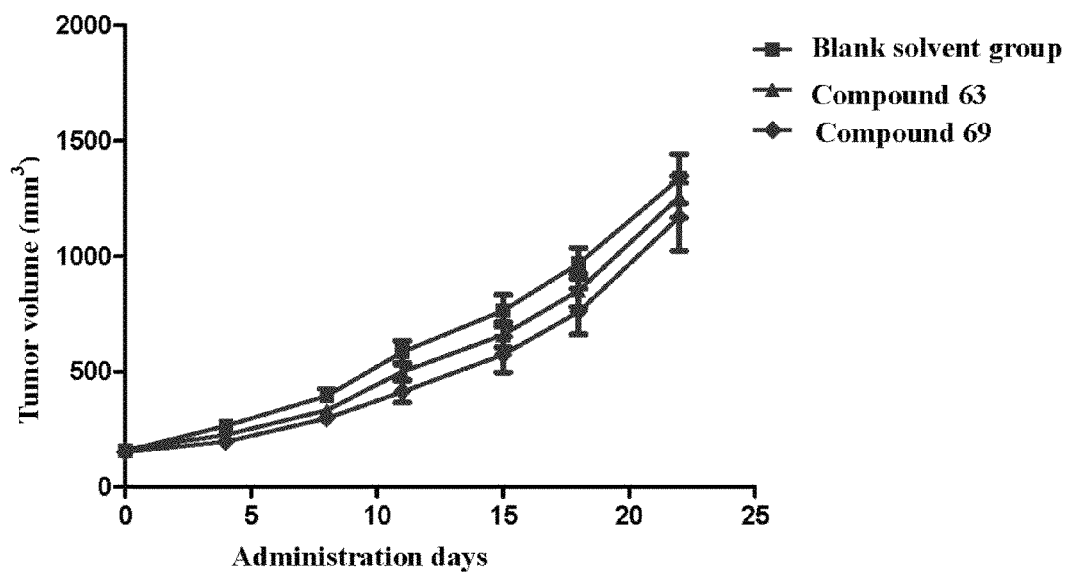
FIG. 8 shows the tumor growth curve of nude mice bearing Human Acute Myeloid Leukemia MV-4-11 Cells after continuously administrating compounds 63 and 69 (0.7 mg/mouse/day) and negative control of blank solvent medium (0.2 ml/mouse/day) for 22 days.

Inhibition of Compounds on Growth of Human Acute Myeloid Leukemia MV-4-11 Cells Xenograft Tumor in Nude Mice Nude mice with Human Acute Myeloid Leukemia MV-4-11 Cells Xenograft Tumor were treated with the test compounds to test their effects on inhibiting tumor growth. Human Acute Myeloid Leukemia MV-4-11 Cells were obtained from ATCC. 1×10⁷ cells through 5 passages plus 0.2 mL Matrigel were implanted subcutaneously into the armpit under the right front limb of male nude mice. When the tumor of the nude mice reached 150 mm³, the tumor-bearing nude mice were grouped randomly, 10 nude mice per group. The mice were administered intragastrically with mixed oil as negative control group. The test compounds were dissolved in mixed oil for intragastrical administration. The administration period is 22 days continuously. The nude mice were administered intragastrically with the test compounds in mixed oil suspension (35 mg/kg) or blank mixed oil solvent medium once a day. During the administration, the tumor volume and nude mice weight were measured twice a week. The tumor growth curve was plotted based on tumor volume and administration time (FIG. 8), whereby the effect of the compound on the growth of tumor may be estimated.

Example 125

Figure 9:
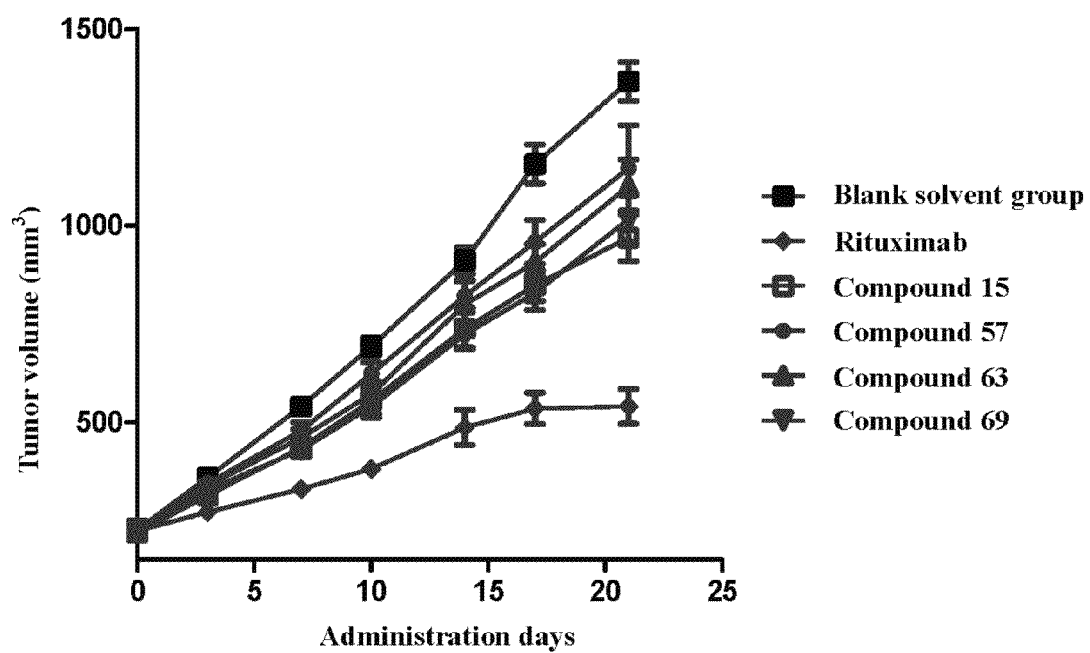
FIG. 9 shows the tumor growth curve of nude mice bearing human B lymphoma Daudi cells after continuously administrating positive control of Rituximab, compounds 15, 57, 63, and 69 (0.7 mg/mouse/day) and negative control of blank solvent medium (0.2 ml/mouse/day) for 21 days.

Inhibition of Compounds on Growth of Human B Cell Lymphomas Daudi Xenograft Tumor in Nude Mice Nude mice with Human B cell Lymphomas Daudi Xenograft Tumor were treated with the test compounds to test their effects on inhibiting tumor growth. Human B cell Lymphomas were obtained from ATCC. 1×10⁷ cells through 5 passages plus 0.2 mL Matrigel were implanted subcutaneously into the armpit under the right front limb of male nude mice. When the tumor of the nude mice reached 150-200 mm³, the tumor-bearing nude mice were grouped randomly, 10 nude mice per group. The group to which mixed oil was intragastrically adminstered was taken as negative control, and the group to which rituximab was intravenously administered was taken as positive control. The test compounds were administered intragastrically as being dissolved in the mixed oil. The administration period is 21 days continuously. The mixed oil suspension (35 mg/kg) of test compound was administered intragastrically to the nude mice of the testing group once a day. The positive control group was injected with Rituximab (20 mg/kg) twice a week. The negative control group was intragastrically administered with mixed oil medium every day. During the administration, the tumor volume and nude mice weight were measured twice a week. The tumor growth curve was plotted based on tumor volume and administration time (FIG. 9), whereby the effect of the compound on the growth of tumor may be estimated.

The invention claimed is:

1. A compound of formula (I)

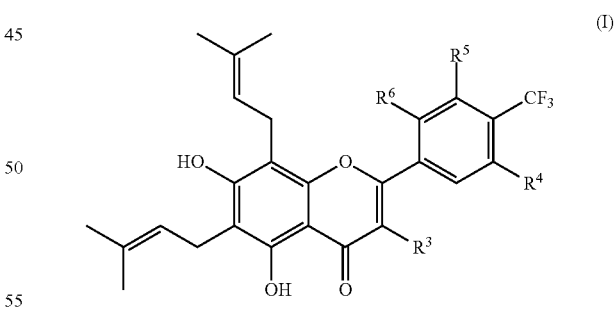

or a pharmaceutically acceptable salt or solvate thereof, wherein:

$R_3$ is selected from the group consisting of hydrogen, hydroxy, ($C_{1-6}$) alkyl, ($C_{1-6}$) alkoxy, halogen, amino, ($C_{1-6}$)alkoxy substituted with one or more halogen atoms;

$R_4$ and $R_5$ are independently selected from the group consisting of hydrogen, halogen, hydroxy, hydroxy($C_1$-$C_6$) alkyl, amino, amino($C_1$-$C_6$)alkyl, formyl, formamido, cyano, nitro, HO—(C=O)—, —SO$_3$H, ($C_1$-$C_6$)alkyl, ($C_1$-$C_6$)alkyl substituted with one or more halogen atoms, $(C_2-C_6)$alkenyl, $(C_2-C_6)$alkynyl, $(C_1-C_6)$alkoxy, $(C_1-C_6)$alkoxy substituted with one or more halogen atoms, $(C_2-C_6)$alkenoxy, $(C_1-C_6)$alkylcarbonyl, $(C_1-C_6)$alkoxycarbonyl, N—$(C_1-C_6)$alkylaminocarbonyl, N,N—[$(C_1-C_6)$alkyl]$_2$aminocarbonyl, N—$(C_6-C_{10})$arylaminocarbonyl, N,N—[$(C_6-C_{10})$aryl]2aminocarbonyl, N—$(C_1-C_6)$alkyl-N—$(C_1-C_6)$alkylaminocarbonyl, N—$(C_1-C_6)$alkyl-N—$(C_6-C_{10})$arylaminocarbonyl, N,N—[$(C_1-C_6)$alkyl]$_2$amino, N—$(C_1-C_6)$alkylamino, N—$(C_6-C_{10})$arylamino, N,N—[$(C_6-C_{10})$aryl]$_2$amino, N—$(C_1-C_6)$alkyl-N—$(C_1-C_6)$alkylamino, N—$(C_1-C_6)$alkyl-N—$(C_6-C_{10})$arylamino, N,N—[$(C_1-C_6)$alkylaryl]$_2$ amino, $(C_6-C_{10})$aryl, substituted $(C_6-C_{10})$aryl, $(C_6-C_{10})$aryloxy, 5-10 membered heteroaryl, substituted 5-10 membered heteroaryl, 5-10 membered heteroaryloxy, aminosulfonyl, N—$(C_1-C_6)$alkylaminosulfonyl, N,N—[$(C_1-C_6)$alkyl]$_2$aminosulfonyl, morpholine sulfonyl, piperidine sulfonyl, piperazine sulfonyl, N-methylpiperazinesulfonyl, N-benzylpiperazinesulfonyl, pyrrolidinylsulfonyl, methylsulfonyl, trifluoromethylsulfonyl, trifluoromethylsulfinyl, p-tosyl, thiol, $(C_1-C_6)$alkylthio, $(C_1-C_6)$alkylthio substituted with one or more halogen atoms; or $R_4$ and $R_5$ are taken together to form —O$(CH_2)_n$O—, n is 1-3; $R_6$ is selected from the group consisting of hydrogen, halogen, hydroxy and amino.

2. The compound of formula (I) of claim 1,

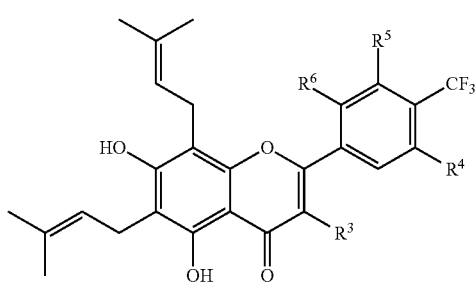

(I)

or a pharmaceutically acceptable salt or solvate thereof, wherein:

$R_3$ is selected from the group consisting of hydrogen, hydroxy, methyl and methoxy;

$R_4$ and $R_5$ are independently selected from the group consisting of hydrogen, halogen, hydroxy, hydroxy$(C_1-C_6)$ alkyl, amino, amino$(C_1-C_6)$alkyl, formyl, formamido, cyano, nitro-, HO—(C=O)—, —SO$_3$H, $(C_1-C_6)$alkyl, $(C_1-C_6)$alkyl substituted with one or more halogen atoms, $(C_1-C_6)$alkoxy, $(C_1-C_6)$alkoxy substituted with one or more halogen atoms, $(C_1-C_6)$alkylcarbonyl, $(C_1-C_6)$alkoxycarbonyl, N—$(C_1-C_6)$alkyl aminocarbonyl, N—$(C_6-C_{10})$arylaminocarbonyl, N,N—[$(C_6-C_{10})$aryl]$_2$ aminocarbonyl, N—$(C_6-C_{10})$arylamino, $(C_6-C_{10})$aryl, substituted $(C_6-C_{10})$aryl, $(C_6-C_{10})$aryloxy, 5-10 membered heteroaryl, substituted 5-10 membered heteroaryl, 5-10 membered heteroaryloxy, aminosulfonyl, N—$(C_1-C_6)$alkylaminosulfonyl, N,N—[$(C_1-C_6)$alkyl]$_2$aminosulfonyl, morpholine sulfonyl, piperidine sulfonyl, piperazine sulfonyl, N-methylpiperazinesulfonyl, N-benzylpiperazinesulfonyl, pyrrolidinylsulfonyl, methylsulfonyl, trifluoromethylsulfonyl, trifluoromethylsulfinyl, p-tosyl, thiol, $(C_1-C_6)$alkylthio, $(C_1-C_6)$alkylthio substituted with one or more halogen atoms; or $R_4$ and $R_5$ are taken together to form —O$(CH_2)_n$O—, n is 1-3; $R_6$ is selected from the group consisting of hydrogen, halogen, hydroxy and amino.

3. The compound of claim 2 is selected from the group consisting of:
2-(3-fluoro-4-trifluoromethylphenyl)-5,7-dihydroxy-3-methoxy-6,8-di(3-methyl-2-buten-1-yl)-4H-benzopyran-4-one;
2-(4-trifluoromethylphenyl)-5,7-dihydroxy-3-methoxy-6,8-di(3-methyl-2-buten-1-yl)-4H-benzopyran-4-one;
2-(4-trifluoromethylphenyl)-3,5,7-trihydroxy-6,8-di(3-methyl-2-buten-1-yl)-4H-benzopyran-4-one; and
2-(3-hydroxy-4-trifluoromethylphenyl)-5,7-dihydroxy-3-methoxy-6,8-di(3-methyl-2-buten-1-yl)-4H-benzopyran-4-one.

4. A pharmaceutical composition comprising an effective dose of the compound according to claim 1, or a pharmaceutically acceptable salt or solvate, and one or more pharmaceutically acceptable excipients.

* * * * *